(12) United States Patent
Siler-Khodr

(10) Patent No.: US 6,635,739 B2
(45) Date of Patent: *Oct. 21, 2003

(54) NON-MAMMALIAN GNRH ANALOGS AND USES THEREOF IN REGULATION OF FERTILITY AND PREGNANCY

(76) Inventor: Theresa Siler-Khodr, 13 Mayborough La., San Antonio, TX (US) 78257

(*) Notice: Subject to any disclaimer, the term of this patent is extended or adjusted under 35 U.S.C. 154(b) by 3 days.

This patent is subject to a terminal disclaimer.

(21) Appl. No.: 09/941,094

(22) Filed: Aug. 28, 2001

(65) Prior Publication Data

US 2002/0065226 A1 May 30, 2002

Related U.S. Application Data

(63) Continuation-in-part of application No. 09/419,161, filed on Oct. 15, 1999, now Pat. No. 6,323,179.

(51) Int. Cl.$^7$ .................... A61K 38/00; A61K 38/24; A61K 38/04; C07K 16/00; C07K 14/00
(52) U.S. Cl. .................... 530/300; 530/313; 530/328; 530/332; 530/333; 530/335; 514/15
(58) Field of Search ................ 514/15, 2; 530/313, 530/328, 332, 333, 335, 300

Primary Examiner—John Ulm
Assistant Examiner—Olga N. Chernyshev

(74) Attorney, Agent, or Firm—Michelle Evans; Gunn, Lee & Hanor, P.C.

(57) ABSTRACT

Specially designed non-mammalian GnRH analog decapeptides resistant to degradation by the placental enzyme, C-ase-1, or a post-proline peptidase, are disclosed. The GnRH analogs are further defined as analogs of chicken II GnRH or salmon GnRH. These non-mammalian analogs incorporate D-arginine, D-leucine, D-tBu-Serine, D-Trp or other active D amino acids at position 6 and ethylamide, aza-Gly-amide or other Gly amide at position 10. The D-Arg (6)-chicken II GnRH-ethylamide, D-Arg (6)-chicken II GnRH-aza-Gly(10)-amide, the D-Arg (6)-salmon GnRH ethylamide, and D-Arg (6)-salmon GnRH-aza-Gly(10)-amide analogs are also provided, and demonstrate preferential binding to chorionic GnRH, ovarian, endometrial, tubal, uterine, prostate and testicular receptors. Biopotency is greater at the ovary and endometrium than at the pituitary. These non-mammalian GnRH analogs may be used in pharmaceutical preparation, and specifically in various treatment methods as a contraceptive or post-coital contraceptive agent. The non-mammalian GnRH analogs are also provided in pharmaceutical preparations that may be used clinically for maintaining pregnancy when used in very low doses and administered in pulsatile fashion, as well as in preparations for the treatment of endometriosis, ovarian cysts, and leimyomas. In another aspect, the non-mammalian GnRH analogs may be used a luteolytic agents. The aza-Gly(10) amide non-mammalian analogs are yet other embodiments of the non-mammalian GnRH analogs provided as a part of the invention.

8 Claims, 34 Drawing Sheets

| Placenta No. | Kd Analog (nM) | | | | |
|---|---|---|---|---|---|
| | GnRH | Buserelin | ArgIIethy INH2 | ArgIIethy INH2 | ArgIIazagly NH2 |
| Placenta 2 | 2000 | 746 | 112 | | 67 |
| Placenta 3 | 1666 | 503 | 266 | | 73 |
| Placenta 4 | 3597 | 488 | 529 | | 138 |
| Mean | 2421 | 579 | 302 | | 93 |
| SEM | 596 | 84 | 122 | | 23 |

| Placenta No. | Normalized to mammalian GnRH Kd analog/Kd mGnRH | | | | |
|---|---|---|---|---|---|
| | GnRH | Buserelin | ArgIIethy INH2 | | ArgIIazagly NH2 |
| Placenta 2 | 1.000 | 0.373 | 0.056 | | 0.034 |
| Placenta 3 | 1.000 | 0.302 | 0.160 | | 0.044 |
| Placenta 4 | 1.000 | 0.136 | 0.147 | | 0.038 |
| Mean | | 0.270 | 0.121 | | 0.039 |
| SEM | | 0.070 | 0.033 | | 0.003 |

Fig. 1

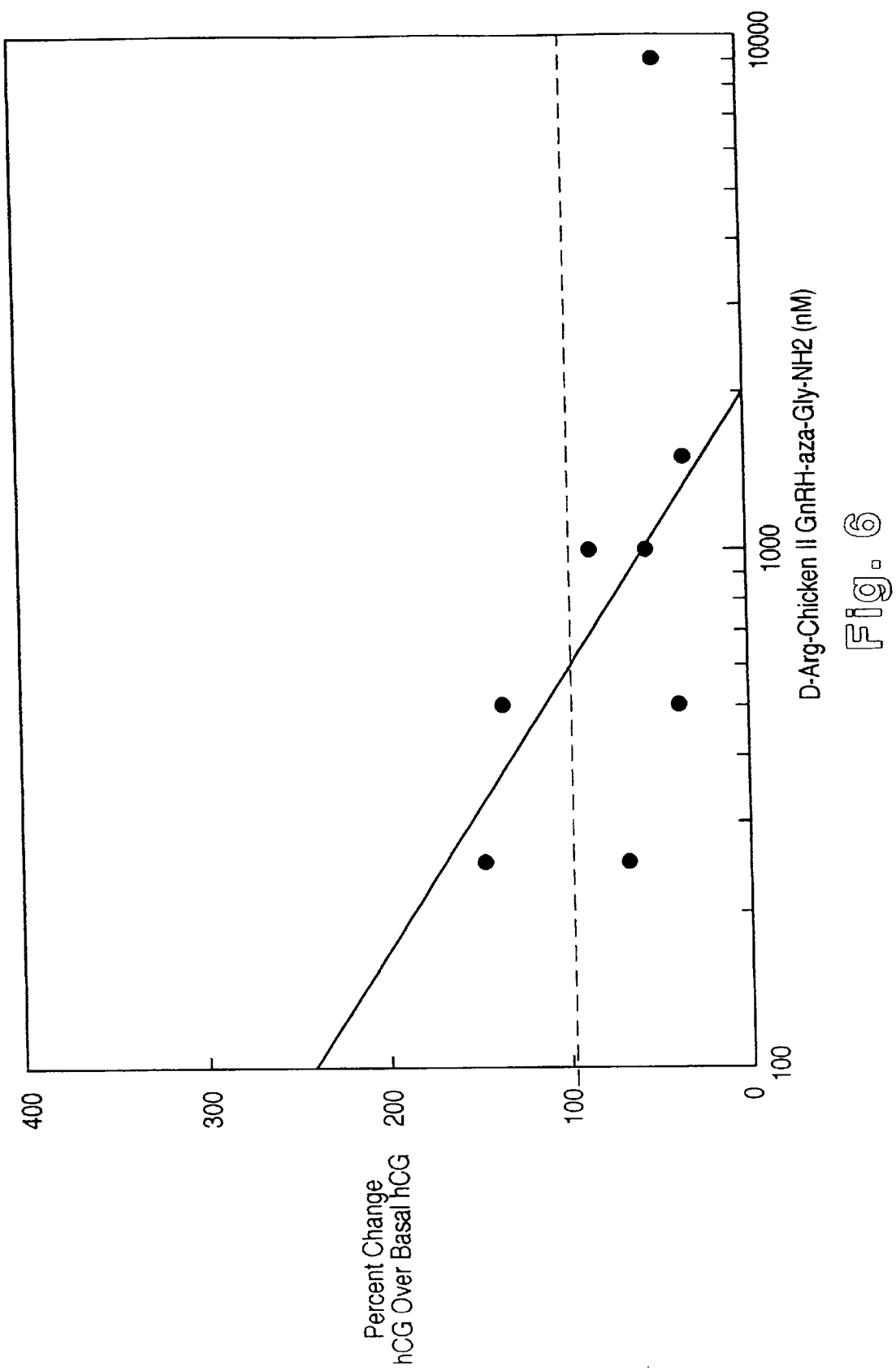

| Term placenta | hCG (percentage of basal release) Analog (uM) | | | | | |
|---|---|---|---|---|---|---|
| | 0.250 | 0.500 | 1.000 | 1.500 | 9.000 |
| Pl 1 | 392 | 136 | 87 | | |
| Pl 2 | 67 | 39 | 56 | | |
| Pl 3 | 79 | 93 | | | |
| Pl 4 | 147 | | | | |
| Mean | 171 | 89 | 72 | 34 | 47 |
| SEM | 64 | 19 | 9 | 34 | 47 |

Fig. 7

| Term placenta | Progesterone (ng/mL/mg/h) Analog (uM) | | | | | |
|---|---|---|---|---|---|---|
| | 0.000 | 0.250 | 0.500 | 1.000 | 1.500 | 9.000 |
| Pl 1 | 0.103 | 0.088 | 0.075 | 0.048 | | |
| Pl 2 | 0.077 | 0.058 | 0.045 | 0.054 | | |
| Pl 3 | 0.198 | 0.159 | 0.170 | 0.165 | | |
| Pl 4 | 0.081 | 0.081 | | | | |
| Mean | 0.115 | 0.097 | 0.097 | 0.089 | 0.056 | 0.063 |
| SEM | 0.024 | 0.018 | 0.028 | 0.029 | 0.056 | 0.063 |

Fig. 8

| Term placenta | PGE$_2$ (pg/mL/mg/h) Analog (uM) | | | | |
|---|---|---|---|---|---|
| | 0.000 | 0.250 | 0.500 | 1.000 | |
| PI 1 | 8.300 | 3.100 | 4.600 | 5.500 | |
| PI 2 | 4.685 | 3.430 | 5.631 | 6.308 | |
| PI 3 | 9.200 | 11.500 | 15.300 | | |
| Mean | 7.395 | 6.010 | 8.510 | 5.904 | |
| SEM | 1.043 | 2.113 | 2.613 | 0.233 | |

Fig. 9A

| Term placenta | PGE$_2$ (pg/mL/mg/h) Analog (uM) | | | | |
|---|---|---|---|---|---|
| | 0.000 | 0.250 | 0.500 | 1.000 | |
| PI 1 | 5.800 | 6.000 | 3.200 | 2.500 | |
| PI 2 | 34.000 | 14.400 | 16.800 | 16.800 | |
| PI 3 | 54.700 | 31.400 | 42.500 | 46.600 | |
| Mean | 31.500 | 17.267 | 20.833 | 21.967 | |
| SEM | 9.892 | 5.440 | 8.340 | 9.481 | |

Fig. 9B

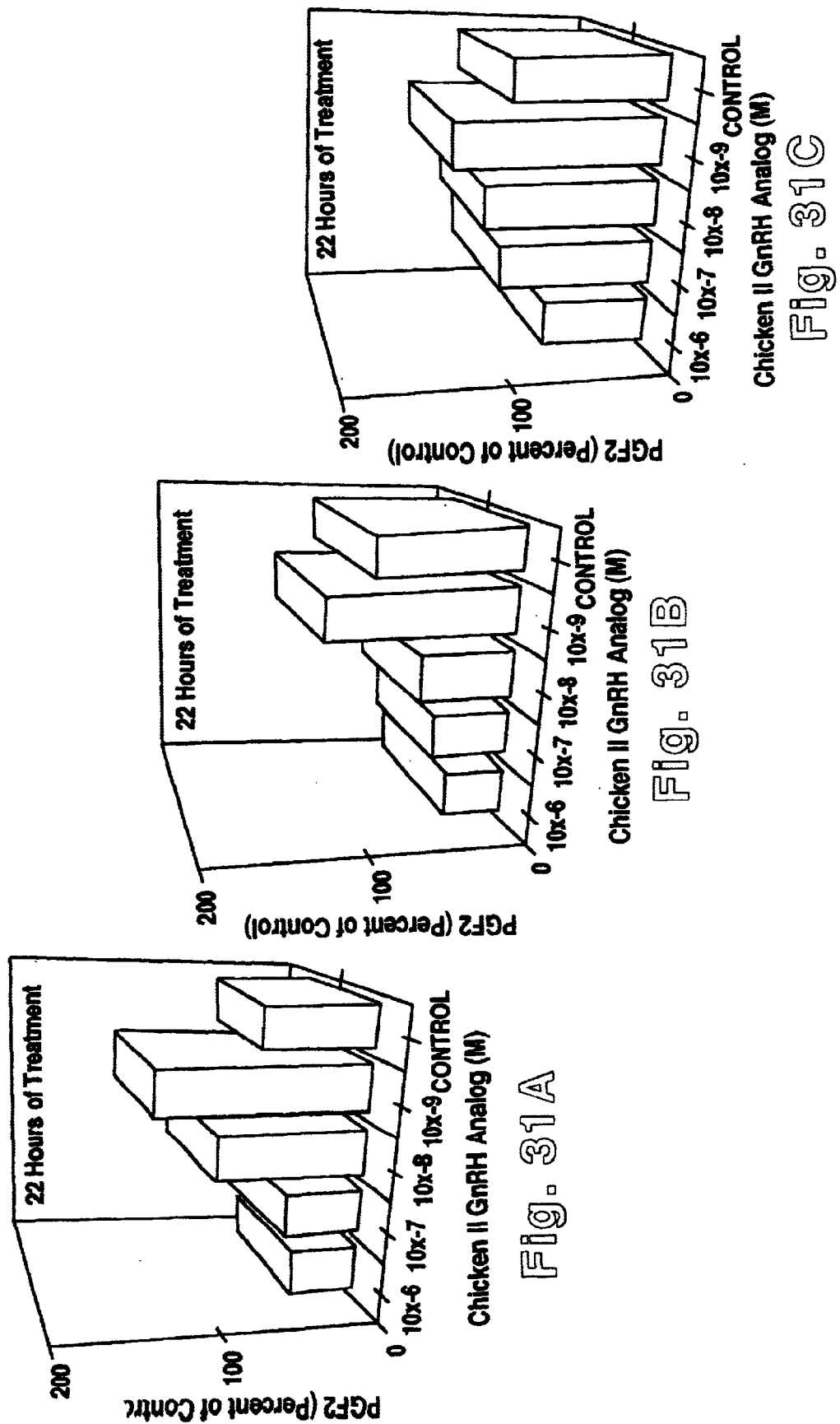

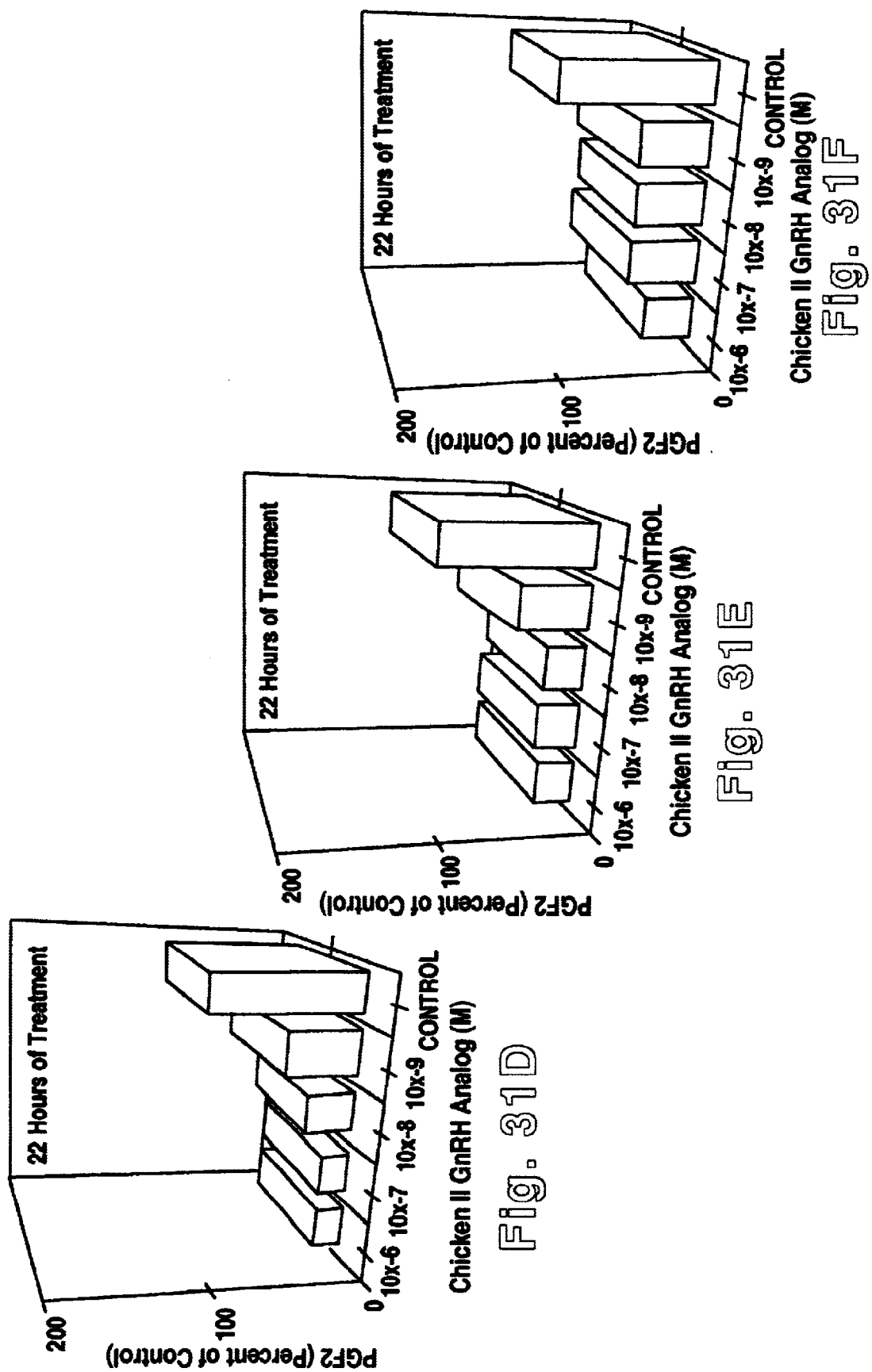

SEQUENCE LISTING

<160> NUMBER OF SEQ ID NOS: 4

<210> SEQ ID NO 1
<211> LENGTH: 30
<212> TYPE: cDNA
<213> ORGANISM: Gallus gallus

<400> SEQUENCE: 1
cagcactggt cccatggctg gtaccctgga           30

<210> SEQ ID NO 2
<211> LENGTH: 10
<212> TYPE: Prt
<213> ORGANISM: Gallus gallus
<220> FEATURE:
<221> NAME/KEY: mat_peptide
<222> LOCATION: Within brain mRNA 121-150, within brain gene 2174-2203.
<223> OTHER INFORMATION: MOD_RES substitution of Gly residue at 10 by
    aza-Gly-NH2, ethylamide or other Gly amide. Xaa represents D-Arg.
    MOD_RES Glu at position 1 is pyroglutamic acid.

<400> SEQUENCE: 2

Glu His Trp Ser His Xaa Trp Tyr Pro Gly
                5                   10

<210> SEQ ID NO 3
<211> LENGTH: 30
<212> TYPE: cDNA
<213> ORGANISM: Salmo salar

<400> SEQUENCE: 3
cagcactggt cttatggctg gctgcctgga           30

<210> SEQ ID NO 4
<211> LENGTH: 10
<212> TYPE: Prt
<213> ORGANISM: Salmo salar
<220> FEATURE:
<221> NAME/KEY: mat_peptide
<222> LOCATION: unknown
<223> OTHER INFORMATION: MOD_RES substitution of Gly residue at 10 with
    aza-Gly-NH2, ethylamide or other Gly amide. Xaa represents D-Arg.
    MOD_RES Glu at position 1 is pyroglutamic acid.

<400> SEQUENCE: 4

Glu His Trp Ser Tyr Xaa Trp Leu Pro Gly
                5                   10

NON-MAMMALIAN GNRH ANALOGS AND USES THEREOF IN REGULATION OF FERTILITY AND PREGNANCY

This is a continuation-in-part patent application based on U.S. patent application Ser. No. 09/419,161 filed Oct. 15, 1999 now U.S. Pat. No. 6,323,179.

FIELD OF THE INVENTION

The present invention relates generally to the field of regulating reproductive function, fertility and pregnancy. More particularly, it concerns the use of unique non-mammalian peptide hormone analogs of GnRH designed to be useful in fertility regulation, post-coital contraception and as a menses-inducing agent and the management of ovarian cyst, polycystic ovarian disease, in vitro fertilization protocols, endometriosis, abnormal uterine bleeding, leiomyomas, abnormal pregnancies, ectopic pregnancies, molar pregnancies, and trophoblastic disease.

BACKGROUND OF THE INVENTION

Before the chemical characterization of the mammalian hypothalamic GnRH, it was realized that hypothalamic substances regulated production of pituitary LH and FSH. Burgus R., Guillemim R 1970 Hypothalamic releasing factors Ann Rev Biochem 39:499–526. Current contraceptive methods are centered on the existing knowledge of GnRH-gonadotropin-ovarian physiology.

The delineation of mammalian GnRH made possible the ability to create methods to detect and quantify this molecule. The human placenta and the chorionic membranes have also been observed to contain a GnRH-like substance. Gibbons J M, Mitnick M, Chieffo V 1975 In vitro biosynthesis of TSH- and LH-releasing factors by the human placenta. Am J Obstet Gynecol 121:127–131. The present investigator has localized, quantified and demonstrated the synthesis of a GnRH-like substance by the human placenta. Siler-Khodr T M, Khodr G S 1978 Luteinizing hormone releasing factor content of the human placenta. Am J Obstet Gynecol 130:216–219; Khodr G S, Siler-Khodr T M 1978 Localization of luteinizing hormone releasing factor (LRF) in the human placenta. Fert Steril 29:523–526; Siler-Khodr T M, Khodr G S 1979 Extrahypothalamic luteinizing hormone releasing factor (LRF): Release of immunoreactive LRF by the human placenta in vitro. Fert Steril 22:294–296; Khodr G S, Siler-Khodr T M 1980 Placental LRF and its synthesis. Science 207:315–317.

The concentration of immunoreactive GnRH-like material in the placenta and maternal blood has been found to vary with gestational age, following a pattern similar to that of hCG. Siler-Khodr T M, Khodr G S, Valenzuela G 1984 Immunoreactive gonadotropin-releasing hormone level in maternal circulation throughout pregnancy. Am J Obstet Gynecol 150:376–379; Sorem K A, Smirkel C B, Spencer D K, Yoder B A, Grayson M A, Siler-Khodr T M 1996 Circulating maternal CRH and GnRH in normal and abnormal pregnancies. Am J Obstet Gynecol 175:912–916. It was also demonstrated that exogenous synthetic mammalian GnRH can stimulate hCG production from human placental explants in vitro, and that the GnRH stimulation of hCG release was a receptor mediated event, since it was specific and could be inhibited by a GnRH antagonist, [N-Ac-Pro, D-p-Cl-Phe,D-Nal(2)]-GnRH. Khodr G S, Siler-Khodr T M 1979 The effect of luteinizing hormone releasing factor (LRF) on hCG secretion Fert Steril 30:301–304; Siler-Khodr T M, Khodr G S 1981 Dose response analysis of GnRH stimulation of hCG releases from human term placenta. Biol Reprod 25:353–358; Siler-Khodr T M, Khodr G S 1979 Extrahypothalamic luteinizing hormone releasing factor (LRF): Release of immunoreactive LRF by the human placenta in vitro. Fert Steril 22:294–296; Siler-Khodr T M, Khodr G S, Vickery B H, Nestor J J, Jr. 1983 Inhibition of hCG, alpha hCG and progesterone release from human placental tissue in vitro by a GnRH antagonist. Life Sci 32:2741–2745. In addition to the inhibition of hCG, progesterone production was dramatically suppressed. The present investigator also observed that hCG response was related to the gestational age of the placenta. Siler-Khodr T M, Khodr G S, Valenzuela G, Rhode J 1986 Gonadotropin-releasing hormone effects on placental hormones during gestation: 1 Alpha-human chorionic gonadotropin, human chorionic gonadotropin and human chorionic somatomammotropin. Biol Reprod 34:245–254. In addition, a gestational age-related action of the GnRH antagonist on the release of hCG and steroids was observed. Siler-Khodr T M, Khodr G S, Rhode J, Vickery B H, Nestor J J, Jr. 1987 Gestational age related inhibition of placental hCG, hCG and steroid hormone release in vitro by a GnRH antagonist. Placenta 8:1–14. Further studies demonstrated a potent action of GnRH on placental prostanoids, again resulting in their inhibition when endogenous chorionic GnRH was the highest. Siler-Khodr T M, Khodr G S, Valenzuela G, Harper J, Rhode J 1986 GnRH effects on placental hormones during gestation. 111 Prostaglandin E, prostaglandin F, and 13, 14-dihydro-15-keto-prostaglandin F. Biol Reprod 35:312–319; Kang I S, Koong M Y, Forman J S, Siler-Khodr T M 1991 Dose-related action of GnRH on basal prostanoid production from the human term placenta. The 38$^{th}$ Annual Meeting of the Society for Gynecologic Investigation (San Antonio) Abstract #310:253 (Abstr.). The GnRH antagonist also inhibited basal prostaglandin production with greater potency than equimolar concentrations of GnRH, and this action was partially reversed by mammalian GnRH. Siler-Khodr T M, Khodr G S, Harper M J, Rhode J, Vickery B H, Nestor J J, Jr. 1986 Differential inhibition of human placental prostaglandin release in vitro by a GnRH antagonist. Prostaglandins 31:1003–1010. A chorionic GnRH was identified by the present investigator to regulate hCG in a paracrine fashion within the human placenta. Siler-Khodr T. M. and G. S. Khodr. 1981. The production and activity of placental releasing hormones. In Fetal Endocrinology. J. Resko and W. Montagna, editors. Academic Press Inc. New York. 183–210; Siler-Khodr, T. M. and G. S. Khodr. 1982 GnRH in the placenta. In role of Peptides and Proteins in Control of Reproduction; D. S. Khindsa and S. M. McCann, editors. Elsevier North Holland, New York. 347–363; Siler-Khodr T M 1983 Hypothalamic-like releasing hormones of the placenta. Clin Perinatol 10:533–566; Siler-Khodr T M 1983 Hypothalamic-like peptides of the placenta. Semin Reprod Endocrinol 1:321–333. These data demonstrated that this paracrine axis is of physiologic significance in cell to cell communication, and not of inconsequential, ectopic, tumor production.

Studies of other investigators have reported on the actions of mammalian GnRH on placental function. The chorionic GnRH axis has also been identified as having an observed feedback interaction for activin, inhibin, follistatin, neurotransmitter, prostaglandin and steroids. Shi L Y, Zhang Z W, Li W X 1994 Regulation of human chorionic gonadotropin secretion and messenger ribonucleic acid levels by follistatin in the NUCC-3 choriocarcinoma cell line. Endocrinology 134:2431–2437; Steele G L, Currie W D, Yuen B H, Jia X C, Perlas E, Luang P C 1993 Acute stimulation of human chorionic gonadotropin secretion by recombinant human activin-A in first trimester human trophoblast. Endocrinology 133:297–303; Li W, Olofsson J I, Jeung E B, Krisinger J, Yuen B H, Leung P C 1994 Gonadotropin-releasing hormone (GnRH) and cyclic AMP positively regulate inhibit subunit messenger RNA levels in human placental cells. Life Sci 55:1717–1724; Petraglia F, Vaughan J, Vale W 1991 Inhibin and activin modulate the release of gonadotropin-releasing hormone, human chorionic gonadotropin, and progesterone from cultured human placental cells. Proc Natl Acad Sci USA 86:5114–5117; Petraglia F, Sawchenko P, Lim A T W, Rivier J, Vale W 1987 Localization, secretion, and action of inhibin in human placenta. Science 237:187–189; Shi C Z, Zhuang L Z 1993 Norepinephrine regulates human chorionic gonadotropin production by first trimester trophoblast tissue in vitro. Placenta 14:683–693; Cemetikic B, Maulik D, Ahmed M S 1992 Opioids regulation of hCG release from trophoblast tissue is mediated by LHRH. Placenta Abstract: 9(Abstr.); Petraglia F, Vaughan J, Vale W 1990 Steroid hormones modulate the release of immunoreactive gonadotropin-releasing hormone from cultured human placental cells. J Chn Endocrinol Metab 70:1173–1178; Haning R V, Jr., Choi L, Kiggens A J, Kuzma D L, Summerville J W 1982 Effects of dibutyryl adenosine 3', 5'-monophosphate, luteinizing hormone-releasing hormone, and aromatase inhibitor on simultaneous outputs of progesterone 17b-estradiol, and human chorionic gonadotropin by term placental explants. J Clin Endocrinol Metab 55:213–218; Petraglia F, Lim A T, Vale W 1987 Adenosine 3', 5-monophsphate, prostaglandin, and epinephrine stimulate the secretion of immunoreactive gonadotropin-releasing hormone from cultured human placental cells. J Clin Endocrinol Metab 65:1020–1025; Harting R V, Jr. Choi L, Kiggens A J, Kuzma D L 1982 Effects of prostaglandin, dibutyryl camp LHRH, estrogen, progesterone, and potassium on output of prostaglandin F2a, 13, 14-dihydro- 15-keto-prostaglandin F2a, hCG, estradiol, and progesterone by placental minces. Prostaglandins 24:495–506; Barnea E P, Feldman D, Kaplan M 1991 The effect of progesterone upon first trimester trophoblastic cell differentiation and human chorionic gonadotropin secretion. Hum Reprod 6:905–909; Barnea E R, Kaplan M 1989 Spontaneous, gonadotropin-releasing hormone-induced, and progesterone-inhibited pulsatile secretion of human chorionic gonadotropin in the first trimester placenta in vitro. J Clin Endocrinol Metab 69:215–217; Branchaud C, Goodyear C, Lipowski L 1983 Progesterone and estrogen production by placental monolayer cultures: Effect of dehydroepiandrosterone and luteinizing hormone-releasing hormone. J Chn Endocrinol Metab 56:761–766; Ahmed N A, Murphy B E 1988 The effects of various hormones on human chorionic gonadotropin production in early and late placental explant cultures. Am J Obstet Gynecol 159:1220–1227; Iwashita M, Watanabe M, Adachi T, Ohira A, Shinozaki Y, Takeda Y, Sakamoto S 1989 Effect of gonadal steroids on gonadotropin-releasing hormones stimulated human chorionic gonadotropin release by trophoblast cells. Placenta 10:103–112; Haning R V, Jr., Choi L, Kiggnes A J, Kuzma D L, Summerville J W 1982 Effects of dibutyryl cAMP, LHRH, and aromatase inhibitor on simultaneous outputs of prostaglandin F2a, and 13, 14-dihydro- 15-keto-prostaglandin F2a by term placental explants. Prostaglandins 23:29–40; Wilson E, Jawad M 1980 Luteinizing hormone-releasing hormone suppression of human placental progesterone production. Fert Steril 33:91–93. These and other studies established the presence of this paracrine axis, including a negative feedback loop for progesterone and estrogen, similar to that of the hypothalamic-pituitary-gonadal axis. This placental axis, multiple paracrine axes for GnRH and other hypothalamic-like releasing and inhibiting activities have now been defined in the placenta, eye, pancreas, ovary, brain, bone, etc., and are now recognized as essential to normal physiologic functions. Siler-Khodr, T. M. 1992. The Placenta: Part IV-Function of the Human Placenta. In Neonatal and Fetal Medicine. R. A. Polin and W. W. Fox, editors. W. B. Saunders Co. Philadelphia, Pa. 74–86; Youngblood W W, Humni J, Kizer J S 1979 TRH-like immunoreactivity in rat pancreas and eye, bovine and sheep ideals, and human placenta: Non-identity with synthetic Pyroglu-His-Pro-NH2 (TRH). Brain Res 163: 101–110; Dubois M P 1975 Inmunoreactive somatostatin is present in discrete cells of the endocrine pancreas. Proc Natl Acad Sci USA 72:1340–1343; Adashi. E. Y. 1996. The Ovarian Follicular Apparatus. In Lippincott-Raven Publishers. E. Y. Adashi. J. A. Rock, and Z. Rosenwaks, editors. Lippincott-Raven Publishers, Philadelphia. 17–40.

Recent studies have led to the isolation and characterization of a GnRH gene in the placenta, which is transcribed to a mRNA identical to that in the hypothalamus with the exception of the inclusion of the first intron and a very long first exon. Radovick S, Wondisford F E, Nakayama Y, Yamada M, Cutler G B, Jr., Weintraub B D 1990 Isolation and characterization of the human gonadotropin-releasing hormone gene in the hypothalamus and placenta. Mol Endocrinol 4:476–480; Adelman J P, Mason A J, Hayflick J S, Seeburg P H 1986 Isolation of the gene and hypothalamic cDNA for the common precursor of gonadotropin-releasing hormone and prolactin release-inhibiting factor in human and rat. Proc Natl Acad Sci USA 83:179–183; Seebirg P H, Adelman J P 1984 Characterization of cDNA for precursor of human luteinizing hormone releasing hormone. Nature 311:666–668. The message has been localized to the syncytio- and cytotrophoblast, as well as the stroma of the placenta, and is present in higher concentrations during the first half of pregnancy. Duello T M, Tsai S J, Van Ess P J 1993 In situ demonstration and characterization of pro gonadotropin-releasing hormone messenger ribonucleic acid in first trimester human placentas. Endocrinology 133:2617–262–3; Kelly A C, Rodgers A, Dong K W, Barrezueta N X, Blum M, Roberts J L 1991 Gonadotropin-releasing hormone and chorionic gonadotropin gene expression in human placental development DNA Cell Biol 10:411–421. Multiple transcription sites have been identified for the GnRH gene in reproductive tissues, including the placenta. Dong K W, Yu K L, Roberts J L 1993 Identification of a major up-stream transcription start site for the human pro gonadotropin-releasing hormone gene used in reproductive tissues and cell lines. Mol Endocrinol 7:1654–166; Dong K W, Duval P, Zeng Z, Gordon K, Williams R F, Hodgen G D, Jones G, Kerdelhue B, Roberts J L 1996 Multiple transcription start sites for the GnRH gene in rhesus and cynomolgus monkeys: a non-human primate model for studying GnRH gene regulation. Mol Cell Endocrinol 117:121–130; Dong K W, Yu K L, Chen Z G, Chen Y D, Roberts J L 1997 Characterization of multiple promoters directing tissue-specific expression of the human gonadotropin-releasing hormone gene. Endocrinology 138:2754–2762. Steroid regulatory sites on the promoter have also been identified. Chandran U R, Attardi B, Friedman R, Dong K W, Roberts J L, DeFranco D B 1994 Glucocorticoid receptor-mediated repression of gonadotropin-releasing hormone promoter activity in GTI hypothalamic cell lines. Endocrinology 134:1467–1474; Dong K W, Chen Z G, Cheng K W, Yu K L 1996 Evidence for estrogen receptor-mediated regulation of human gonadotropin-releasing hormone promoter activity in human placental cells. Mol Cell Endocrinol 117:241–246. The functionality of this promoter is supported by showing that GnRH mRNA can be regulated by steroids. Joss J M, King J A, Millar R P 1994 Identification of the molecular forms of and steroid hormone response to gonadotropin-releasing hormone in the Australian lungfish Neoceratodus forsteri. Gen Comp Endocrinol 96:392–400; Montero M, Le Belle N, King J A, Millar R P, Dufour S 1995 Differential regulation of the two forms of gonadotropin-releasing hormone (mGnRH and chicken GnRH-II) by sex steroids in the European female silver eel (*Anguilla anguilla*). Neuroendocrinology 61:525–535; Ikeda M, Taga M, Sakakibara H, Minaguchi H, Ginsburg E, Vonderhaar B K 1996 Gene expression of gonadotropin-releasing hormone in early pregnant rat and steroid hormone exposed mouse uteri. J Endocrinol Invest 19:708–713; Gothilf Y, Meiri I, Elizur A, Zohar Y 1997 Preovulatory changes in the levels of three gonadotropin-releasing hormone-encoding messenger ribonucleic acids (mRNAs), gonadotropin. B-subunit mRNAs plasma gonadotropin, and steroids in the female gilthead seabream, Sparus aurata, Biol Reprod 57:1145–1154.

It has previously been accepted that only non-mammalian vertebrates have multiple forms of GnRH in the same species. However, Dellovad, et al. and in 1994, King et al. have described chicken II GnRH in shew, mole and bat brain, thus demonstrating that two different isomers of GnRH existed in the mammal. Dellovade T L, King J A, Millar R P, Rissman E F 1993 Presence and differential distribution of distinct forms of immunoreactive gonadotropin-releasing hormone in the musk shrew brain. Neuroendocrinology 58:166–177; King J A, Steneveld A A, Curlewis J D, Rissman E F, Millar R P 1994 Identification of chicken GnRH II in brains of inetatherian and early-evolved eutherian species of mammals. Regul Pept 54:467–477. Therefore, the hypothesis of more than one form of GnRH in the human placenta was considered dubious. Chicken II GnRH has now been characterized in the guinea pig and in the human brain. Jimenez-Linan M, Rubin B S, King J C 1997 Examination of guinea pig luteinizing hormone-releasing hormone gene reveals a unique decapeptide and existence of two transcripts in the brain. Endocrinology 13 8:4123–4130; Lescheid D, Terasawa E, Abler L A, Urbanski H F, Warby C M, Millar R P, Sherwood N M 1997 A second form of gonadotropin-releasing hormone (GnRH) with characteristics of chicken GnRH-II is present in the primate brain. Endocrinology 138:1997. Separate genes for chicken II GnRH and mammalian GnRH have also been described. White S A, Bond C T, Francis R C, Kasten T L, Fernald R D, Adelman J P 1994 A second gene for gonadotropin-releasing hormone: cDNA and expression pattern in the brain. Proc Natl Acad Sci USA 91:1423–1427; Lin X W, Peter R E 1997 Cloning and expression pattern of a second [His5Trp7Tyr8] gonadotropin-releasing hormone (chicken GnRH-H-11) mRNA in goldfish; evidence for two distinct genes. Gen Comp Endocrinol 107:262–272.

The GnRH receptor in the placenta has not been characterized as fully as the GnRH receptor in the pituitary. Sealfon S C, Weinstein H, Millar R P 1997 Molecular mechanism of ligand interaction with the gonadotropin-releasing hormone receptor. Endocr Rev 18:180–205; Karten M J, Rivier J E 1986 Gonadotropin-releasing hormone analog design. Structure-function studies toward the development of agonists and antagonists: Rationale and perspective. Endocr Rev 7:44–66. It is known that two populations of placental GnRH receptors exist, one having a Ka of $10^{-9}$M and the other with a significantly lower affinity of $10^{-7}$M. In addition, superagonist or antagonist for the pituitary GnRH receptor shows very different affinity for the placental receptor. Escher E, Mackiewicz Z, Lagace G, Lehoux J, Gallo-Payet N, Bellabarba D, Belisle S 1988 Human placental LHRH receptor: Agonist and antagonist labeling produces differences in the size of the non-denatured, solubilize receptor; J Recept Res 8:391–405; Bramley T A, McPhie C A, Menzies G S 1992 Human placental gonadotropin-releasing hormone (GnRH) binding sites: Characterization, properties and ligand specificity. Placenta 12:555–581. Other isomers of GnRH, such as salmon GnRH and chicken II GnRH, have a much greater affinity for the placental receptor, yet bind with a lesser affinity to the human pituitary receptor. Bramley T A, McPhie C A, Menzies G S 1992 Human placental gonadotropin-releasing hormone (GnRH) binding sites: Characterization, properties and ligand specificity. Placenta 12:555–581. These data demonstrate the existence of a specific placental receptor for GnRH-like molecules, yet the true ligand for this receptor is not known.

In amphibians, a chicken II GnRH receptor as well as a mammalian GnRH receptor has been shown. The specificity and evolutionary aspects of the GnRH receptor has been studied in many species. Mammalian GnRH has been reported to be active in many vertebrate classes. Other GnRHs, such as chicken II GnRH and salmon GnRH, have reduced affinity for the mammalian pituitary receptor.

GnRH receptor activity, as well as the mRNA for the GnRH receptor, varies throughout gestation in the human placenta. Bramley T A, McPhie C A, Menzies G S 1994 Human placental gonadotropin-releasing hormone (GnRH) binding sites: 111. Changes in GnRH binding levels with stage of gestation. Placenta 15:733–745; Lin L S, Roberts V J, Yen S S 1997 Expression of human gonadotropin-releasing hormone receptor gene in the placenta and its functional relationship to human chorionic gonadotropin secretion. J Clin Endocrinol Metab 80:580–585. The receptor is greatest in early gestation and appears to be down regulated by 12–20 weeks. While the receptor is again detectable in term placentas, the mRNA (using a GnRH decapeptide probe and in situ hybridization methodology) was undetectable at this state of gestation. Bramley T A, McPhie C A, Menzies G S 1994 Human placental gonadotropin-releasing hormone (GnRH) binding sites: 111. Changes in GnRH binding levels with stage of gestation. Placenta 15:733–745; Lin L S, Roberts V J, Yen S S 1997 Expression of human gonadotropin-releasing hormone receptor gene in the placenta and its functional relationship to human chorionic gonadotropin secretion. J Clin Endocrinol Metab 80:580–585. This pattern of receptor activity is consistent with the concentration of GnRH-like material in placental tissue and maternal blood throughout gestation, and supports the hypothesis that chorionic GnRH may down-regulate its chorionic receptors, as can mammalian GnRH, and its analogs at the pituitary level. Siler-Khodr T M, Khodr G S, Valenzuela G 1984 Immunoreactive gonadotropin-releasing hormone level in maternal circulation throughout pregnancy. Am J Obstet Gynecol 150:376–379; Siler-Khodr T M, Khodr G S 1978 Luteinizing hormone releasing factor content of the human placenta. Am J Obstet Gynecol 130:216–219. Studies by the present investigator and those of Barnea et al, have demonstrated competitive inhibition by GnRH antagonist. Siler-Khodr T M, Khodr G S, Vickery B H, Nestor J J, Jr. 1983 Inhibition of hCG, alpha hCG and progesterone release from human placental tissue in vitro by a GnRH antagonist. Life Sci 32:2741–2745; Siler-Khodr T M, Khodr G S, Harper M J, Rhode J, Vickery B H, Nestor J J, Jr. 1986 Differential inhibition of human placental prostaglandin release in vitro by a GnRH antagonist. Prostaglandins 31:1003–1010; Barnea E R, Kaplan M, Naor Z 1991 Comparative stimulatory effect of gonadotropin releasing hormone (GnRH) and GnRH agonist upon pulsatile human chorionic gonadotropin secretion in superfused placental explants: reversible inhibition by a GnRH antagonist. Hum Reprod 6:1063–1069. Other studies of Szilagyi et al. and Currie et al. indicate that mammalian GnRH agonist can down-regulate the placental GnRH receptor. Szilagyi A, Benz R, Rossmanith W G 1992 The human first-term placenta in vitro: regulation of hCG secretion by GnRH and its antagonist. Gynecol Endocrinol 6:293–300; Currie W D, Setoyarna T, Lee P S, Baimbridge K G, Church J, Yuen B H, Leung P C 1993 Cytosolic free Ca2+ in human syncytiotrophoblast cells increased by gonadotropin-releasing hormone. Endocrinology 133:2220–2226. In addition, the demonstration that the placental GnRH receptor can be up regulated in cell cultures by estradiol supports the hypothesis that this receptor is functional in the regulation of placental hormonogenesis. Barnea E R, Kaplan M, Naor Z 1991 Comparative stimulatory effect of gonadotropin releasing hormone (GnRH) and GnRH agonist upon pulsatile human chorionic gonadotropin secretion in superfused placental explants: reversible inhibition by a GnRH antagonist. Hum Reprod 6:1063–1069; Bliatacharya S, Chaudhary J, Das C 1992 Responsiveness to gonadotropin releasing hormone of human term trophoblast cells in vitro: induction by estradiol. Biochem Int 28:363–371.

Another factor that regulates a hormone's activity is its metabolism. The enzyme that degrades GnRH differs during pregnancy from the enzyme that degrades GnRH in the pituitary or the blood of non-pregnant individuals. In placental tissue, the primary enzymatic activity for the degradation of GnRH is chorionic peptidase-1 (C-ase-1), a post-proline peptidase. Siler-Khodr T W I, Kang I S, Jones M A, Harper M J K, Khodr G S, Rhode J 1989 Characterization and purification of a placental protein that inactivates GnRH, TRH and Angiotensin 11. Placenta 10:283–296; Kang I S, Siler-Khodr T M 1992 Chorionic peptidase inactivates GnRH as a post-proline peptidase. Placenta 13:81–87. C-ase-1 is a glycoprotein with a molecular weight of 60,000. It acts as a post-proline peptidase, and is inhibited by bacitracin, para-amino-benzamidine, acetopyruvate and certain cations. Siler-Khodr T W I, Kang I S, Jones M A, Harper M J K, Khodr G S, Rhode J 1989 Characterization and purification of a placental protein that inactivates GnRH, TRH and Angiotensin 11. Placenta 10:283–296. GnRH is actively degraded by C-ase-1 at neutral pH, having a Km of $10^{-8}$M. Kang I S, Gallwitz J, Guzman V, Siler-Khodr T M 1990 Definition of the enzyme kinetics and optimal activity of chorionic peptidase-1. The $23^{rd}$ Annual Meeting of the Society for the Study of Reproduction (Vancouver) (Abstract #311):144(Abstr.). Using immunofluorescent methodology, C-ase-1 has been localized by the present inventor in the cytoplasm of the syncytiotrophoblast and syncytial buds. It is secreted into maternal blood, where GnRH is not stable without specific inhibitors of this post-proline peptidase. Benuck M, Marka N 1976 Differences in the degradation of hypothalamic releasing factors by rat and human serum. Life Sci 19:1271–1276. C-ase-1 is present in very high concentrations, and accounts for virtually al GnRH degrading activity in the placenta under physiological conditions.

These in vitro studies support the hypothesis of the specific, receptor-mediated and enzyme-regulated action of mammalian GnRH on placental hormonogenesis, and demonstrate the paracrine effects and feedback interactions for numerous intrauterine hormones interacting with chorionic GnRH. Further studies on the action of mammalian GnRH and its analogs in vivo have also demonstrated these paracrine interactions for chorionic GnRH-like activity and numerous other chorionic hormones, and have established the physiologic role of GnRH in the maintenance of normal pregnancy. Siler-Khodr, T. M. 1993. Luteinizing Hormone Releasing Hormone (LHRH) and the Placenta and Fetal Membranes. In Molecular Aspects of Placental and Fetal Membrane Autocoids. G. E. Rice and S. P. Brennecke, editors. CRC Press, Inc. Ann Arbor. 339–350; Petraglia F, Calza L, Garuti G C, Giardino L, De Ramundo B M, Angioni S 1990 New aspects of placental endocrinology. J Endocrinol Invest 65:262–267.

Recent studies demonstrate that the number of GnRH receptors and mRNA for the GnRH receptor in the placenta varies in a pattern similar to that of hCG. Duello T M, Tsai S J, Van Ess P J 1993 In situ demonstration and characterization of pro gonadotropin-releasing hormone messenger ribonucleic acid in first trimester human placentas. Endocrinology 133:2617–262–3; Lin L S, Roberts V J, Yen S S 1997 Expression of human gonadotropin-releasing hormone receptor gene in the placenta and its functional relationship to human chorionic gonadotropin secretion. J Clin Endocrinol Metab 80:580–585. Other investigators have shown steroid responsive elements in the placental GnRH gene, providing further evidence for the physiologic regulation of placental GnRH-like activity. Dong K W, Chen Z G, Cheng K W, Yu K L 1996 Evidence for estrogen receptor-mediated regulation of human gonadotropin-releasing hormone promoter activity in human placental cells. Mol Cell Endocrinol 117:241–246. Petraglia et al. has described the pulsatile release of a GnRH-like substance, which has a specific pulse frequency, amplitude and duration, with increased amplitude during early gestation. Petraglia F, Genazzani A D, Aguzzoli L, Gallinelli A, de Vita D, Caruso A, Genazzani A R 1994 Pulsatile fluctuations of plasma-gonadotropin-releasing hormone and corticotropin-releasing factor levels in healthy pregnant women. Acta Obstet Gynecol Scand 73:284–289. Other investigators using rhesus monkey embryos have demonstrated the secretion of a GnRH-like substance by the peri-implantation embryo, which precedes the secretion of chorionic gonadotropin. Seshagiri PB, Terasawa E, Hearn J P 1994 The secretion of gonadotropin-releasing hormone by peri-implantation embryos of the rhesus monkey: comparison with the secretion of chorionic gonadotropin. Hum Reprod 9:1300–1307

Other investigators have shown that administration of high doses of mammalian GnRH, its agonistic analogs or antibodies, to pregnant baboons and monkeys effects a sharp decrease of C G production and progesterone, which in most cases leads to termination of pregnancy. Gupta S K, Singh M 1985 Characteristics and bioefficacy of monoclonal anti-gonadotropin releasing hormone antibody. Am J. Repro Immunol Microbiol 7:104–108; Das C, Gupta S K, Talwar G P 1985 Pregnancy interfering action of LHRH and anti-LHRH. J. Steroid Biochem 23:803–806; Hodges J K, Hearn J P 1977 Effects of immunization against luteinizing hormone releasing hormone on reproduction of the marmoset monkey *Callithrix jacchus*. Nature 265:746–748; Vickery B H, McRae G I, Stevens V C 1981 Suppression of luteal and placental function in pregnant baboons with agonist analogs of luteinizing hormone-releasing hormones. Fert Steril 36:664–668; Das C, Talwar G P 1983 Pregnancy-terminating action of a luteinizing hormone-releasing hormone agonist D-Ser(But)6desGly10ProEA in baboons. Fert Steril 39:218–223; Rao A, Moudgal N 1984 Effect of LHRH injection on serum chorionic: gonadotropin levels in the pregnant bonnet monkey (*Macaca radiata*). Obstet Gynecol 12:1105–1106; Rao A J, Chakraborti R, Kotagi S G, Ravindranath N, Moudgal N R 1985 Effect of LHRH agonists and antagonists in male and female bonnet monkeys (*Macaca Radiata*). J. Steroid Biochem 23:807–809. Interruption of pregnancy was most consistently observed when these mammalian GnRH analogs were administered around the time of or shortly following implantation. In pregnant women, administration of low doses of mammalian GnRH does not significantly change circulating hCG. Tamada T, Akabori A, Konuma S, Araki S 1976 Lack of release of human chorionic gonadotropin by gonadotropin-releasing hormone. Endocrinol Jap 23:531–533; Perez-Lopez FR, Robert J, Teijeiro J 1984 Prl, TSH, FSH, B-hCG and oestriol responses to repetitive (triple) LRH/TRH administration in the third trimester of human pregnancy. Acta Endocrinol 106:400–404. However, this finding was dose and gestational age related. Egyed J, Gati I 1985 Elevated serum hCG level after intravenous LH-RH administration in human pregnancies. Endocrinol Exp 19:11–15; Iwashita M, Kudo Y, Shinozaki Y, Takeda Y 1993 Gonadotropin-releasing hormone increases serum human chorionic gonadotropin in pregnant women. Endocrine Journal 40:539–544.

A recent study of Devreker et al. reports that the use of long-acting mammalian GnRH analogs in IVF, impaired the implantation rate. Devreker F, Govaerts I, Bertrand E, Van den Bergh M, Gervy C, Englert Y 1996 The long-acting gonadotropin-releasing hormone analogues impaired the implantation rate. Fert Steril 65:122–126. While these analogs have proven to be generally nontoxic, long-term chronic use has been associated with a hypo-estrogenic state. Accidental administration of mammalian GnRH analogs during early pregnancy has been reported, with varied outcomes. Siler-Khodr, T. M. 1994. Potentials for embryo damage of GnRH analogs. In Ovulation Induction: Basic Science and Clinical Advances. M. Filicor and C. Flamigni, editors Elsevier Science B. V. Amsterdam. 279–306. Generally, pregnancy outcomes appeared unaffected, but increased cases of spontaneous abortion and pre-term labor have also been observed. The varied outcomes may reflect the different doses and protocols of administration of these mammalian GnRH analogs, as well as the different analogs employed. For analogs that can be rapidly metabolized by the chorionic tissues, little effect, if any, would be anticipated. In addition, the affinity for the placental receptor for many of these mammalian GnRH analogs is greatly reduced as compared to the pituitary receptor's affinity and they are degraded by the placental enzymes. In those cases, little chorionic effect would be observed.

SUMMARY OF THE INVENTION

The present invention, in a general and overall sense, relates to novel pharmaceutical preparations that include non-mammalian gonadotropin releasing hormone (GnRH) analogs specifically designed to bind human chorionic GnRH receptor, ovarian GnRH receptors, fallopian tube and uterine tissue GnRH receptors. These analogs are designed to be resistant to degradation by post-proline peptidases and endopeptidases. Post-proline peptidases have been found to specifically and very actively degrade GnRH in chorionic, ovarian, tubal, and uterine tissues and maternal blood.

The non-mammalian GnRH analogs of the present invention may act either as a superagonist at the placental, ovarian, tubal, or uterine receptor leading to its down regulation, or as a pure antagonist of chorionic, ovarian, tubal, or uterine GnRH at the GnRH receptor. The down-regulation or antagonism of endogenous chorionic GnRH will provide for a reduction in human chorionic gonadotropin (hCG) production. This will also provide a reduction in ovarian and placental steroidogenesis. In addition, a direct ovarian luteolytic action may be expected to occur. If trophoblastic and/or ovarian function is jeopardized, premature luteolytic action will occur. If trophoblastic and/or ovarian function is jeopardized, premature luteolysis of the corpus luteum will occur and menses will ensue. Thus, such an agent may be used as a post-coital, luteolytic agent, leading to the induction of menses. Until now, no such GnRH analog has been found to be active during pregnancy or at the ovary. In addition, maturation of the egg and the process of ovulation, as well as the process of fertilization and maturation of the fertilized egg, will be affected. The activity of the fallopian tube will be affected altering transport and maturation of the morula during transit. In addition, uterine hormone and cell functions will be affected. PGE production is decreased which will lead to decreased vasofunction and vasodilation. The uterine environment will be made hostile to implantation of the blastocyst or the maintenance of pregnancy. The regression of uterine endometrial tissue will result.

The inventor has designed non-mammalian GnRH analogs that are active as luteolytic, menses-inducing agents and/or post-coital contraceptives. The chorionic, ovarian, and uterine receptor binding activity of these particularly designed non-mammalian GnRH analogs has also been characterized in the development of the present analogs. The analogs of the invention may be further defined as resistant to enzymatic degradation by ovarian, uterine, and placental enzymatic activity by specific endopeptidase and post-proline peptidase, such as C-ase-1. The agonist and antagonists with the greatest receptor affinity and tissue stability are expected to effectively inhibit hCG and progesterone release from human placenta and ovary, and PGE production from fallopian tubes and uterine tissues. The non-mammalian GnRH analogs of the invention may be used to inhibit placental production of hCG and progesterone, and have a direct effect on steroidogenesis at the ovary and prostaglandins in the fallopian tubes and uterus. The effects of the analogs may thus be used to induce luteolysis and menses-induction and anti-implantation, anti-pregnancy activity.

In one aspect, the invention provides methods of designing analogs of non-mammalian GnRH having increased activity in the chorionic tissues. Methods to inhibit hCG production by placental tissues, that in turn provide a reduction of ovarian and placental steroidogenesis, i.e., luteolysis and menses-induction, are provided in another aspect of the present invention. The use of these analogs directly on the ovary is yet another particular embodiment of the invention. The use of these analogs to directly affect fallopian tube function is yet another embodiment of the invention. The use of these analogs to alter uterine prostaglandin production is yet another embodiment of the invention. The analogs of the invention may be used in pharmaceutical preparations as a menses-regulating agent, a contraceptive, or as an abortifacient.

Non-mammalian GnRH analogs that are superagonist or antagonists at the trophoblastic/placental, ovarian, tubal and/or uterine level constitute yet other embodiments of the invention. Such a non-mammalian analog would provide for the inhibition of steroidogenesis during pregnancy, acting both as an anti-chorionic and anti-luteal agent by inhibiting steroidogenesis or at the tubal or uterine level act to inhibit PGE production leading to menses induction. The non-mammalian GnRH analogs of the invention thus comprise peptides that are capable of specifically binding the chorionic, ovarian, fallopian tubes and/or uterine GnRH receptors with high affinity, are resistant to degradation by endopeptidase and post-proline peptidase activity and effect either a down-regulation of the GnRH receptor or act as a true antagonist, inhibiting hCG production and ovarian and placental steroidogenesis or directly inhibiting ovarian steroidogenesis and/or inhibiting tubal and/or uterine prostaglandin production. In other embodiments, the invention comprises a salmon sequence (SEQ ID NO: 4) or chicken II GnRH sequence (SEQ ID NO: 2), which both show greater affinity for the placental, ovarian and uterine receptor than mammalian GnRH, that are modified at the C-terminal. An ethylamide or aza-Gly$^{10}$-NH$_2$ substitution may be used, making the sequence more stable in chorionic, ovarian, tubal, and uterine tissues and maternal blood. In other embodiments the GnRH analog sequence is substituted at the 6-position with a D-Arg, or other D-amino acid. In yet other embodiments, both of these modifications are made to the GnRH analog peptide sequence. The chicken II or salmon backbone and the substitutions of the molecule are expected to enhance the binding of the molecule, while at the same time the substitutions are designed to inhibit any of the peptidases that are present in blood. These analogs are expected to have increased binding to the placental, ovarian, fallopian tube, or uterine receptor and increased metabolic stability. The placental receptor binding, placental metabolic degradation and the biological activity for hCG, progesterone and prostaglandin production was studied for each of these specially designed non-mammalian GnRH analogs, and compared to closely related pituitary mammalian GnRH analogs (Buserilin, Tryptolein, Leuprolide, etc.). These studies demonstrated greater stability of the non-mammalian GnRH analogs, binding affinity and bioactivity compared to the mammalian GnRH analogs examined. The ovarian receptor binding, ovarian metabolic degradation, and the biological activity for progesterone production were studied for each of the specially designed non-mammalian GnRH analogs, and compared to closely related pituitary mammalian GnRH analogs. These studies demonstrated greater stability, binding affinity, and bioactivity of the non-mammalian GnRH analogs compared to the mammalian GnRH analogs examined. The uterine receptor binding and biological activity for the prostaglandin E production were studied for these specially designed non-mammalian GnRH analogs and compared to closely related pituitary mammalian GnRH analogs. These studies demonstrated greater binding affinity and bioactivity on the non-mammalian GnRH analogs compared to the mammalian GnRH analogs examined.

In other embodiments, the invention provides non-mammalian GnRH analogs with enhanced activity within the intrauterine tissues, as well as a method for regulating hCG production and thus progesterone production during pregnancy. This activity of these analogs may be useful in the management of threatened abortion or the induction of abortions, or in the management of abnormal pregnancies, ectopic pregnancies, molar pregnancies, or trophoblastic disease. These non-mammalian GnRH analogs also have a direct action on endometrial tissue. This activity may prove beneficial in treatments for endometriosis, abnormal uterine bleeding, and leiomyomas. These non-mammalian GnRH analogs also have a direct action at the ovary. Such action may prove useful in the manufacture of treatments for ovarian conditions, such as polycystic ovarian disease, ovarian cysts, atresia, used in in vitro fertilization programs or for the induction of luteolysis. Luteolysis may be affected by a dual mechanism i.e., through inhibition of hCG and thus reduction of ovarian steroidogenesis and/or direct inhibition of ovarian steroidogenesis. This will be useful to induce menses and as a contraceptive.

It is envisioned that these analogs will be administered intra-nasally, orally, intramuscularly, intrauterine or vaginally. However, virtually any mode of administration may be used in the practice of the invention. Treatment with these analogs may require one to three days of active non-mammalian GnRH analog when used as a post coital contraceptive. As a monthly contraceptive, the placebo is envisioned to start on the first day of menses and continue for approximately 13 days, then the analog would be given days 13 through 28, or less to suppress luteal and/or endometrial function and to induce menses. This could be repeated monthly.

Numerous IVF protocols now routinely use mammalian GnRH analogs for ovulation timing and have been shown to be nontoxic, even after weeks of administration. Long-term therapies with mammalian GnRH analogs have been associated with a hypoestrogenic state, but in the envisioned modes of administration, exposure would not exceed three days to two weeks. The effect on the pituitary GnRH receptor is expected to be minimal with these non-mammalian GnRH analogs and with this short duration of treatment, the menstrual cycle may not be altered. Thus, the limited time of exposure in the late luteal phase and the specific receptor activity of these analogs make it less likely to interfere with reproductive cyclicity and/or normal physiology. The design of the present non-mammalian analogs considers the specific metabolism of GnRH at extra-pituitary tissues, such as the ovary, fallopian tubes, uterus, and placenta and during pregnancy in maternal blood.

Another embodiment of the invention provides non-mammalian GnRH analogs that are resistant to degradation by post-proline peptidases and endopeptidases. This analog will bind the chorionic, ovarian, tubal, and uterine GnRH receptor or non-mammalian GnRH with high affinity so to first stimulate then down-regulate the receptor to displace the endogenous GnRH-like activity and block its action.

In another aspect, the invention provides more potent non-mammalian GnRH analogs that will specifically bind to the placental, ovarian, tubal or uterine GnRH receptor. In addition, analogs will be provided that are stable in maternal circulation and in the blood of non-pregnant individuals. It is also anticipated that these analogs will be biologically active in chorionic tissues, at the ovary, at the fallopian tube, and at the uterus in the regulation of hormonogenesis that will affect the maintenance of pregnancy and/or the receptivity of the uterus for implantation. Due to the specificity of these analogs and their relatively short half-life, the present invention provides non-mammalian GnRH analogs.

Still in another embodiment it is expected that the human may contain another GnRH defined as salmon GnRH which contains the sequence or a degenerate variant of Salmo salar as well as other species which include the pacific salmon (*Oncorhynchus nerka*), the seabass (Dicentrarchus labrax), and the goldfish (*Carassius auratus*).

Other proline-containing peptides compete for post-proline peptidase activity, such as angiotensin II, and to a lesser extent, thyrotropin releasing hormone and reduced oxytocin. Siler-Khodr T M, Kang I S, Jones M A, Harper M J K, Khodr G S, Rhode J 1989 Characterization and purification of a placental protein that inactivates GnRH, TRH and Angiotensin 11. Placenta 10:283–296; Siler-Khodr T M, Grayson M, Pena A, Khodr T 1997 Definition of enzyme specificity of chorionic peptidase-1 for GnRH, TRH, oxytocin and angiotensin 11. J Soc Gynecol Invest 4: 129A (Abstr.). The existing mammalian GnRH analogs are also proline-containing molecules. Since human pituitary and blood contain an enzymatic activity that degrades GnRH at the 5–6 position, not at the 9–10 position, the present non-mammalian GnRH analogs have been designed to inhibit the former enzymatic activities, and have substitutions in the 5–6 position of the molecule. Benuck M, Marka N 1976 Differences in the degradation of hypothalamic releasing factors by rat and human serum. Life Sci 19:1271–1276. Some of the analogs also have a substitution at the 10 position with an ethylamide which is only a weak inhibitor of the post-proline peptidase. The present analogs are therefore, resistant to degradation at the pituitary or in the blood of non-pregnant individuals, but not the ovary, fallopian tube, uterus, or placenta or in maternal blood. Substitution of the Gly10-$NH_2$ with ethylamide is only slightly effective at the placenta, fallopian tube, uterus, or ovary, but the even more potent aza-$Gly^{10}$-$NH_2$, inhibits degradation by post-proline peptidase. Zohar Y, Goren A, Fridkin M, Elhanati E, Koch Y 1990 Degradation of gonadotropin-releasing hormones in the gilthead seabream, *Sparus aurata*. 11. Cleavage of native salmon GnRH, mammalian LHRH, and their analogs in the pituitary, kidney, and liver. Gen Comp Endocrinol 79:306–319.

The stability of the present non-mammalian analogs in the presence of C-ase-1 and ovarian tissues was also examined. The degradation of four of these analogs was examined using a competitive inhibition assay for GnRH . While replacement of $Gly^{10}$-$NH_2$ with ethylamide made each of these GnRH analogs more resistant to degradation, some of the analogs still effected a substantial competition with GnRH demonstrating that they could be degraded. Of four ethylamides studied, des-$Gly^{10}$-GnRH-ethylamide, the des-$Gly^{10}$, D-$Leu^6$-GnRH-ethylamide, or Buserilin, each were potent competitive inhibitors of GnRH degradation by C-ase-1. The less active an analog is as a competitor for GnRH degradation by C-ase-1, the more stable that analog will be in the ovarian, endometrial, and chorionic tissues and in maternal blood. Thus, the existing mammalian GnRH analogs commonly used in medicine can be degraded in the ovarian, endometrial, and chorionic tissues and in maternal blood.

The findings of inhibition of placental, ovarian, and uterine function can be explained by recognizing that the decapeptide sequence for mammalian GnRH is not the only active GnRH sequence in ovarian, fallopian tube, uterine, and chorionic GnRH. Substantial data exists that in these tissues that there is a receptor and that there is a GnRH of which the chemical nature is not identical to mammalian GnRH. Postulating that a different ovarian, fallopian tube, uterine, or chorionic GnRH from the mammalian GnRH exists, and that there is an ovarian, fallopian tube, uterine, or placental receptor that prefers this ovarian, tubal, uterine, or chorionic GnRH, explains the biphasic response of placental hormones to mammalian GnRH. Mammalian GnRH acts as a partial agonist of chorionic GnRH. When receptors are available, it acts as an agonist of ovarian, tubal, uterine, or chorionic GnRH. When ovarian, tubal, uterine, or placental receptors are low or occupied, mammalian GnRH competes with the more potent chorionic GnRH resulting in an antagonistic action.

GnRH-like substances have been found by the present inventor to be decreased at mid-pregnancy in women who later have pre-term labor, and increased in those with post term deliveries. In more recent studies, a GnRH binding substance has been demonstrated in their circulation and in these cases hCG was abnormally reduced and pregnancy loss was observed. Thus, the current studies of GnRH-like substance production during pregnancy indicate that chorionic GnRH is of significance to the maintenance of normal pregnancy.

Mammalian GnRH analogs, ZOLADEX™ (Goserelin acetate) and Organon 30276, were administered to pregnant baboons via mini-pump on days 14 through 21 post ovulation. The hormonal release and pregnancy outcome was compared to saline treated controls. CG and progesterone decreased, and in most animals pregnancy outcomes were jeopardized. However, using these analogs, abortions were not consistently effected, except for the 100 mg-7 day regiment of the Organon antagonist. In a dose-response saline-controlled study using very high doses of mammalian GnRH analog, a small stimulation of hCG in very early pregnancy was observed by the present inventor. However, an inhibition of hCG and progesterone was observed by 12 weeks of pregnancy when chorionic GnRH is maximal. Further studies with these newly designed non-mammalian GnRH analogs having enhanced receptor activity and ovarian, endometrial, and/or chorionic stability promise to provide a much more potent action.

The present inventor has found that certain non-mammalian GnRH analogs can act on the ovarian, uterine, and chorionic GnRH receptor, and with high affinity binding, affect changes in the ovarian and/or intrauterine environment that effect fertility, reproductive function, and the outcome of pregnancy. This finding is the basis of the invention disclosed herein. Thus, the present investigator has developed particular (non-mammalian) GnRH analogs that can be used for regulation of ovarian, tubal, and uterine function, induction of luteolysis and menstruation, and regulation of uterine PGE production. The ability of specific (non-mammalian) GnRH analogs to interact with the physiologic regulation of hCG, progesterone and prostaglandin during luteal phase of the cycle and early pregnancy, may be used to specifically interrupt luteal function and early pregnancy according to the invention as outlined here.

In additional embodiments, the specificity, activity and stability of these analogs was investigated at the ovary, the endometrium and the pituitary and their acute action was assessed on chorionic tissues. A direct action on ovarian and endometrial tissue was found. A potential direct contraceptive action of these analogs, as well as their placental hCG stimulation followed by inhibition and steroidogenic suppression activity is indicated. Such analogs could be used to regulate reproductive functions and disorders, used as menses regulators, contraceptives, or as abortifacients.

BRIEF DESCRIPTION OF DRAWINGS

FIG. 1. Placental Kds for Chicken II and Mammalian GnRH Analogs

◇ GnRH 0.0250 µM, ▽ GnRH 0.01250 µM, ○ GnRH 0.00625 µM, ● GnRH 0.00312 µM coincubated with varying concentrations of Chicken II GnRH (0.025 µM)

Figure 4A:
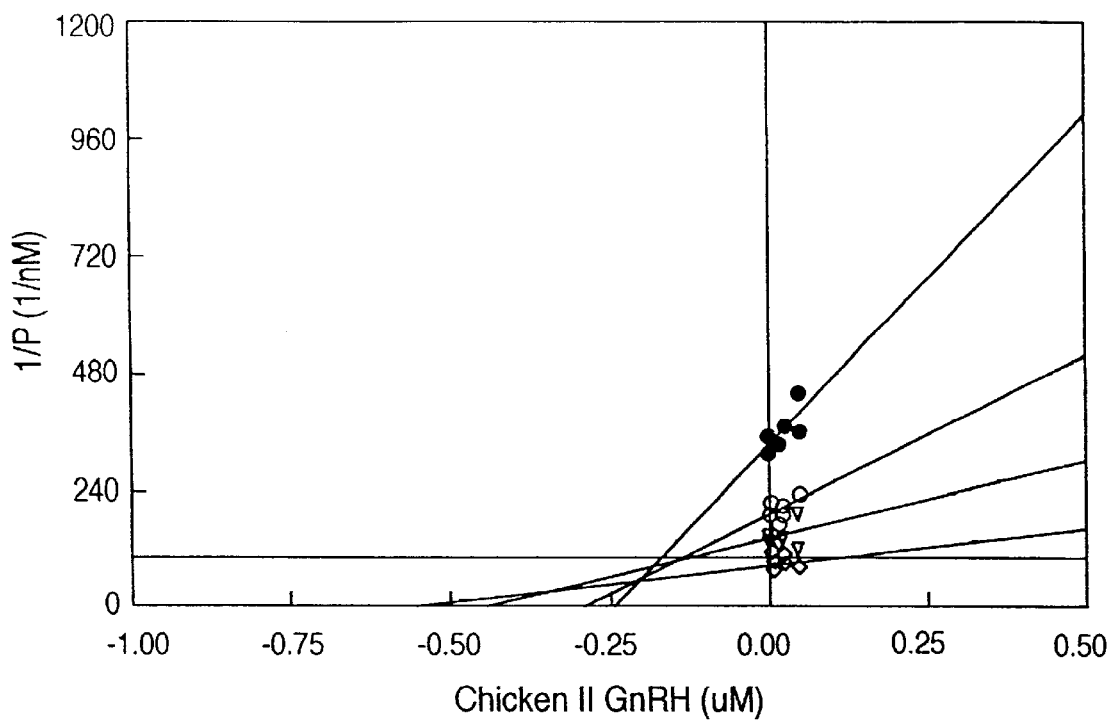
Figure 4B:
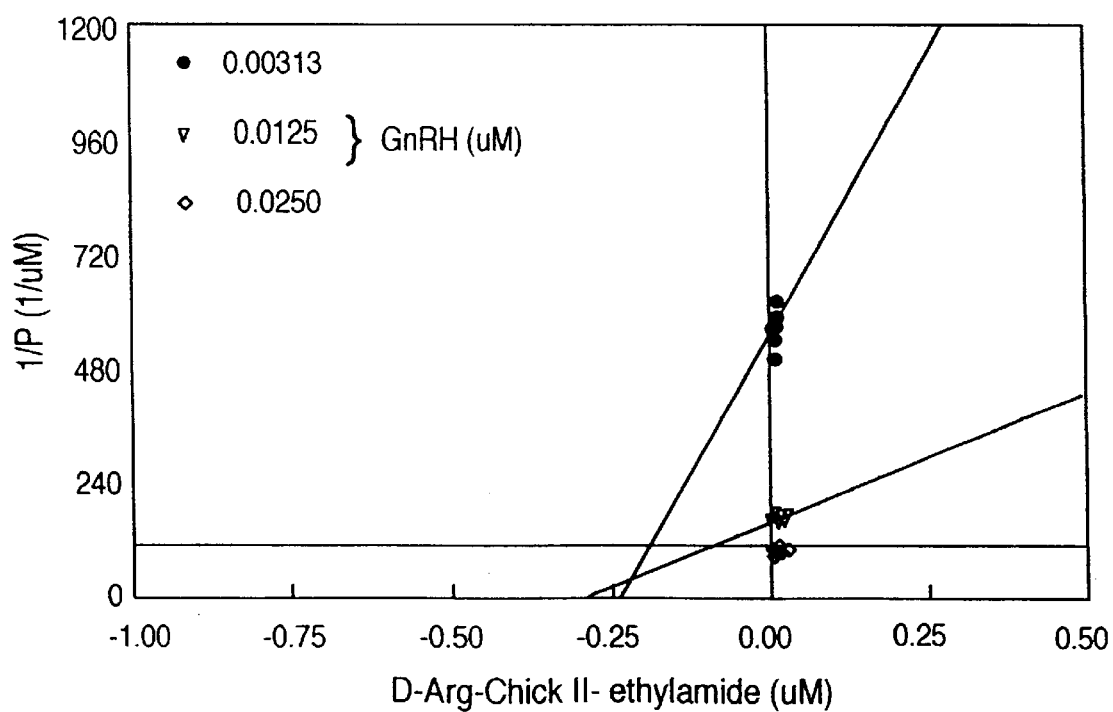

FIG. 4b. Inhibition of the Degradation of Mammalian GnRH by Placental Enzyme Chorionic Peptidase-1 by D-Arg-Chicken II-ethylamide.

◇ GnRH 0.0250 µM, ▽ GnRH 0.01250 µM, ○ GnRH 0.00625 µM, ● GnRH 0.00312 µM coincubated with varying concentrations of D-Arg(6)-Chicken II GnRH-aza-Gly(10)-amide (0.500 µM)

Figure 4C:
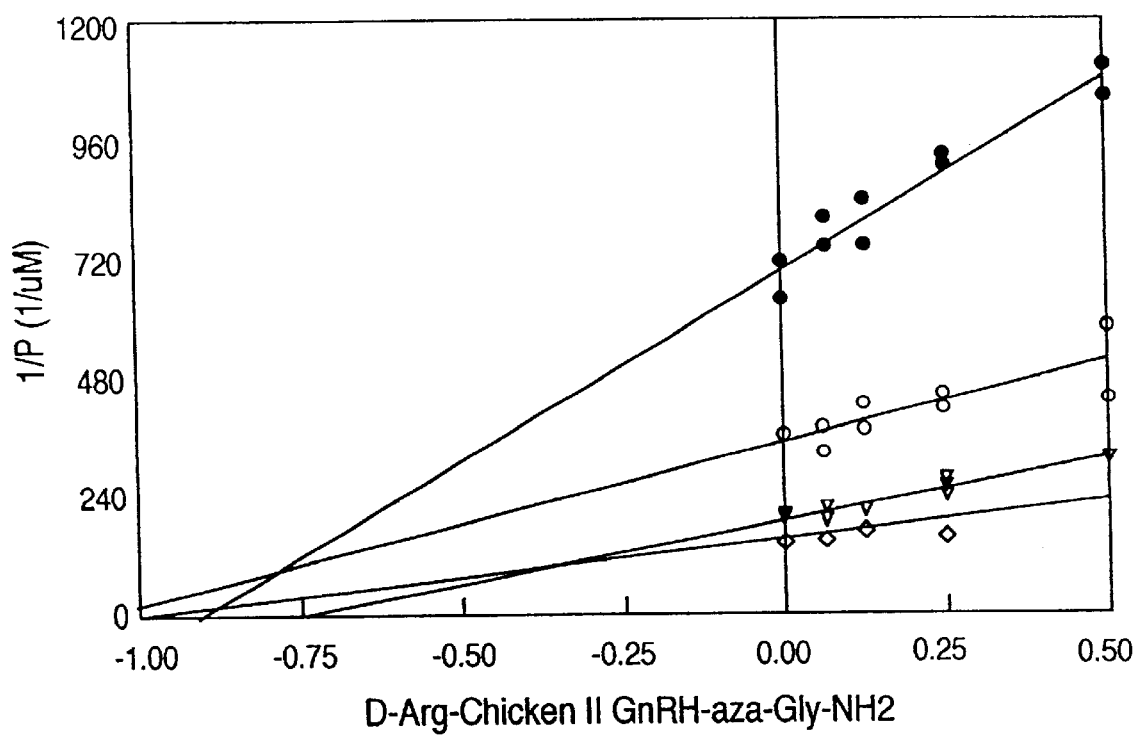

FIG. 4c. Inhibition of the Degradation of Mammalian GnRH by D-Arg-Chicken II RGnRH-aza-Gly-NH$_2$ ◇ GnRH 0.0250 µM, ▽ GnRH 0.01250 µM, ○ GnRH 0.00625 µM, ● GnRH 0.00312 µM coincubated with varying concentrations of D-Arg(6)-Chicken II GnRH-aza-Gly(10)-amide (0.500µM) with varying concentrations of D-Arg-Chicken II GnRH-aza-Gly-NH$_2$ FIGS. 5a and 5b. Release of hCG by Human Term Placental Explants Incubated with Varying Concentrations of D-Arg(6)-Chicken II GnRH-aza-Gly(10)-amide.

FIG. 6. Dose-Related Effect of D-Arg(6)-Chicken II GnRH-aza-Gly(10)-amide on hCG Release.

FIG. 7. Effect of Chicken II GnRH Analog on hCG Release.

FIG. 8. Effect of Chicken II GnRH Analog on Placental Progesterone Release.

FIG. 9a. Effect of Chicken II GnRH Analog on PGE2 Release Incubation 2 Hours.

FIG. 9b. Effect of Chicken II GnRH Analog on PGE2 Release Incubation 24 Hours.

Figure 10:
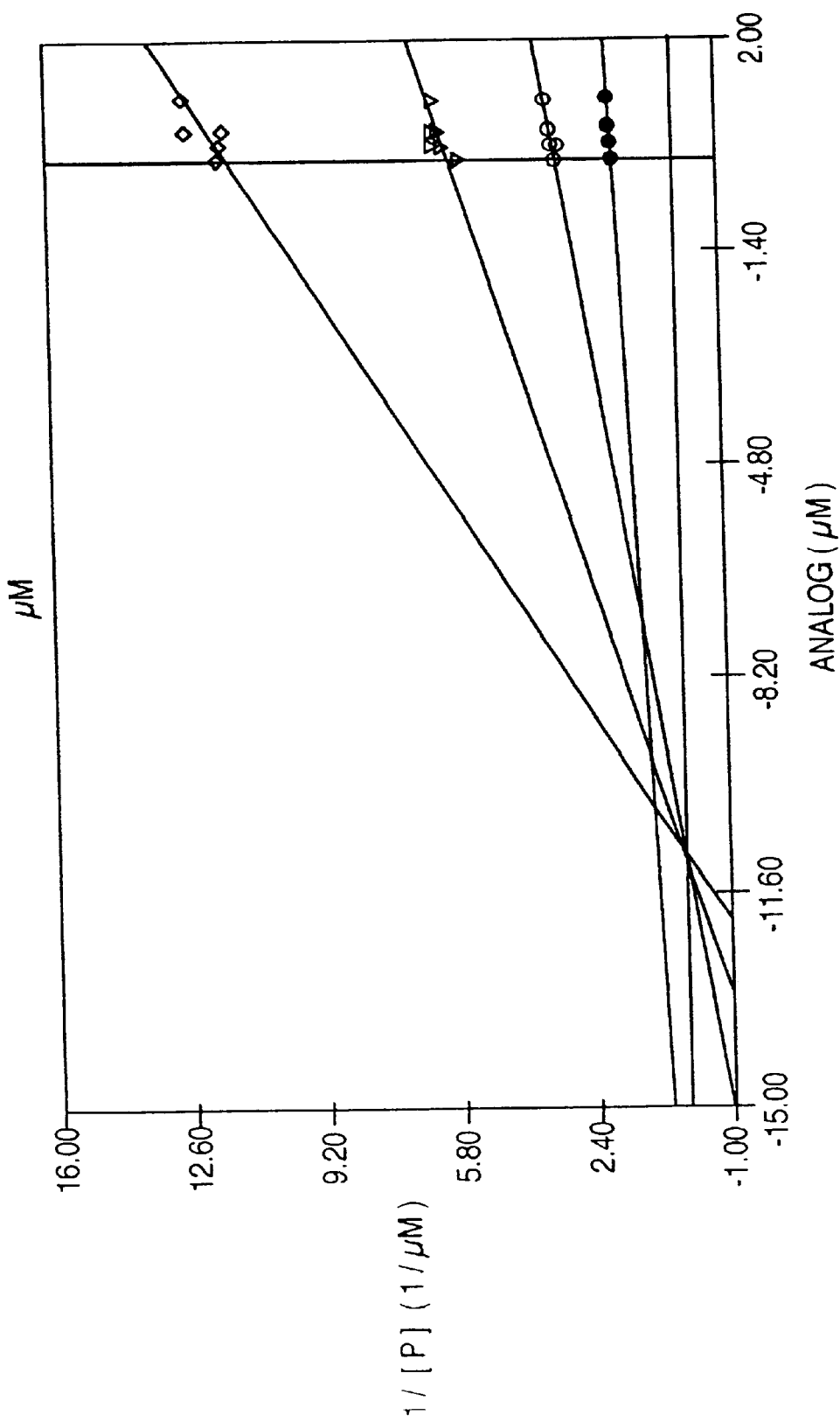

FIG. 10. Effect of TRH on the Degradation of GnRH by C-ase-1.

● GnRH 1.000 M, ○ GnRH 0.500 M, ▽ GnRH 0.250 M, ◇ GnRH 0.125 M

Figure 11:
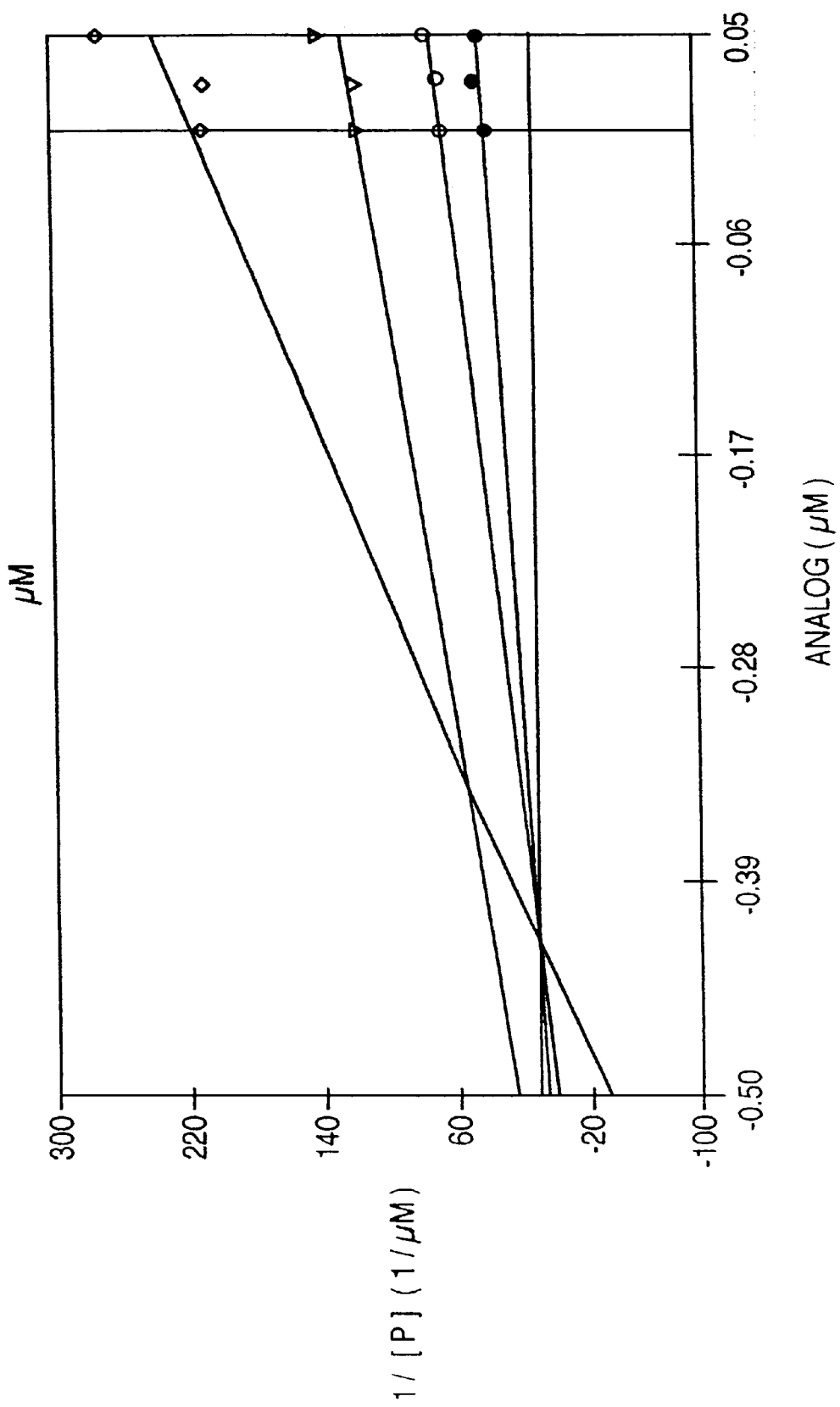

FIG. 11. Effect of Reduced Oxytocin on the Degradation of GnRH by C-ase-1.

● GnRH 0.050 M, ○ GnRH 0.0250 M, ▽ GnRH 0.012 M, ◇ GnRH 0.062 M

Figure 12A:
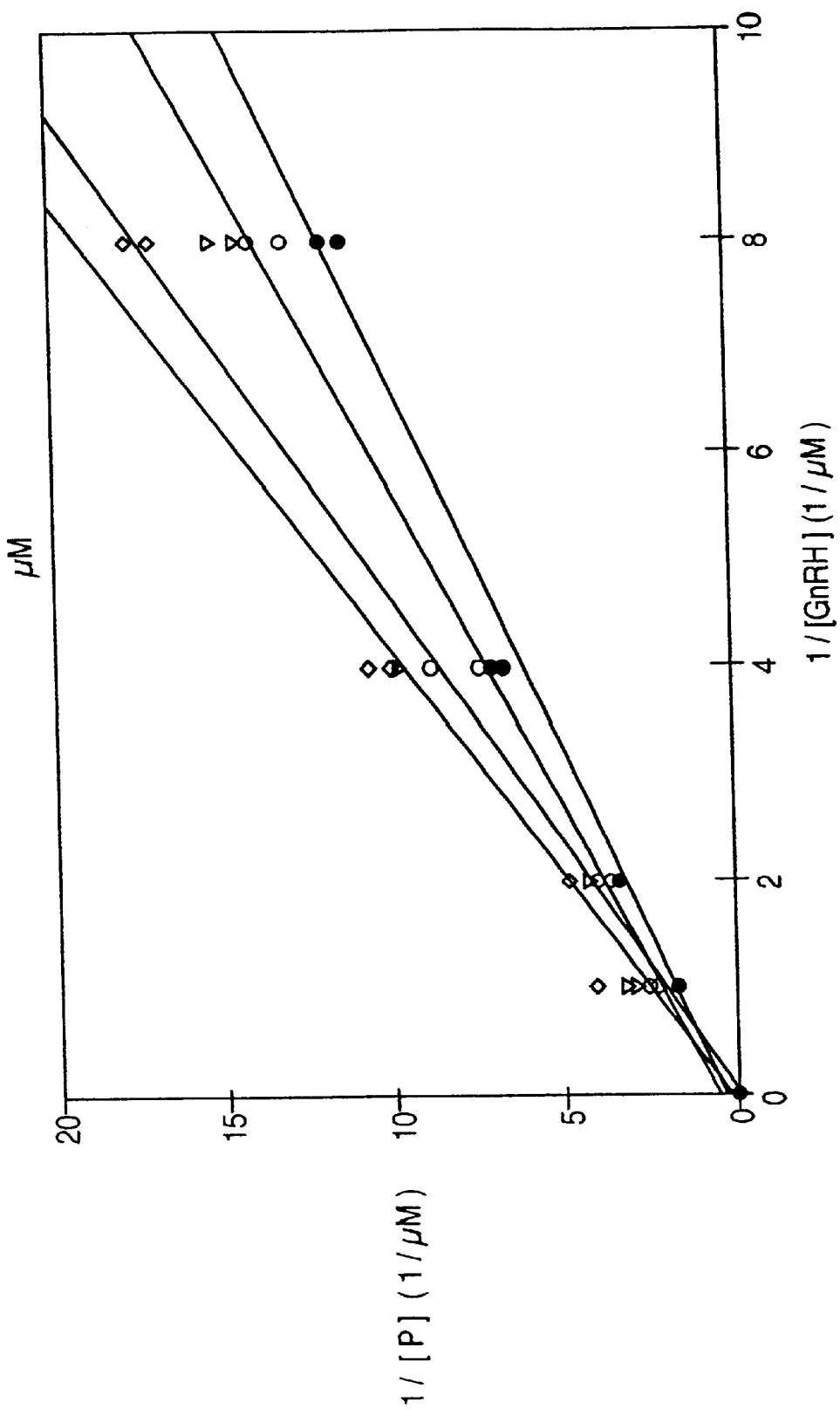
Figure 12B:
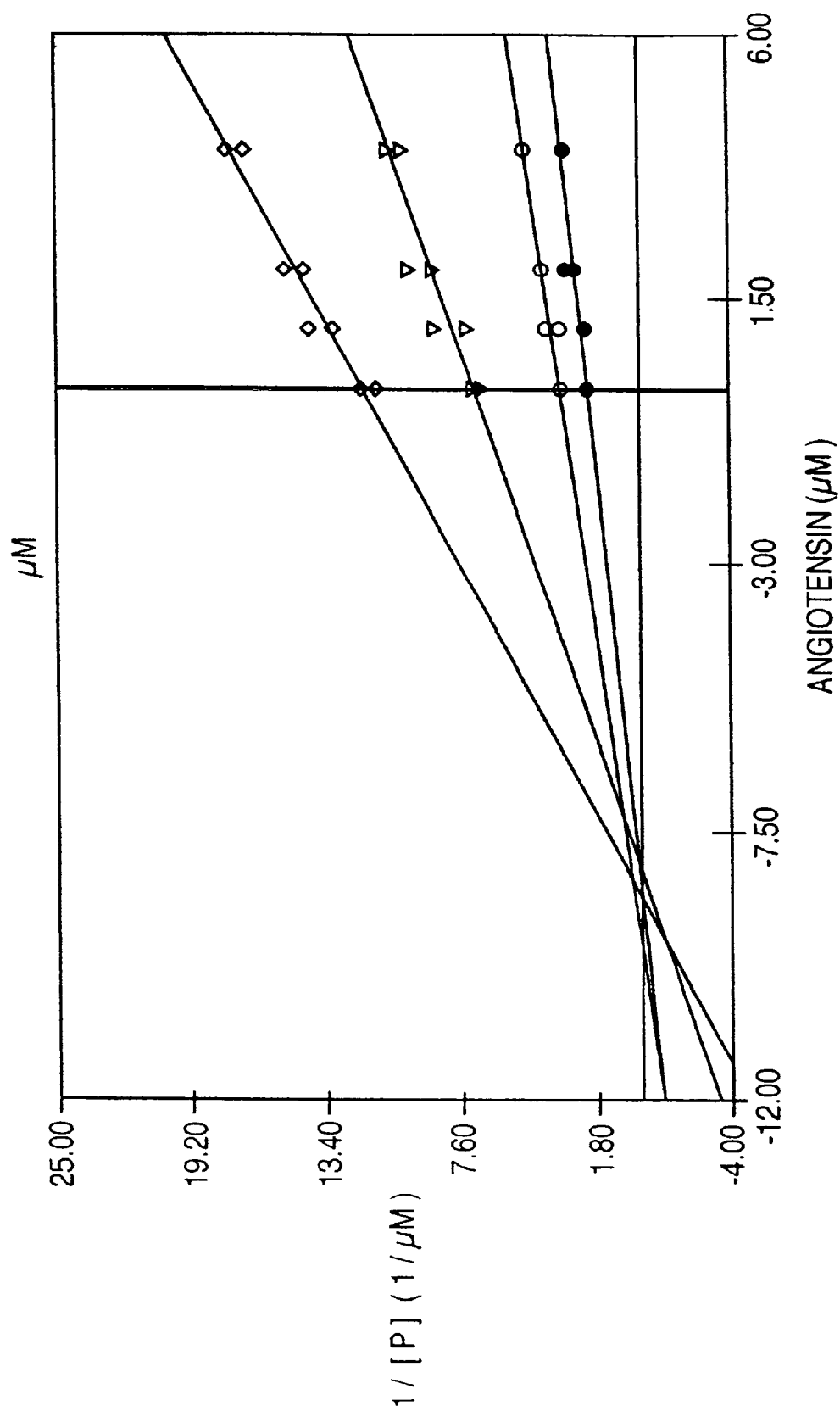

FIGS. 12A and 12B. Action of Angiotensin II on Degradation of GnRH.

12A ● Angio 0.12 M, ○ Angio 0.25 M, ▽ Angio 0.50 M, ◇ Angio 1.000 M

12B ● GnRH 1.00 M, ○ GnRH 0.50 M, ▽ GnRH 0.25 M, ◇ GnRH 0.12 M

Figure 13:
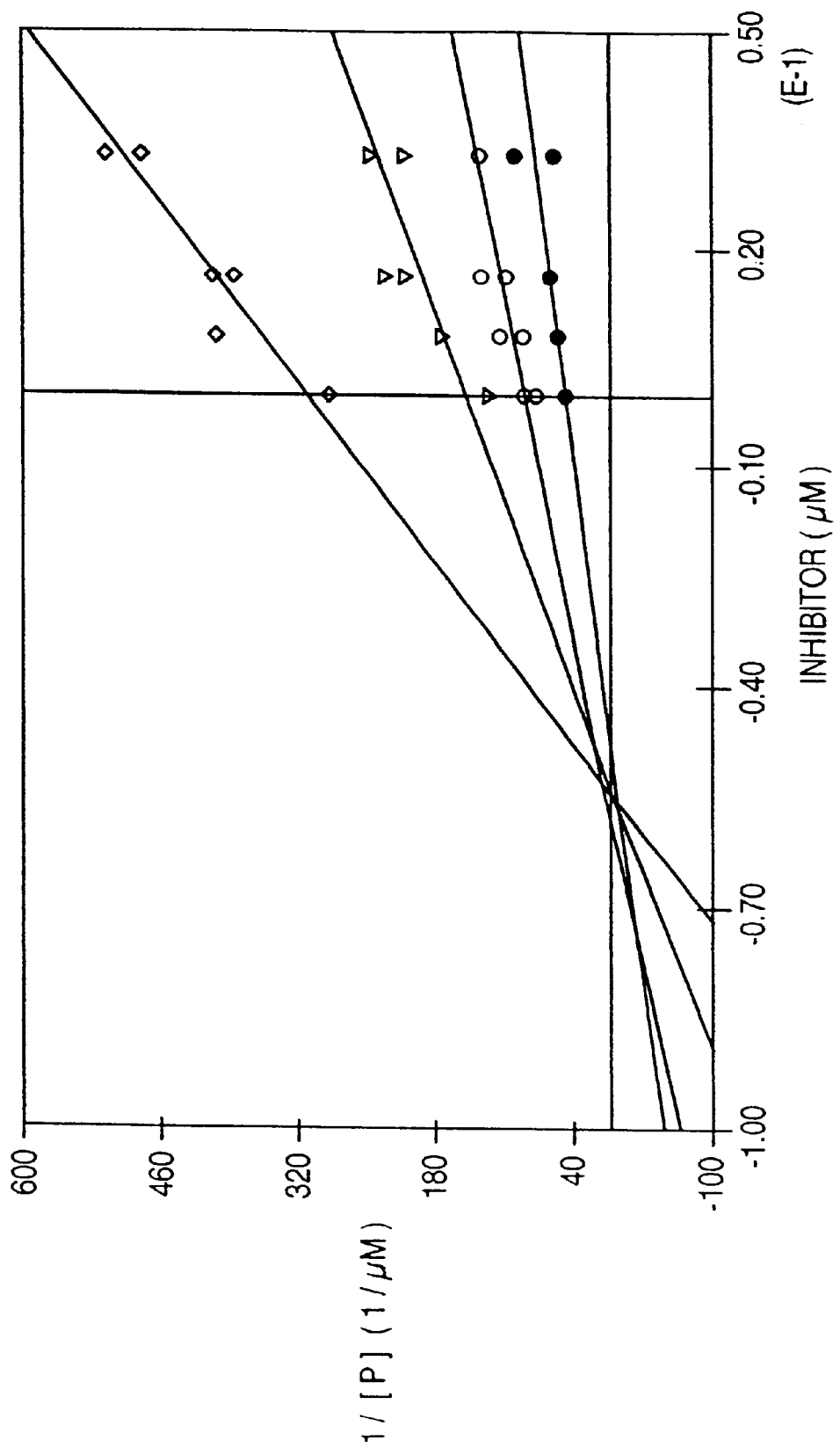

FIG. 13. Action of Chick II-ethylamide On Degradation of GnRH By C-ase-1.

● GnRH 0.00313 M, ▽ GnRH 0.0125 M, ◇ GnRH 0.0250 M

GnRH was actively degraded by C-ase-1. This activity of C-ase-1 was inhibited by, $^9$OH-Pro-GnRH, Lamprey, Chicken I-GnRH, Antide, Chicken II-GnRH and Salmon GnRH with a relative potency of 1.5, 1.5, 0.6, 0.6, and 0.2 and 0.2, respectively to that for GnRH. Both Chicken II GnRH-$^{10}$ ethylamide and $^6$Im-Btl-D-His-GnRH$^{10}$ ethylamide were essentially inactive, i.e., <0.001 inhibitory activity for GnRH.

Figure 14:
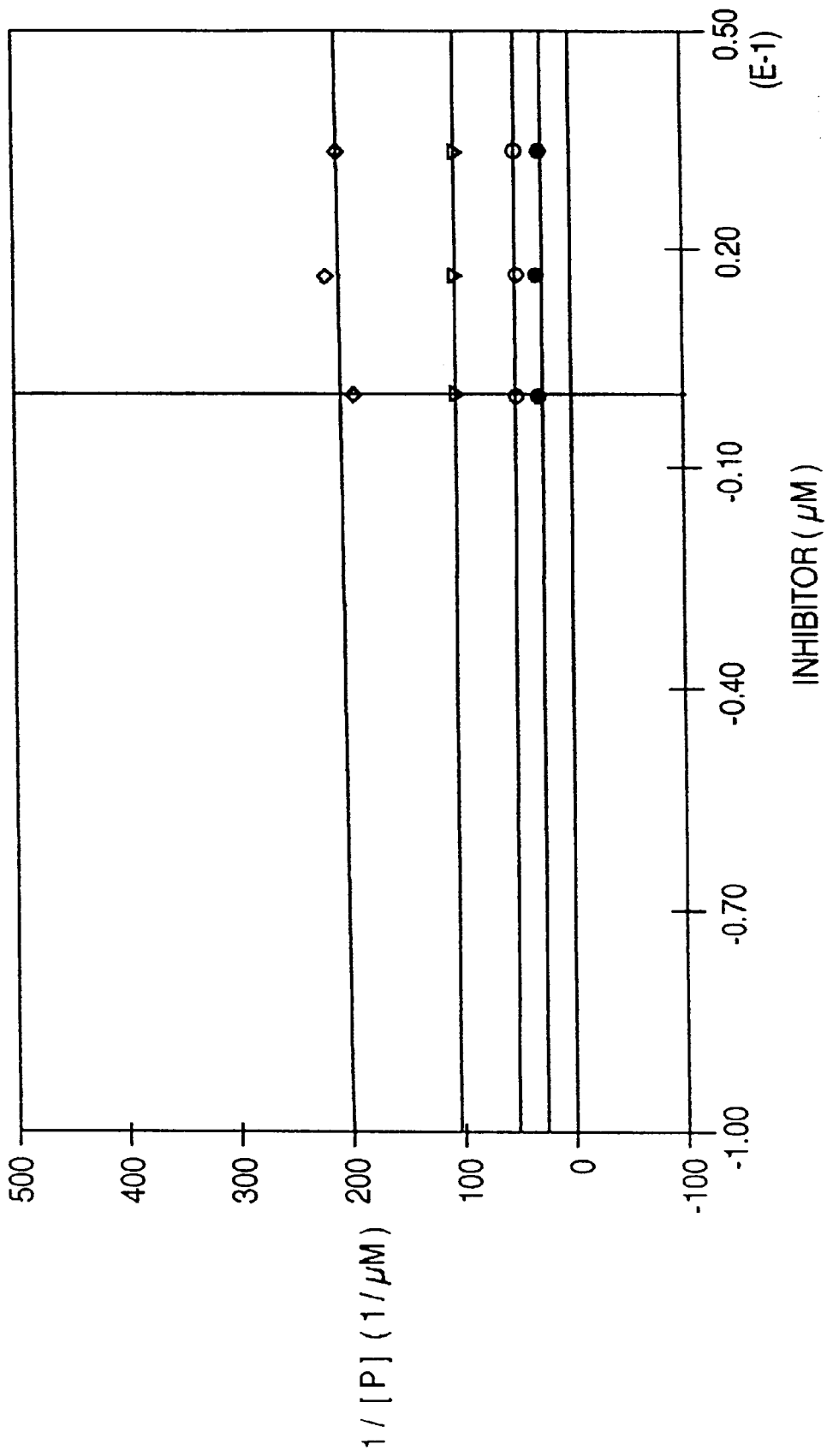

FIG. 14. Effect of des-Gly$^{10}$-Im-Btl-D-His$^6$-GnRH-ethylamide on Degradation of GnRH by C-ase-1.

● GnRH 0.0500 M, ○ GnRH 0.0250 M, ▽ GnRH 0.012 M, ◇ GnRH 0.062 M

Figure 15:
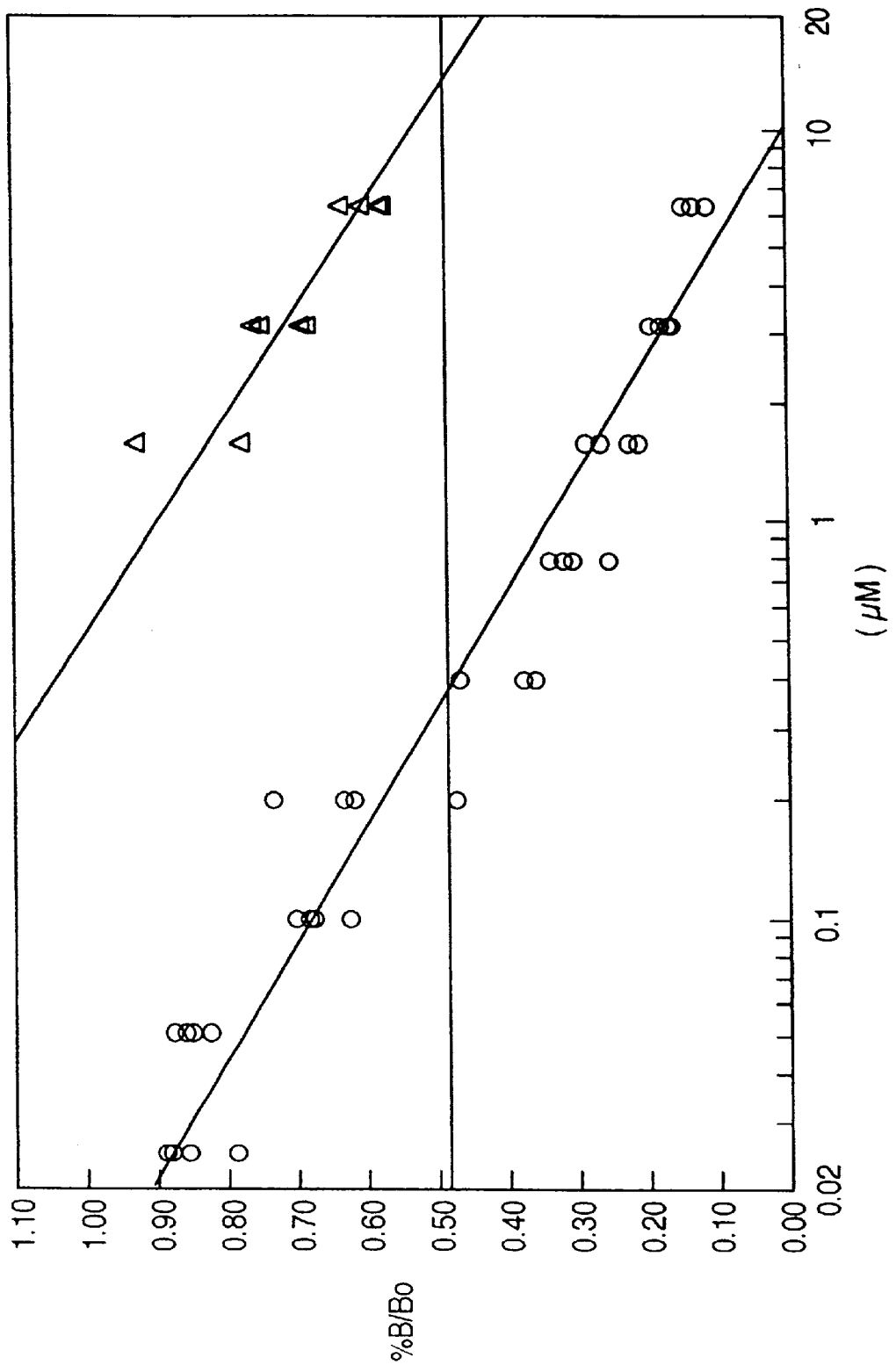

FIG. 15. Competitive Placental Receptor Binding For GnRH Analogs With Labeled Chicken II Analog.

Buserilin ▽ GnRH, ○ D-Arg-CII-EA

GnRH was bound by the placental GnRH receptor with a $K_d$ of $10^{-6}$ M. Chicken II GnRH was similar to GnRH. The $K_d$ for $^6$Im-btl-D-His-GnRH$^{-10}$ ethylamide was half the potency of GnRH, while Buserilin and $^6$D-Trp-GnRH$^{-10}$ ethylamide were twice as active as GnRH. The greatest potency, having a $K^d$ of 3 non-mammalian, i.e. 33-fold more activity than GnRH.

Figure 16:
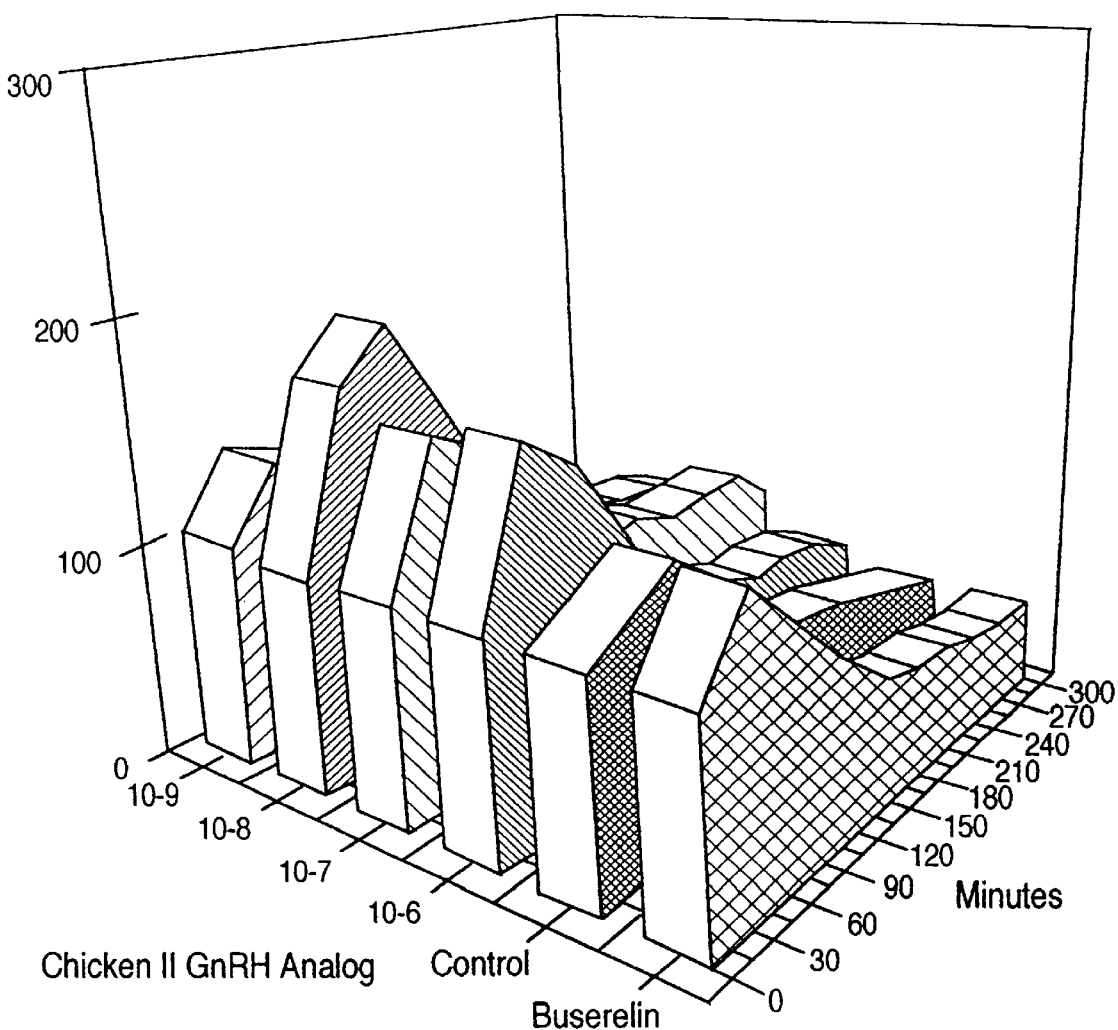

FIG. 16. Effect of Chicken II GnRH Analog on hCG in Early Human Placenta.

Figure 17:
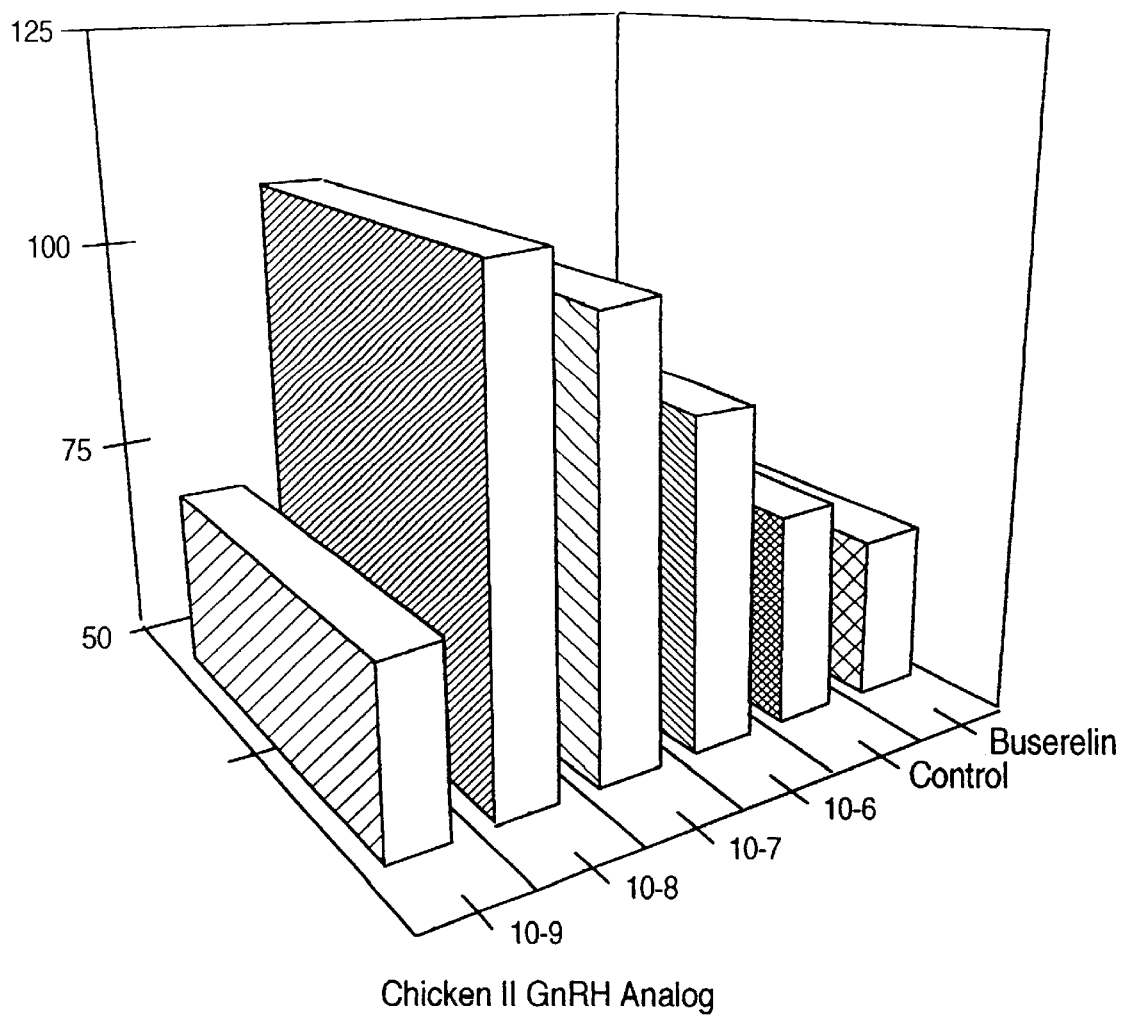

FIG. 17. Effect of Chicken II GnRH Analog on hCG in Early Human Placenta—Average Response Over 300 Minutes.

Figure 18:
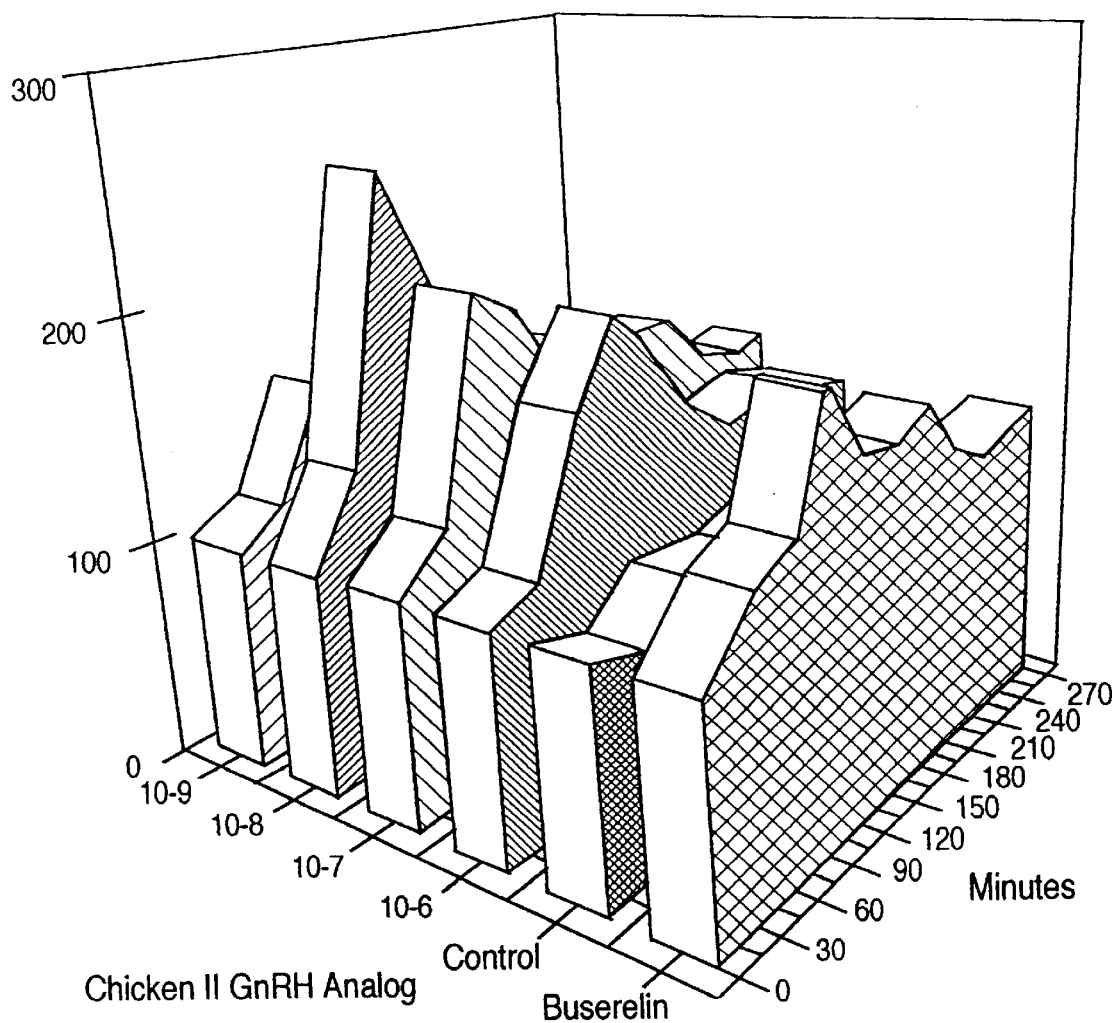

FIG. 18. Effect of Chicken II GnRH Analog on hCG on Early Human Placenta.

Figure 19:
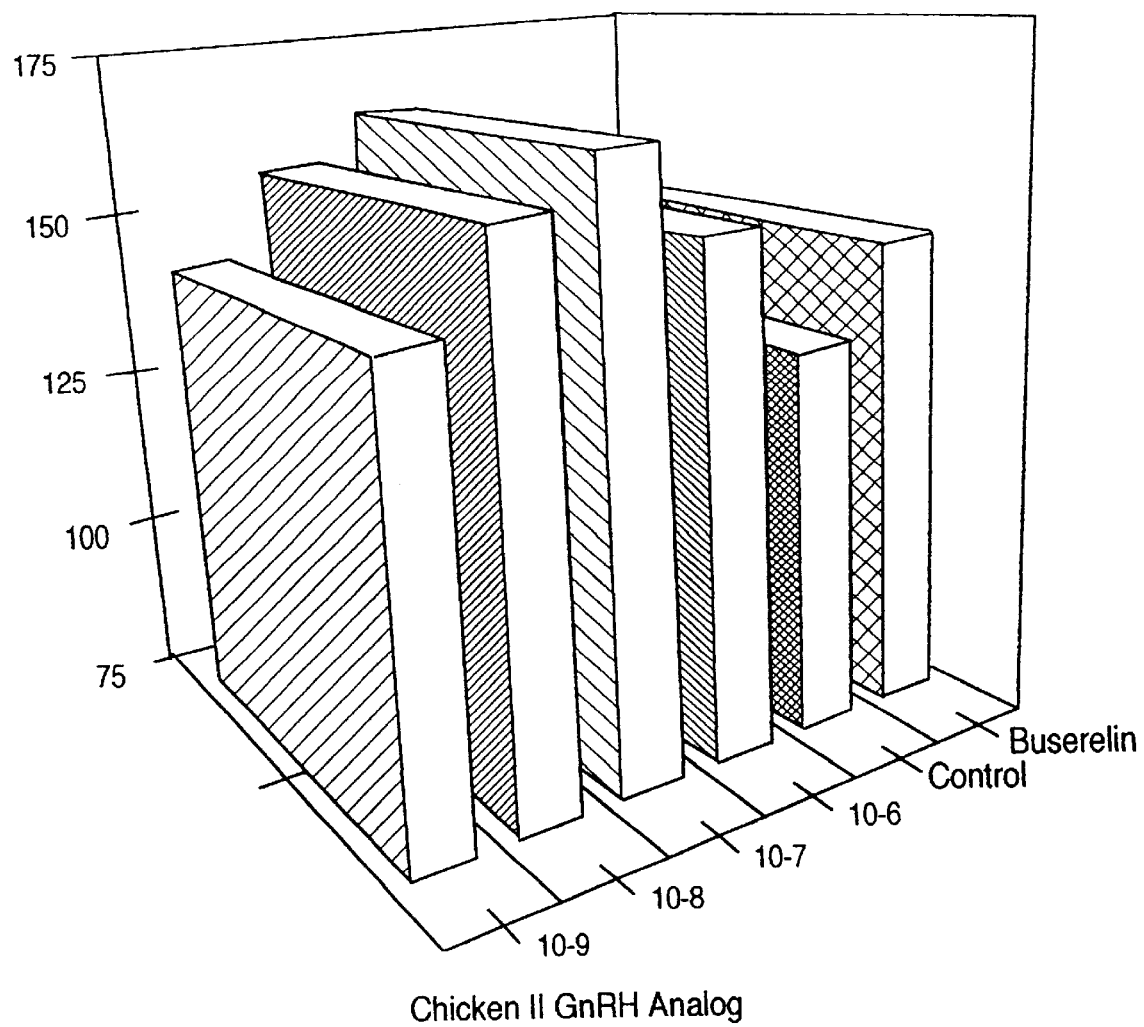

FIG. 19. Effect of Chicken II GnRH Analog on hCG on Early Human Placenta—Average Response over 270 Minutes.

Figure 20:
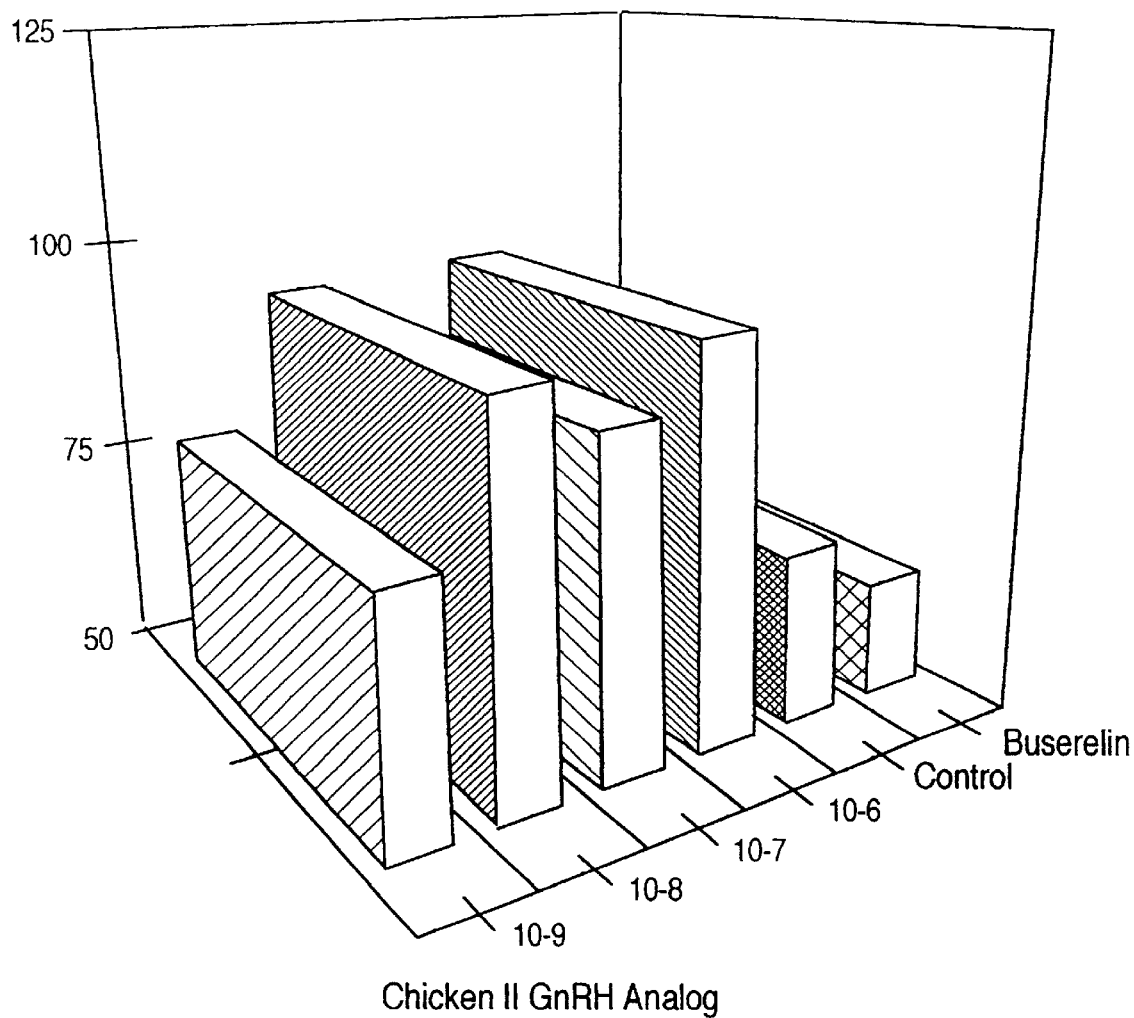

FIG. 20. Effect of Chicken II GnRH Analog on HCG in Early Human Placenta.

Figure 21:
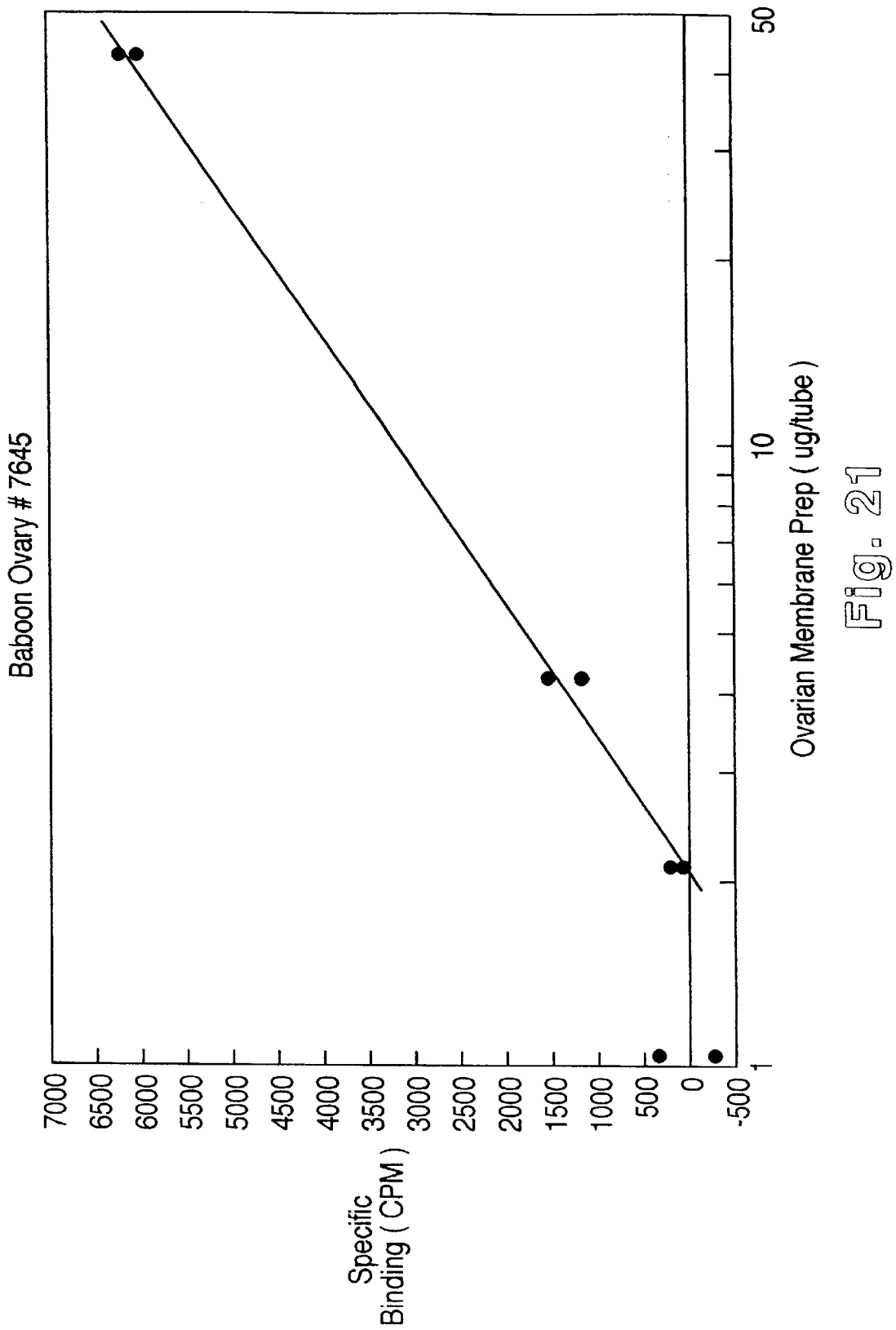

FIG. 21. Binding of D-Arg-Chicken II GnRH-aza-Gly-amide by Baboon Ovary.

Figure 22:
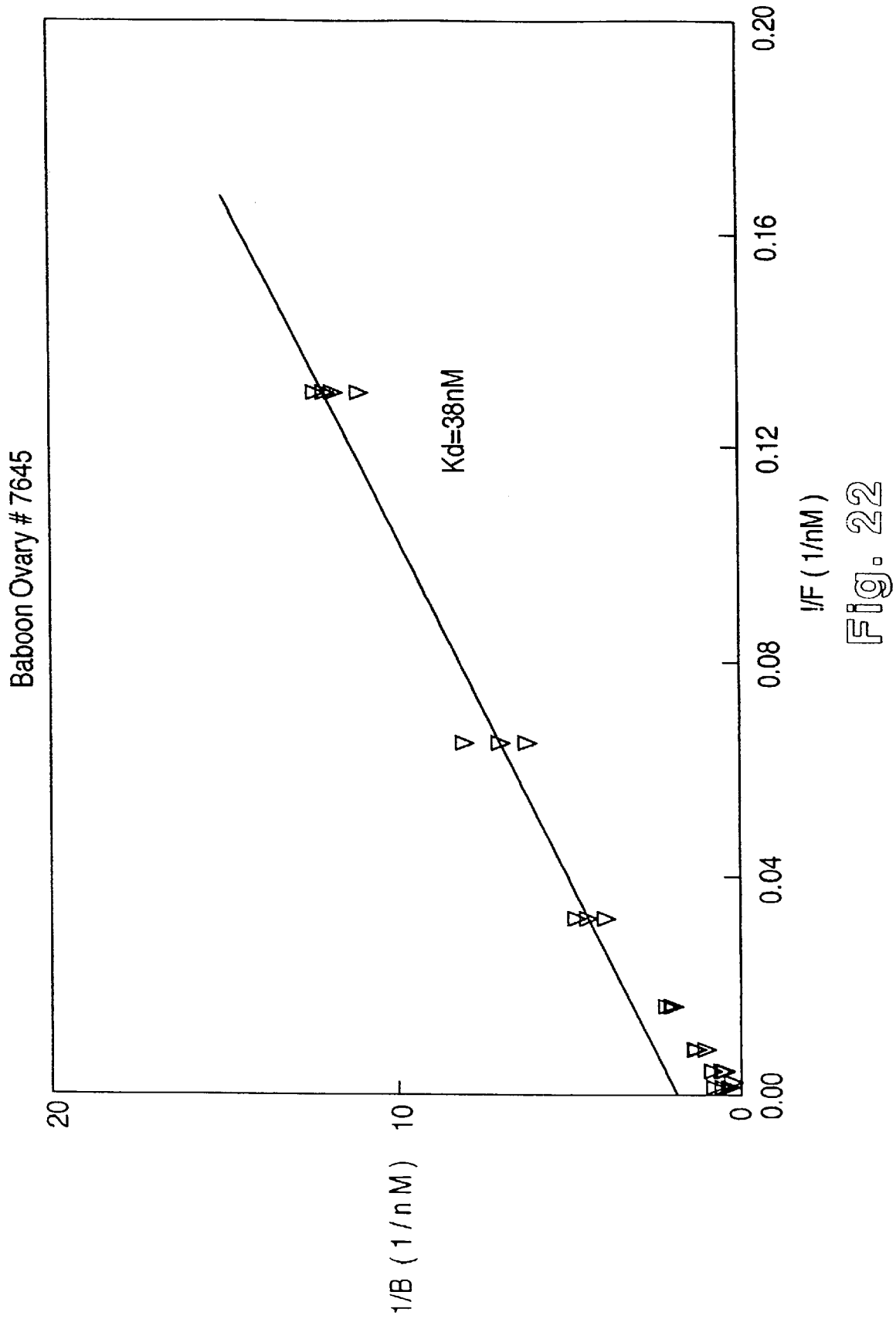

FIG. 22. Affinity of Chicken II Analog of Ovarian Receptor.

Figure 23:
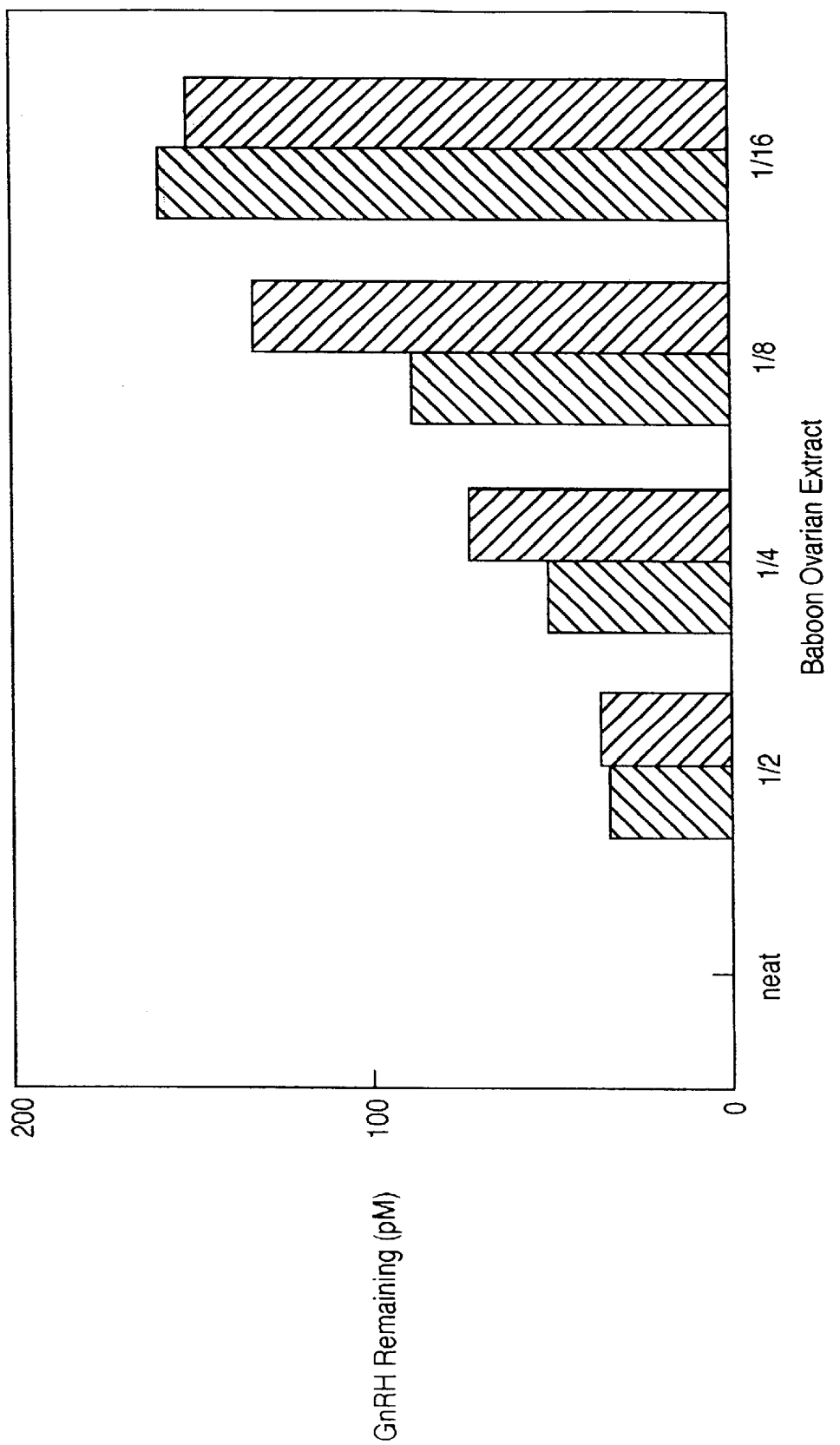

FIG. 23. Degradation of Mammalian GnRH in Baboon Ovary Extract.

Figure 24A:
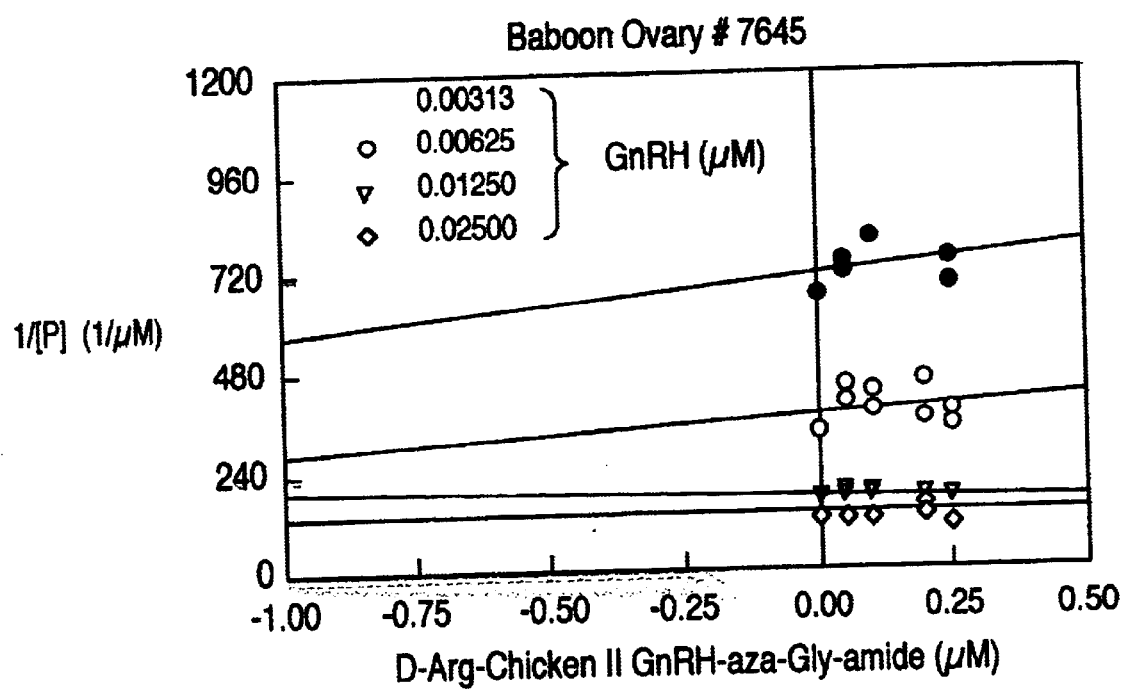
Figure 24B:
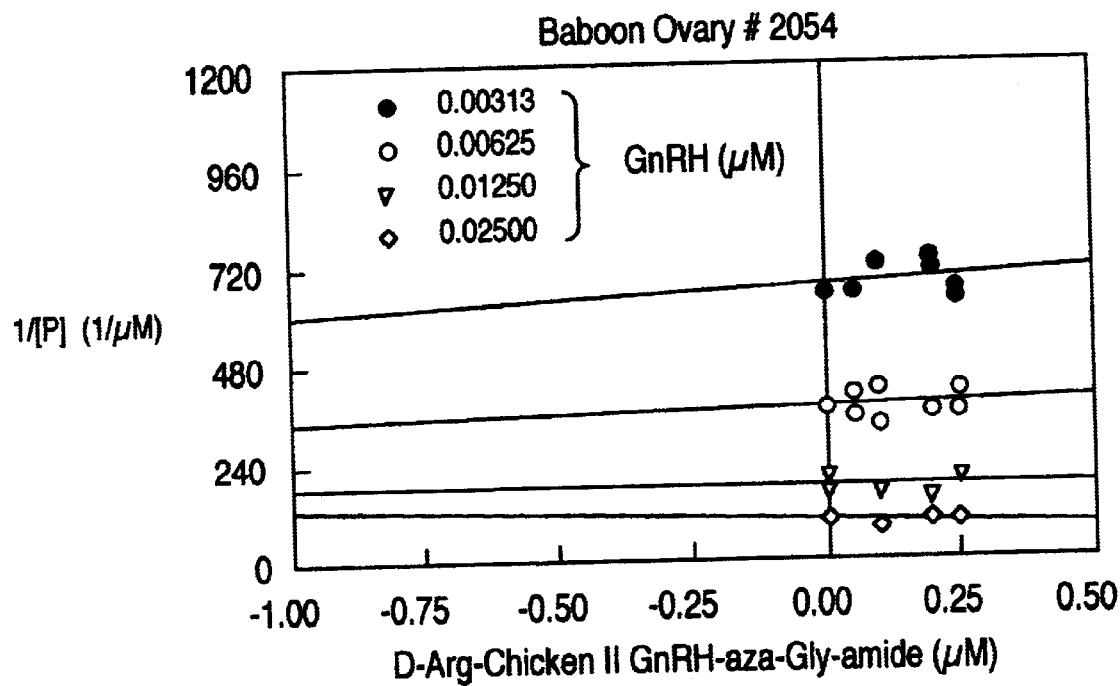
Figure 24C:
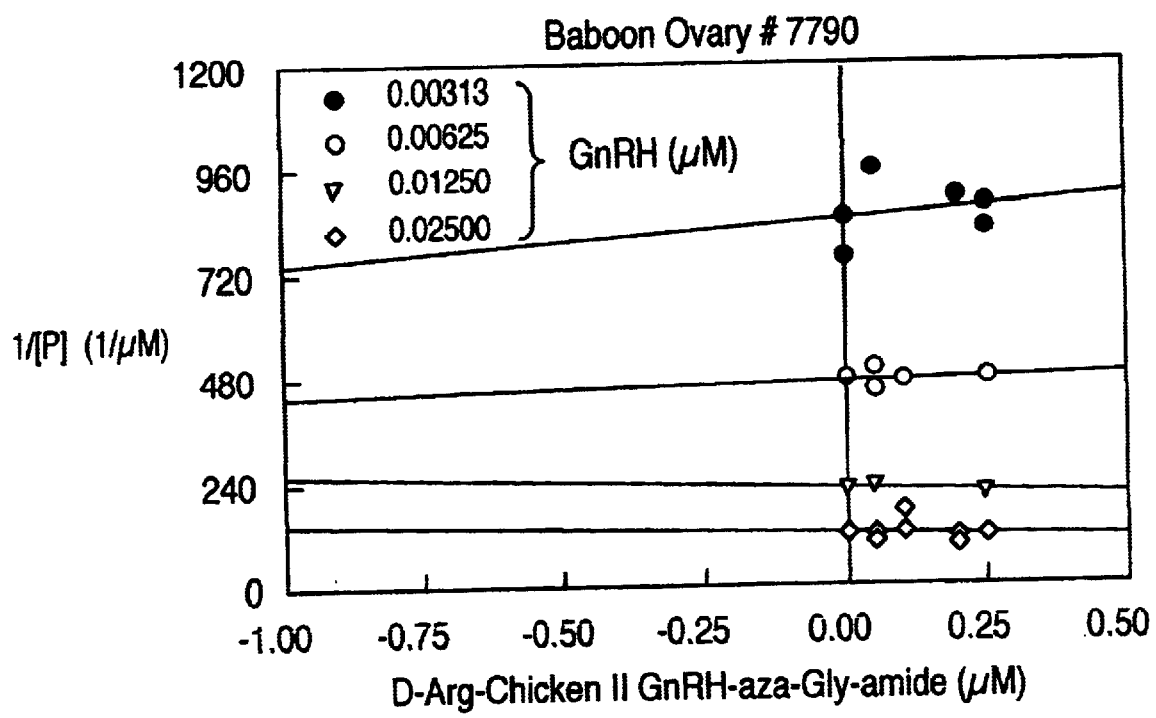

FIG. 24. Inhibition of Degradation of Mammalian GnRH Analog in the Baboon Ovary.

Figure 25:
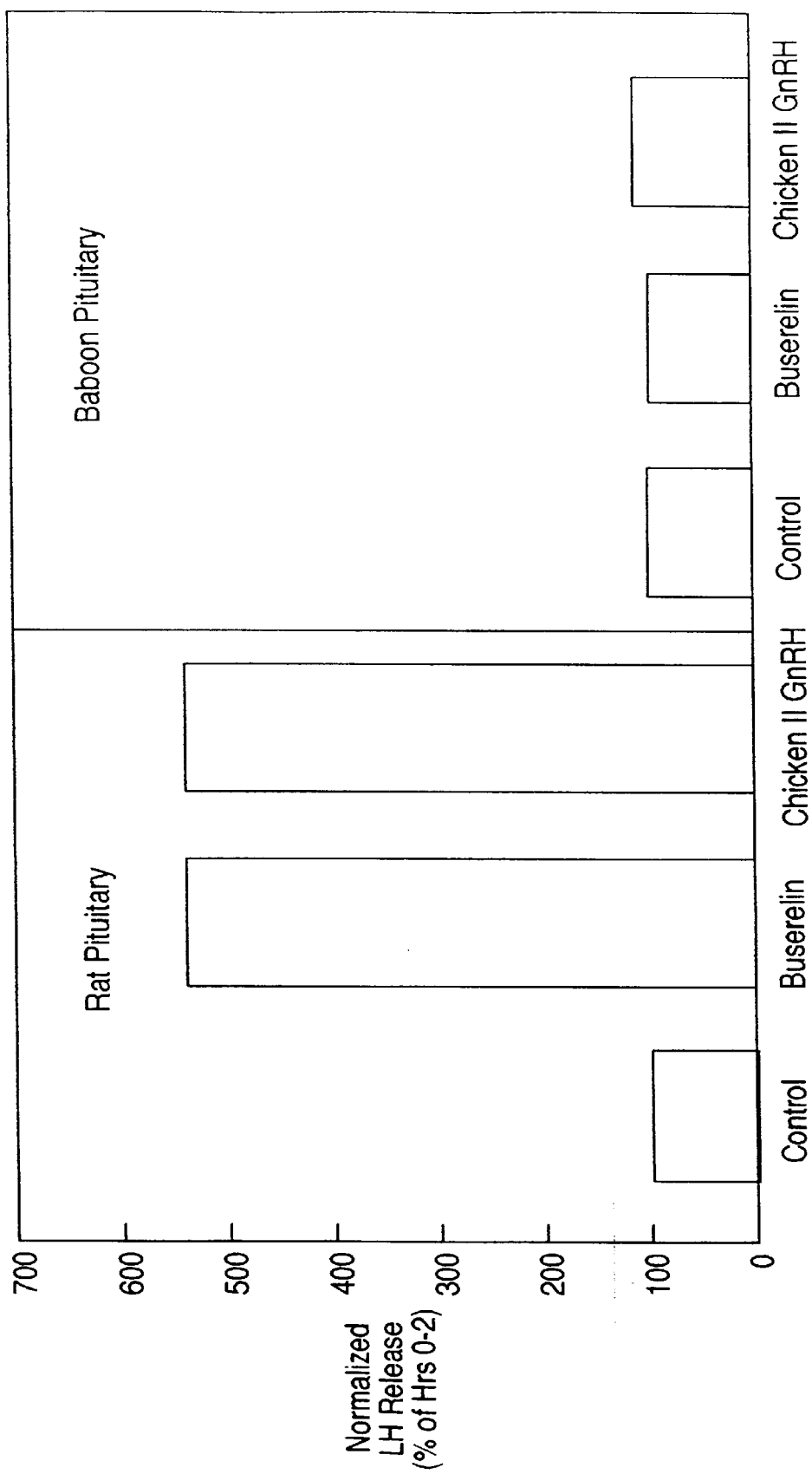

FIG. 25. Effect of Mammalian and Chicken GnRH Analogs on Pituitary LH Release.

Figure 26:
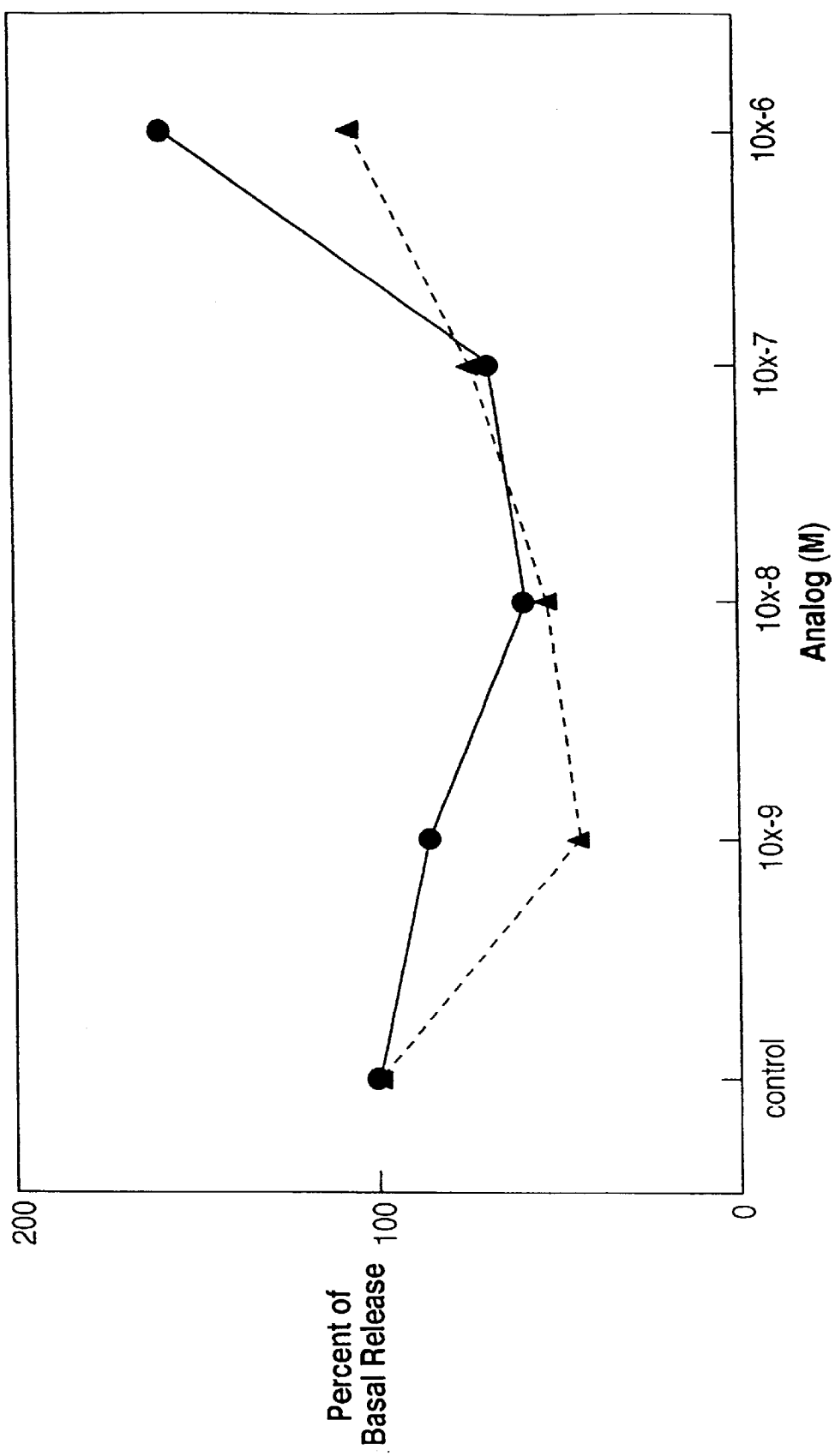

FIG. 26. Effect of Chicken II GnRH Analog on Two Different Baboon Pituitaries.

Figure 27:
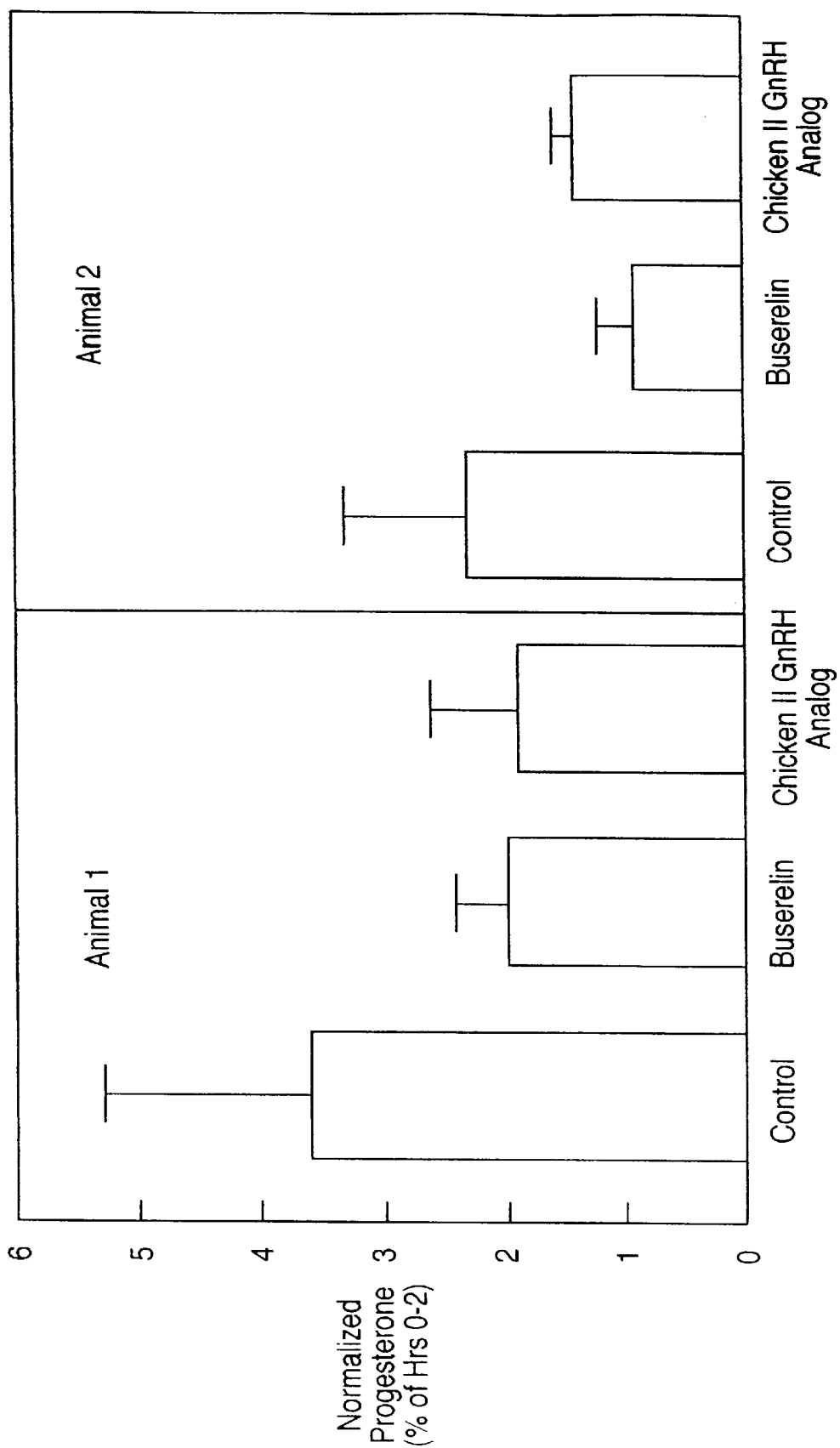

FIG. 27. Effect of Mammalian and Chicken GnRH Analogs on Pregnant Rat Ovaries.

Figure 28:
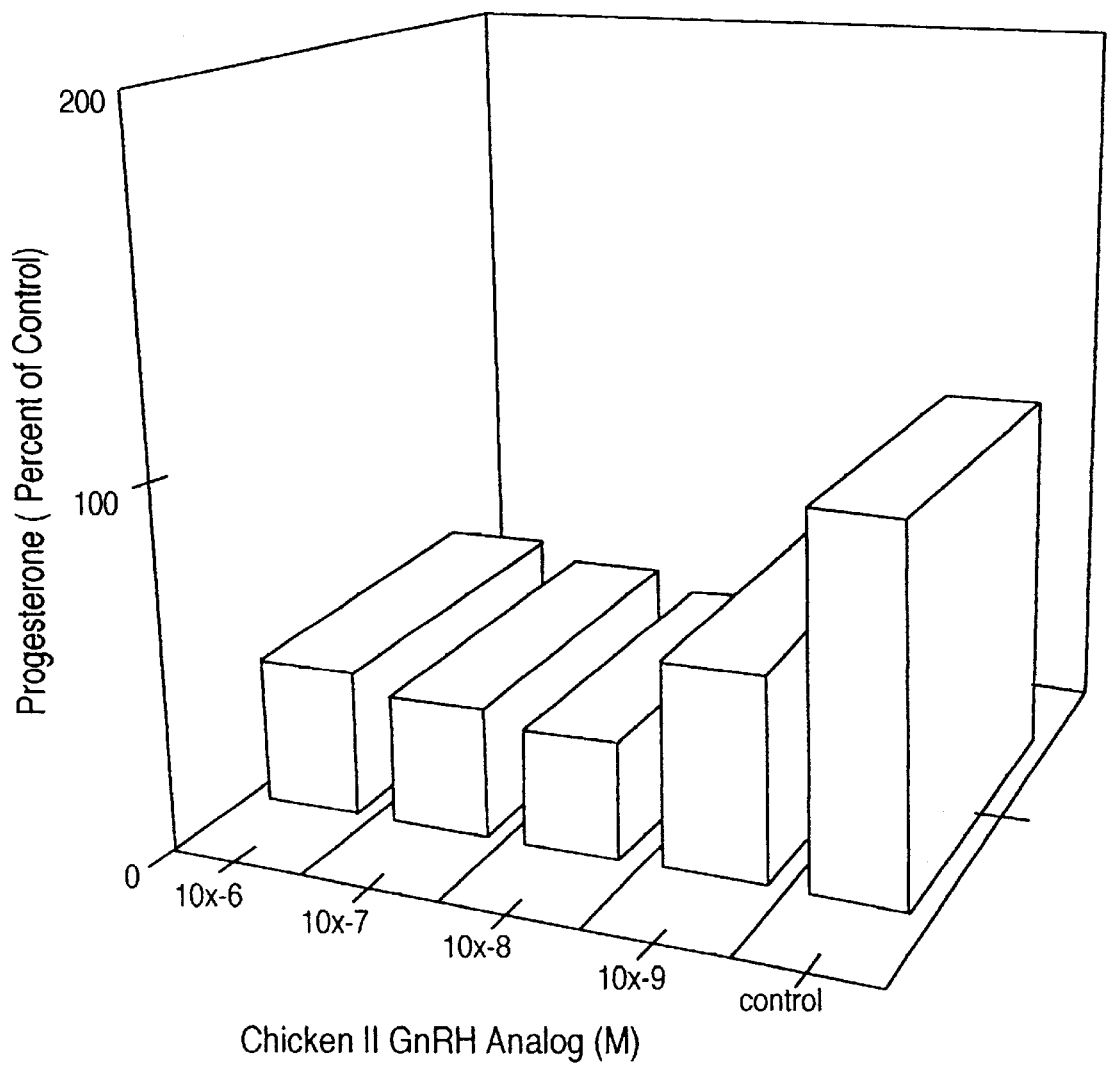

FIG. 28. Effect of Chicken II GnRH Analog on Baboon Granulosa Cells.

Figure 29:
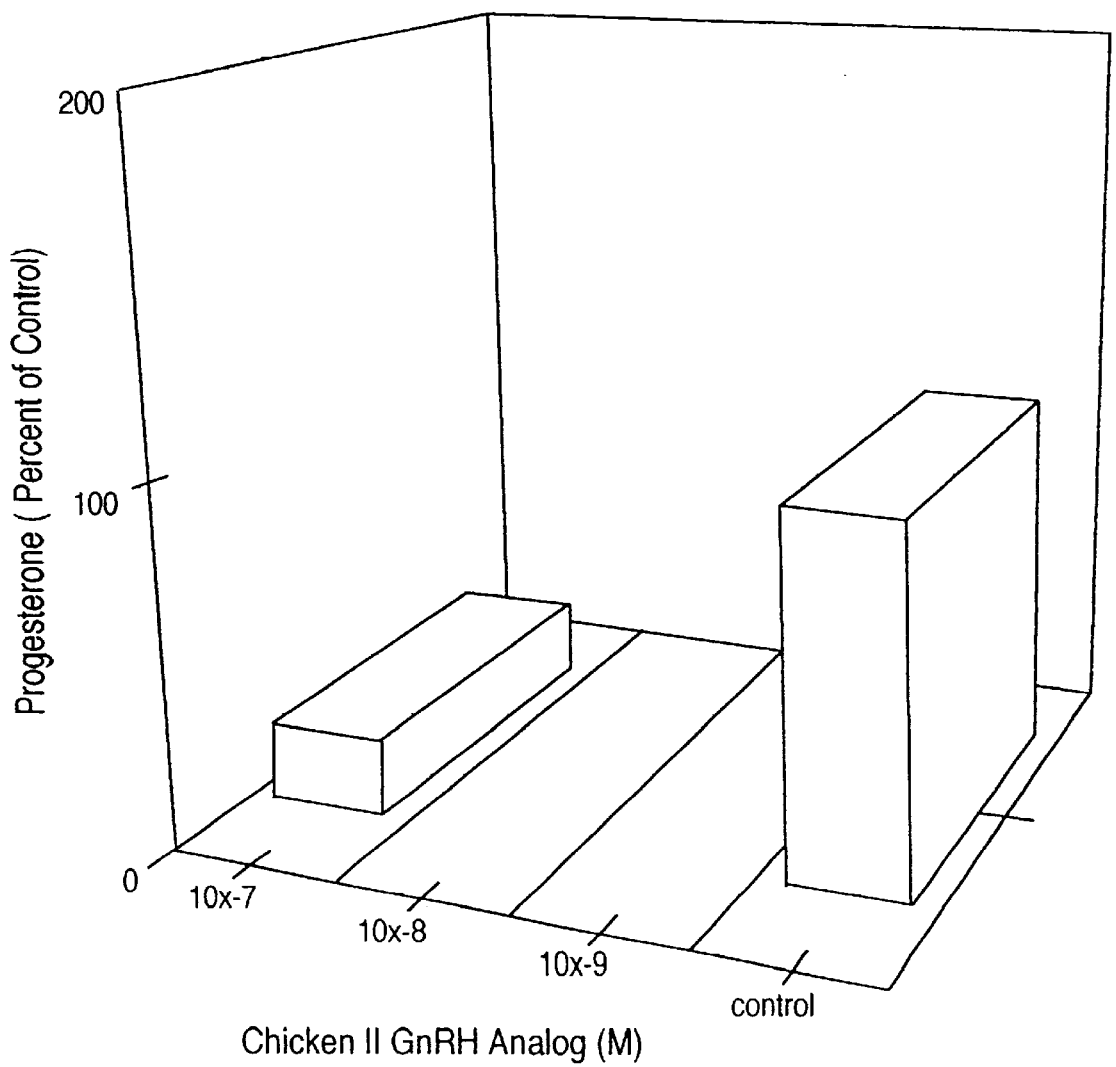

FIG. 29. Effect of Chicken II GnRH Analog on Baboon Granulosa Cells.

Figure 30:
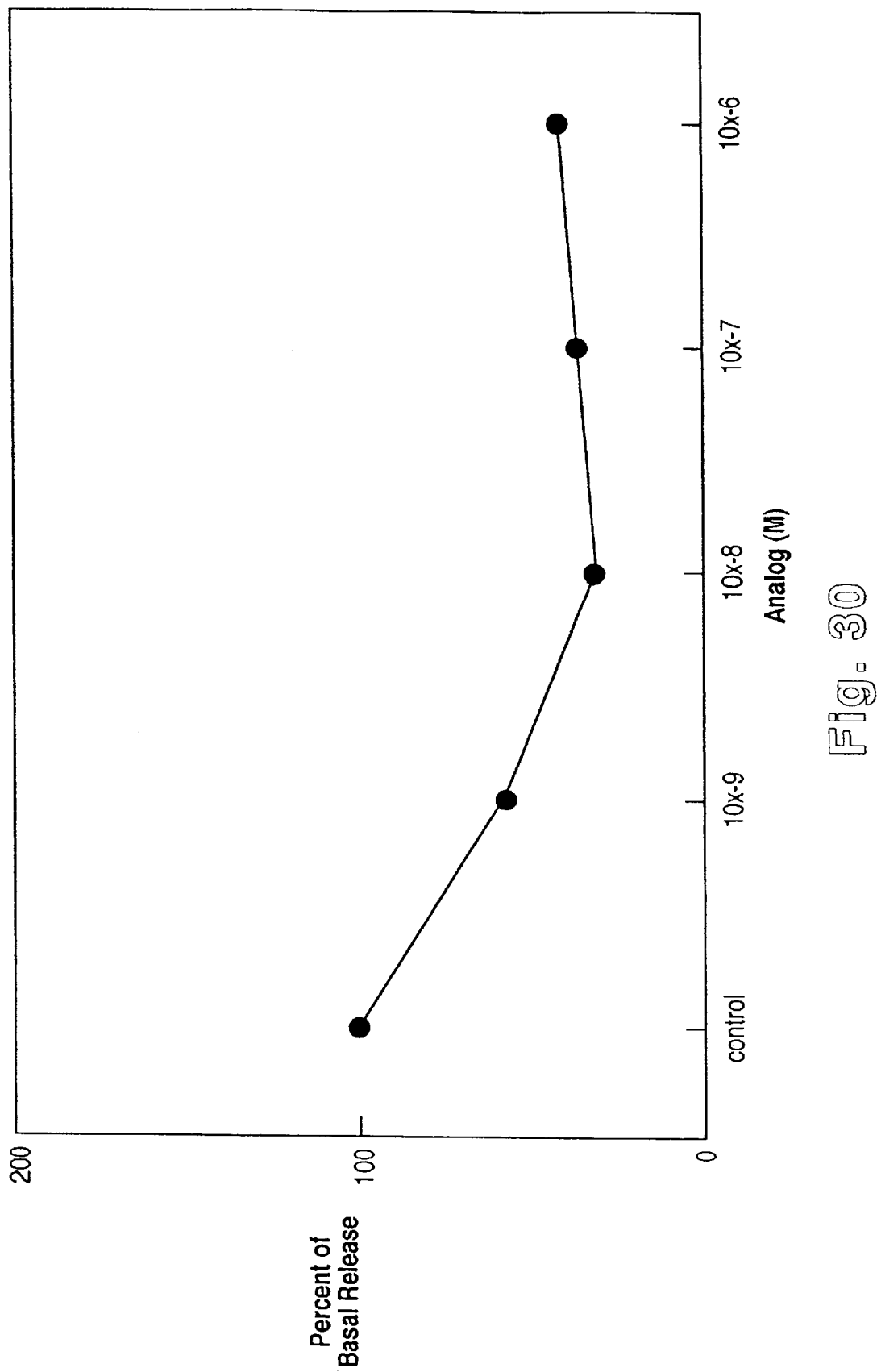

FIG. 30. Effect of Chicken II GnRH Analog on Baboon Granulosa Cells.

FIG. 31. Effect of Chicken II GnRH Analog on PGE$_2$ in Human Endometrial Cells.

DETAILED DESCRIPTION OF THE PREFERRED EMBODIMENTS

Following long-standing patent law convention, the terms "a" and "an" mean "one or more" when used in this application, including the claims.

For purposes of describing the present invention the chorion is described as the highly vascularized outer embryonic membrane that is associated with the allantois in the formation of the placenta.

An "isolated nucleic acid" is a nucleic acid the structure of which is not identical to that of any naturally occuring nucleic acid or to that of any fragment of a naturally occuring genomic nucleic acid spanning more than three separate genes. The term therefore covers, for example, (a) a DNA which has the sequence of part of a naturally occuring genomic DNA molecule, but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occuring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

Specifically, excluded from this definition are nucleic acids present in mixtures of (i) DNA molecules, (ii) transfected cells, and (iii) cell clones, e.g., as these occur in a DNA library such as a cDNA or genomic DNA library.

The term "antibody" includes whole antibodies and fragments thereof, single chain (recombinant) antibodies, "humanized" chimeric antibodies, and immunologically active fragments of antibodies (eg. Fab fragments).

The phrase "SEQ ID NO: X" includes SEQ ID NO: 2 with at least one conservative amino acid substitution.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Design of Non-Mammalian GnRH Analogs

The present example outlines how analogs of non-mammalian GnRH with increased activity in chorionic, ovarian, tubal and uterine tissues are designed.

Existing mammalian GnRH analogs are designed for activity at the pituitary GnRH receptor and with extended stability in the circulation of non-pregnant individuals. Yet, the existing data indicate that the ovarian, uterine, and chorionic tissues have a high affinity GnRH receptor which differs from that in the pituitary. In addition, the degradation of GnRH is different in the ovary, uterus, and placenta during pregnancy. Therefore, prior known pituitary mammalian GnRH analogs have not been designed for use at extra-pituitary sites or during pregnancy, and potent non-mammalian GnRH analogs have not been designed for use at extra-pituitary sites or during pregnancy. The present invention provides potent non-mammalian GnRH analogs.

Method and Analysis: Non-mammalian analogs of GnRH were synthesized by order. They were specifically designed to prevent degradation of the analog in extra-pituitary tissues, in the maternal circulation as well as within the intrauterine tissues. This allows for the maintenance of sufficient concentrations of analog to remain active when administered via the individual and to reach the extra-pituitary and intrauterine tissues of pregnancy. Due to the particular specificity of the ovarian, tubal, uterine, and placental receptor and specific peptidase in maternal blood and ovarian, tubal, uterine, and placental tissue, the particular analogs of the invention were designed. Analogs of the salmon (SEQ ID NO: 4) and chicken II GnRH (SEQ ID NO: 2) sequences, that both show greater affinity for the ovarian, tubal, uterine, and placental receptor than for the pituitary receptor, were modified to the tenth amino acid to ethylamide or aza-Gly$^{10}$-NH$_2$ analog to make them resistant to degradation in the circulation and by post-proline peptidases (GnRH analogs 1 and 2). The chicken II GnRH sequence (SEQ ID NO: 2) and the salmon GnRH sequence (SEQ ID NO: 4) were also modified at the 6 position using D-Arg, making them resistant to degradation by the endopeptidase in blood, and were modified at the 10 position making them stable in maternal blood and the ovarian, tubal, uterine, and chorionic tissues (GnRH analogs 2 and 4). These analogs are expected to have increased binding to the ovarian, tubal, uterine, and placental receptor and increased metabolic stability.

EXAMPLE II

Placental Receptor Binding Activity Placental Receptor Studies

The placental receptor binding activity of the different non-mammalian GnRH analogs of the present invention were compared. There is a human placental GnRH receptor which is distinct from that at the pituitary. Prior mammalian GnRH analogs have been designed to increase activity at the pituitary GnRH receptor and stability in the circulation of non-pregnant individuals. These analogs do not demonstrate potent binding activity at the placental receptor as they do at the pituitary receptor. The non-mammalian GnRH analogs have been designed to interact with preference at the placental receptor and not the pituitary receptor. They have also been designed to limit degradation by the ovarian, tubal uterine, and chorionic enzymes, present in maternal circulation as well as the ovary, fallopian tube, uterus, and placenta. Placental binding activity of the newly synthesized non-mammalian GnRH analogs have been compared to that for existing pituitary-active analogs of mammalian GnRH.

Method and Analysis: The newly synthesized non-mammalian GnRH analogs and other commercially available analogs were used in placental receptors binding and enzyme stability study described here. On the basis of these studies, the most receptor potent and most enzyme-stable analogs were chosen for further biopotency studies. GnRH receptors were purified from the membrane fractions from placentas. The purification procedure for the placental GnRH receptor was performed using a modification of the method described by Bramley et al., which reference is specifically incorporated herein by reference for the purpose. Bramley T A, McPhie C A, Menzies G S 1994 Human placental gonadotropin-releasing hormone (GnRH) binding sites: 111. Changes in GnRH binding levels with stage of gestation. Placenta 15:733–745. Addition of enzyme inhibitors for the endogenous C-ase-1 were used as well as agents for receptor stabilization. Initially, receptor-binding assays using $^{125}$I-Buserelin as label were performed. The competitive binding of each of the analogs was studied over a dose range of $10^{-11}$ to $10^{-6}$ M. Incubation was at room temperature and receptor bound label was precipitated with polyethylene glycol. Specific and non-specific binding was determined. The data was subjected to Scatchard analysis. The non-mammalian analogs' ability to bind to the placental GnRH receptor was compared to that for synthetic mammalian GnRH, Buserelin and other mammalian analogs and the newly synthesized non-mammalian GnRH analogs. The more potent analogs were then studied in homologous receptor assays using newly synthesized non-mammalian GnRH analog as the radioiodinated label. This way, the receptor affinity for that analog could be precisely determined. Receptors from three different term placentas were used to study each of these analogs. The most potent analogs were used for the C-ase-1 stability studies. These data enabled the inventor to predict the most potent non-mammalian GnRH analog structure for the placental GnRH receptor, and assisted in the design of even more potent analogs for the chorionic GnRH receptor.

In these and additional studies, placental GnRH receptors were purified from human term placentas after homogenization in 40 mM Tris (pH 7.4) and filtered through cheesecloth, followed by an initial centrifugation at 1,000×g for 10 minutes. The resulting supernatant was, again, centrifuged at 35,000×g for 30 minutes and the membrane pellet was collected and resuspended in Tris buffer with 0.3 M sucrose. The protein concentration was determined. Membranes were stored frozen at −20 C until use. Before use, placental membranes were diluted to 5,000 μg/mL with Tris buffer containing 0.5% BSA and 50 U/mL bacitracin. Placental membranes (100 μL) were used with varying concentrations of mammalian GnRH, Buserelin, chicken II GnRH, D-Arg(6)-chicken II GnRH-des-Gly(10)-ethylamide (SEQ ID NO: 2), or D-Arg (6)-chicken H GnRH-aza-Gly (10)-amide (SEQ ID NO: 2) (100 μL) and either radiolabeled Buserelin or radiolabeled D-Arg(6)-chicken II GnRH-aza-Gly(10)-amide (100 μL)/tube and iodinated). Following incubation at room temperature for 4 hours, the bound and free hormones were separated using polyethylene glycol precipitation, followed by centrifugation. The binding affinity for each GnRH isoform or analog was calculated using the double reciprocal plot of bound versus free ligand. Each study was done using three different human term placental tissues.

Figure 2:
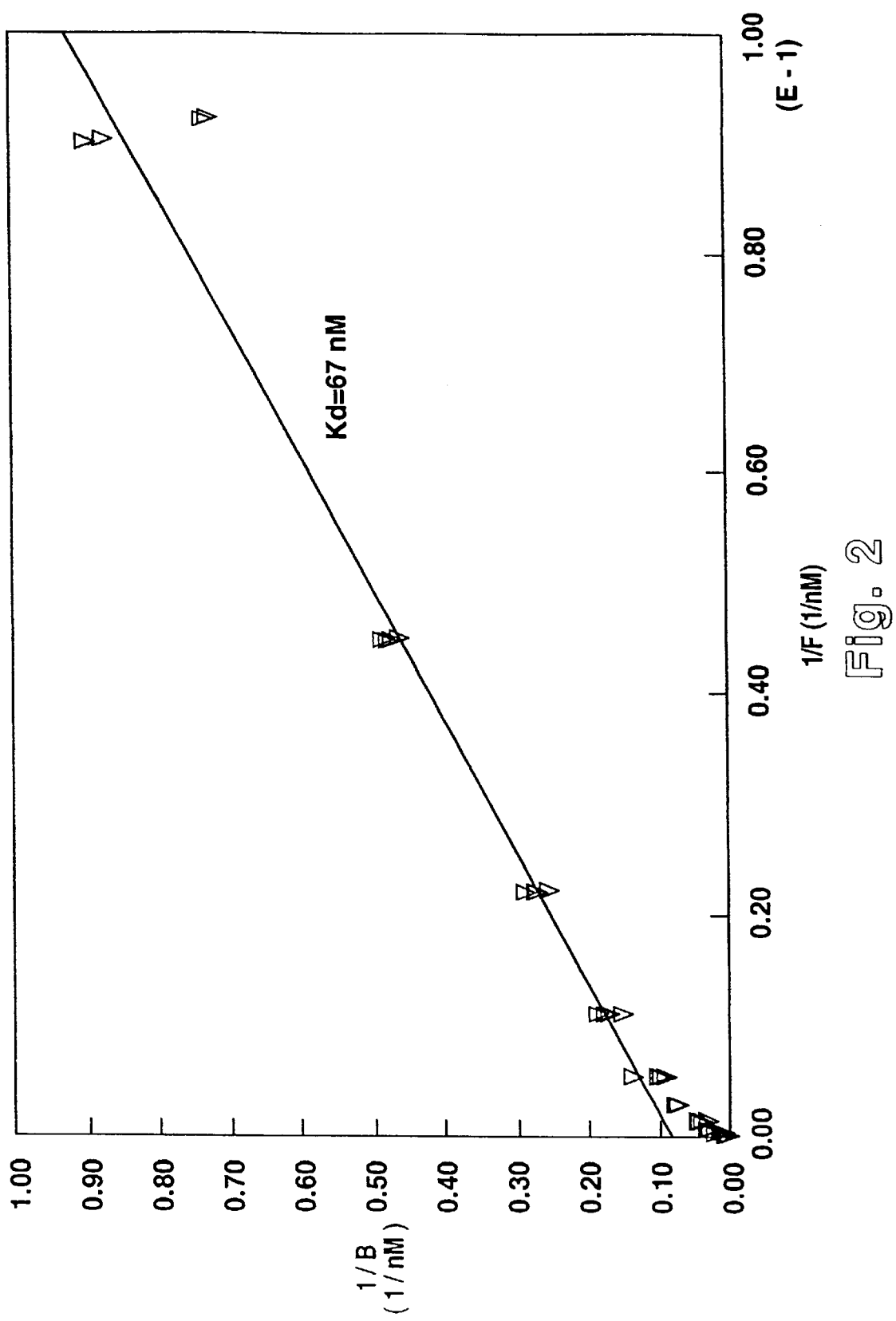
FIG. 2. Affinity of Receptor Binding of D-Arg(6)-Chicken II GnRH-aza-Gly(10)-amide for the Human Placental GnRH Receptor.

The receptor binding of mammalian and chicken II GnRH isoforms and their analogs were studied using the Buserelin label, and chicken II GnRH was equipotent to Buserelin and both were three-fold more potent than mammalian GnRH. The receptor binding for D-Arg-chicken II GnRH-aza-Gly-amide (SEQ ID NO: 2) with the Buserelin label, exhibited a dissociation constant (Kd) of 175±59 nM (2 fold greater than its natural chicken II GnRH isoform or Buserelin and 60 fold that of mammalian GnRH). When D-Arg-chicken II GnRH-aza-Gly-amide analog (SEQ ID NO: 2) was used as a label, the affinity for the placental GnRH receptor was enhanced 2 fold and that for mammalian GnRH was decreased 1.5 times. FIG. 1 compares the average Kd observed for the three different placental membrane preparations for mammalian GnRH, Buserilin, D-Arg(6) chicken H GnRH-aza-Gly(10)-amide (SEQ ID NO: 2) using the D-Arg(6)-chicken II GnRH-aza-Gly-amide radiolabeled analog. The most potent affinity constant was observed for the D-Arg(6)-chicken II GnRH -aza-Gly(10) amide analog (SEQ ID NO: 2), having a Ks of 68 nM when using the placenta 2 membrane preparation as illustrated in FIG. 2. The average binding affinity for this analog was 93±23 nM (25 fold that observed for mammalian GnRH).

Example III

Placental Stability Studies of GnRH Analogs

The present example demonstrated the utility of using the present invention in controlling and modulating the activity of the placenta, such as in a placenta of a pregnant mammal.

Mammalian GnRH and its analogs bind to placental receptors. The present non-mammalian analogs had not been examined for placental receptor binding. However, the added stability of these non-mammalian analogs, would effect a substantial increase in bioactivity alone. Thus, both stability and binding studies were performed.

Chorionic Peptidase-1 Stability Studies: The enzymatic degradation of the non-mammalian GnRH analogs were studied using the C-ase-1 enzyme activity assay as well as whole placental homogenate assays.

A chorionic peptidase activity that actively degrades GnRH in the placenta, named chorionic peptidase-1 (C-ase-1), was used. This enzyme acts as a post-proline peptidase, and is present in the placenta and in maternal circulation. In a non-pregnant individual very little post-proline peptidase activity is present in blood. Thus, currently available mammalian GnRH analogs have not been designed to be resistant to degradation by this activity. Non-mammalian GnRH analogs were designed with these specific criteria in mind. The stability of these non-mammalian GnRH analogs to the enzymatic activity of C-ase-1 and in placental homogenate was examined. In addition, the ability of the analogs to competitively inhibit the degradation of mammalian GnRH by C-ase-1 was studied.

Method and Analysis: The stability of most potent receptor-active non-mammalian GnRH analogs in the presence of C-ase-1 and placental homogenate was identified. Using the incubation system developed for the C-ase-1 activity, the degradation of each analog was tested. This method has previously been used by the investigator to determine the degradation of GnRH by C-ase-1. Siler-Khodr T M, Kang I S, Jones M A, Harper M J K, Khodr G S, Rhode J 1989 Characterization and purification of a placental protein that inactivates GnRH, TRH and Angiotensin 11. Placenta 10:283–296. Each of these analogs was then studied for their ability to act as a competitive inhibitor of non-mammalian GnRH for C-ase-1 activity. These studies were done using the C-ase-1 enzyme activity assay as described previously. In this assay, incubation of enzyme and mammalian GnRH with and without the chosen newly synthesized non-mammalian GnRH analog was studied. The reaction was stopped by heating, and the remaining mammalian GnRH substrate was quantified by radioimmunoassay. The product formed was calculated by subtraction, and its inverse plotted against the averse of the original substrate concentrations to determine the nature of the competition. The $K_i$ was to be determined by plotting the inverse of the product that formed verses the inhibitor used.

Figure 3:
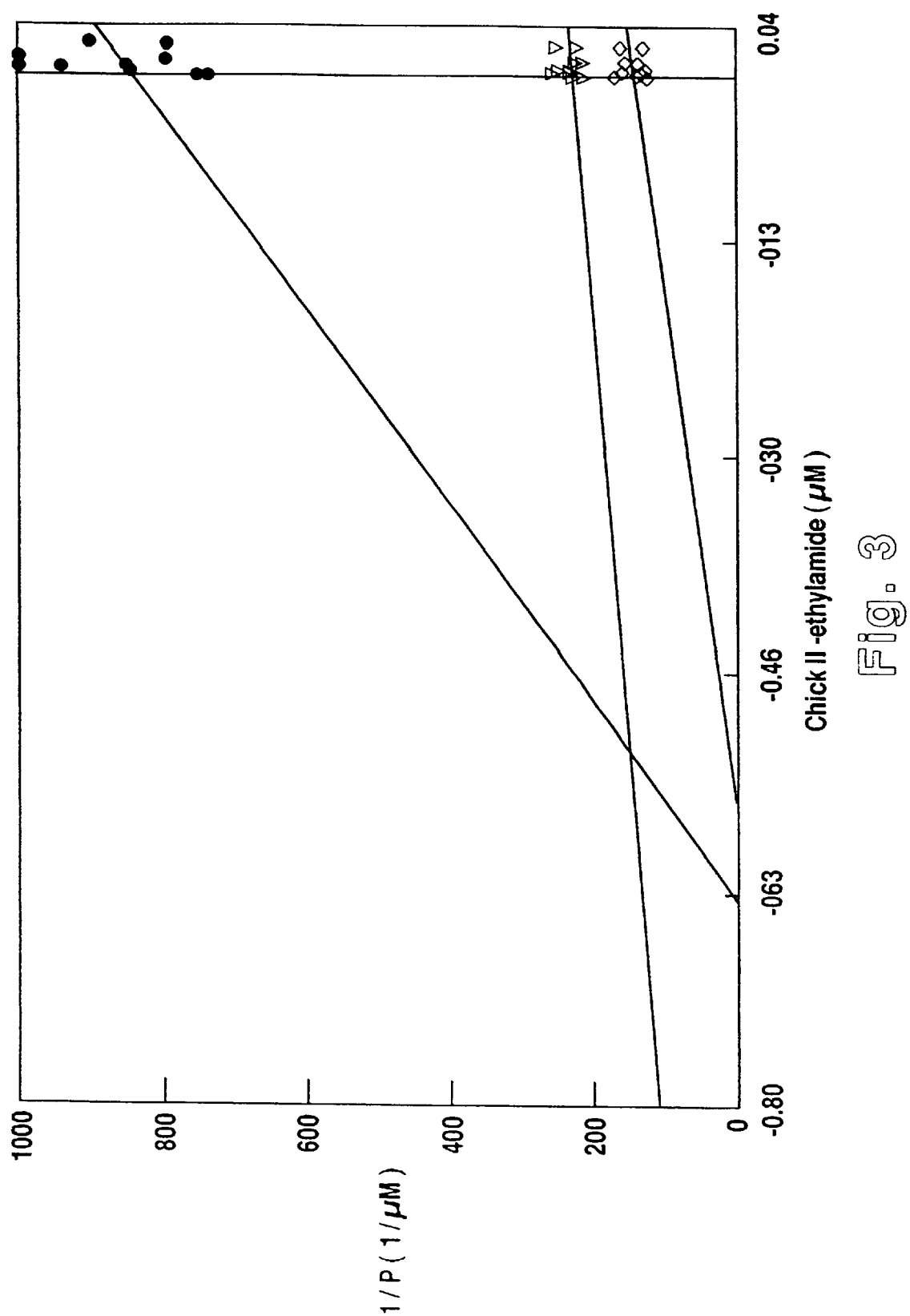
FIG. 3. Effect of des-$Gly^{10}$-GnRH-ethylamide on Degradation of GnRH by C-ase-1.
●GnRH 0.050 M, ○ GnRH 0.0250 M, ▽ GnRH 0.012 M, ◇ GnRH 0.062 M FIG. 4a. Inhibition of the Degradation of Mammalian GnRH by Placental Enzyme Chorionic Peptidase-1 by Chicken II GnRH.

Studies using whole placental homogenate were also performed. The enzymatic degradation of mammalian GnRH was studied as described above, replacing C-ase-1 with placental homogenate. The competition by the newly synthesized non-mammalian GnRH analogs as compared to mammalian GnRH was then studied to confirm the C-ase-1 studies above. Similar patterns of inhibition using placental extracts demonstrated the dominance of the C-ase-1 activity in the degradation of GnRH during pregnancy. (FIG. 3)

Although the enzyme competition system had already been developed, newly synthesized non-mammalian GnRH analogs have not been utilized in these systems. Previous data generated by the present inventor has demonstrated that the antiserum is specific for mammalian GnRH, thus reducing potential for cross-reaction of non-mammalian GnRH or its analogs in the assay used in these studies.

In these and additional studies, competition for the enzymatic degradation of mammalian GnRH by a post-proline peptidase was studied by determining the remaining GnRH after incubation of varying concentrations of mammalian GnRH with a highly active post-proline peptidase, C-ase-1, isolated from term human placentas, in the presence or absence of varying concentrations of other GnRH isoforms or analogs. The remaining GnRH was measured using a radioimmunoassay specific for mammalian GnRH having less than 0.1% cross-reactivity for any of the analogs or isoforms tested. The concentration of the product of the degraded GnRH was quantified by subtracting the remaining mammalian GnRH from the starting concentrations of mammalian GnRH. Analogs and isoforms of GnRH studied were Buserelin, Leuprolide, chicken II GnRH and, its D-Arg (6), Des-Gly(10) GnRH -ethylamide, and its D-Arg (6), aza-Gly (10)-amide (SEQ ID NO: 2) analogs. The Ks for the degradation of mammalian GnRH was calculated from the x axis intercept using Lineweaver-Burke double reciprocal plot of the concentration of the product formed versus the concentration of the substrate used. The inhibitor constant Ki was also calculated from the point of converging lines formed from the plot of the concentration of the product formed using a given concentration of mammalian GnRH in the presence of different concentrations of competing analogs or isoform.

The Ks for mammalian GnRH degradation by C-ase-1 was ~30 nM. Using the reciprocal plot of the product versus the concentration of the GnRH isoform or analog to determine the Ki, it was determined that Buserelin was degraded by C-ase-1, although at one fourth the rate of its native mammalian GnRH isoform (Ki of 110 nM). Chicken II GnRH competed for the degradation of mammalian GnRH with a Ki of 200 nM (one-sixth that of the mammalian GnRH). The D-Arg-chicken II GnRH-ethylamide (SEQ ID NO: 2) had a Ki of more than 200 nM and D-Arg(6)-aza-Gly(10) amide analog (SEQ ID NO: 2) of chicken II GnRH was essentially not degraded (Ki of >400 nM). The inhibition of the degradation of mammalian GnRH by the placental enzyme, chorionic peptidase 1, is shown in more detail in FIGS. 4a, b, and c.

EXAMPLE IV

Biological Activity Studies

The hCG inhibiting activity of the chorionic GnRH analogs was studied using an in vitro human placental explant system. The present example demonstrates the utility of using the present non-mammalian analogs to regulate hCG levels in a mammal and in the regulation of pregnancy.

The newly synthesized non-mammalian GnRH analogs are resistant to enzyme degradation and are potent binders of the placental GnRH receptor. Bio-potency was studied using a placental explant system, and by determining the release of hCG, progesterone and prostanoids. hCG is the luteotropin of pregnancy, and known to be critical to the maintenance of the corpus luteum during pregnancy. Thus, it is a primary parameter of interest. The production of progesterone by the placenta and the ovary is affected by hCG, as well as being independently regulated by a GnRH-like substance. Progesterone is primary to the maintenance of uterine quiescence and thus the maintenance of pregnancy, and therefore is of primary interest to these studies. Also, of interest is the effect of these GnRH analogs on prostaglandin production. Prostaglandins are required for abortifacient activity, and thus, the maintenance or increase in their production may be necessary for the proposed action of the analogs.

Method and analysis: The biological activity of the newly synthesized non-mammalian GnRH analogs was studied using a static implant culture system. This system allows for inexpensive extended activity studies. Mammalian GnRH action on the human placenta release of hCG, progesterone and prostaglandins were defined using this system. Siler-Khodr T M, Khodr G S, Valenzuela G, Rhode J 1986 Gonadotropin-releasing hormone effects on placental hormones during gestation: II. Progesterone, estrone, estradiol and estriol. Biol Reprod 34:255–264; Siler-Khodr T M, Khodr G S, Valenzuela G, Rhode J 1986 Gonadotropin-releasing hormone effects on placental hormones during gestation: 1 Alpha-human chorionic gonadotropin, human chorionic gonadotropin and human chorionic somatomammotropin. Biol Reprod 34:245–254; Siler-Khodr T M, Khodr G S, Valenzuela G, Harper J, Rhode J 1986 GnRH effects on placental hormones during gestation. 111 Prostaglandin E, prostaglandin F, and 13, 14-dihydro-15-keto-prostaglandin F. Biol Reprod 35:312–319. Replicate cultures were studied, thus allowing for comparison of different doses of each non-mammalian GnRH analog to mammalian GnRH, as well as direct competition assays. In these studies, the action of the most stable and receptor-active chorionic GnRH analogs on hCG, progesterone and prostaglandin $E_2$ were determined in the spent media using specific sensitive radioimmunoassays. These studies were repeated using different human placentas.

Using an in vitro system to define bio-potency is expected to be predictive of in vivo activity. In addition to placental action, these newly synthesized non-mammalian GnRH analogs are also expected to act directly at the corpus luteum to inhibit steroidogenesis. These analogs are also expected to be active at the ovarian level.

In these and additional studies, an explant culture system was used to determine the effect of mammalian GnRH, chicken II GnRH, or the D-Arg(6)-chicken II GnRH-aza-Gly(10)-amide analog (SEQ ID NO: 2) on the release of the hCG, progesterone, and prostaglandin $E_2$. Human term placentas were dissected free of membranes, minced into fragments of 5 mm, rinsed in medium, and a total weight of ~100 mg (20 explants) was placed on a sterile filter paper resting on an organ culture grid such that they touched the surface of the culture medium, but were not immersed in it. Gibbons J M, Mitnick M, Chieffo V 1975 In vitro biosynthesis, of TSH- and LH-releasing factors by the human placenta. Am J Obstet Gynecol 121:127–131. The medium contained penicillin, streptomycin, and fungizone at 100 U/mL, 100 μg/mL, and 2.5 μg/mL respectively with and without varying doses of GnRH isoforms or analogs was added to each Petri dish. Triplicate chambers for each media were made and incubated at 37 C in a humidified chamber with an atmosphere of 5% $CO_2$ and 95% air. Spent media were collected and replaced after 2 hours, 24 hours, and 48 hour of culture and stored frozen at −20° C. until assayed for hormones. HCG, progesterone, and $PGE_2$ were measured using specific double antibody procedures as described previously. The chicken II GnRH analog (SEQ ID NO: 2) was studied using four different human term placentas, and the native chicken II GnRH isoform was also studied using one human term placenta.

Figure 5A:
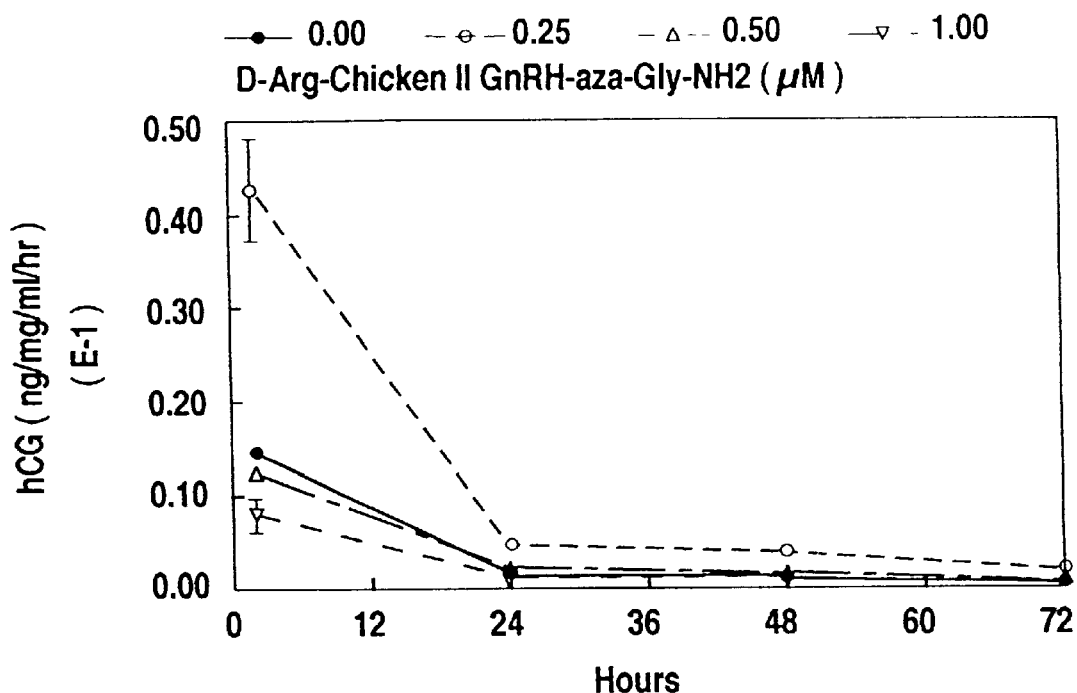
Figure 5B:
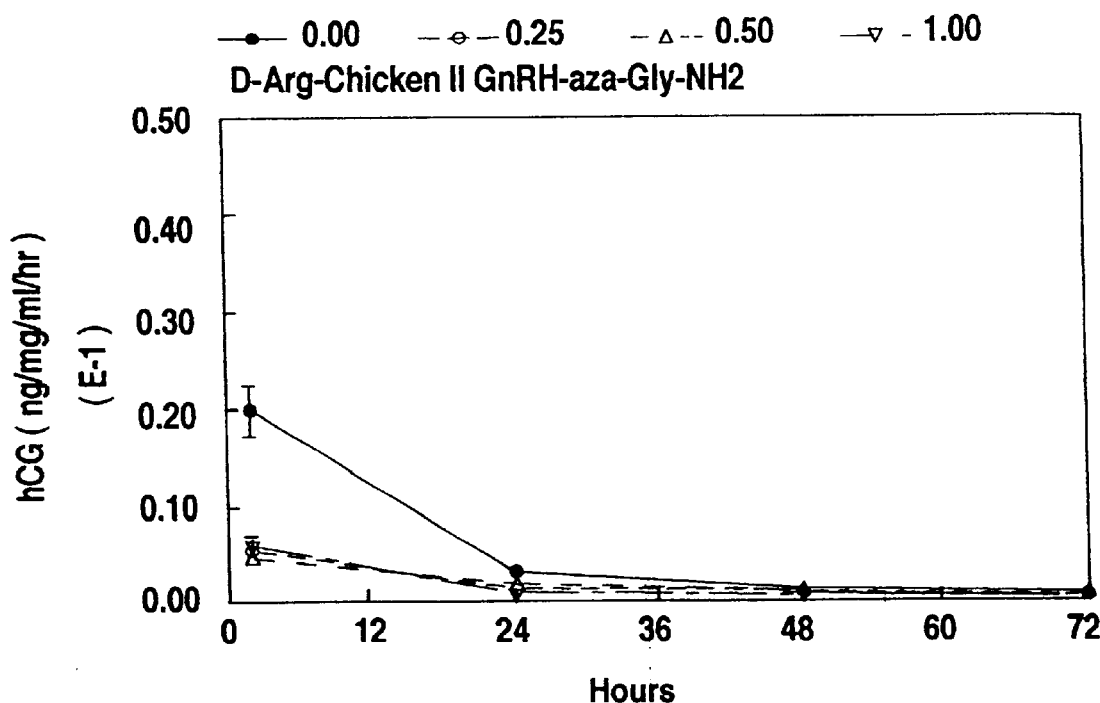

The biopotency of the D-Arg(6) chicken II GnRH-aza-Gly(10) amide analog (SEQ ID NO: 2) was compared with that of mammalian GnRH. The basal release of hCG and progesterone declined after the first day of culture, yet $PGE_2$ increased throughout the culture period. The addition of mammalian GnRH (0.25–1.00 μM) to the media had no significant effect on the release of hCG from four different placentas studied. Progesterone release was not affected by mammalian GnRH in two of four placentas, but in one placenta it was significantly increased and in the other was decreased. The addition of D-Arg-chicken II GnRH-aza-Gly-amide (SEQ ID NO: 2)(0.25–1.00 μM) resulted in as much as a three fold stimulation of hCG during the first two hours of exposure using the lowest concentration of analog tested (250 nM) as illustrated in FIGS. 5a and 5b. However, the response to D-Arg-chicken II GnRH-aza-Gly-amide (SEQ ID NO: 2) was biphasic i.e. an inhibition of hCG was observed using the higher concentrations (1–9 μM) of the chicken II GnRH analog. After 24 hours and 48 hours of incubation with this analog, a similar pattern of response was observed, even though basal hCG release had fallen 10- to 20-fold during the 2 days in vitro. A significant dose-related inhibition of hCG release (P<0.05) was observed after 2, 24, and 48 hours of treatment with the D-Argchicken II GnRH-aza-Gly-amide (SEQ ID NO: 2) as indicated in FIGS. 6 and 7. The progesterone release was also inhibited when incubated with the higher concentrations of this analog, but not as markedly as hCG in FIG. 8. $PGE_2$ was not significantly changed by exposure to this analog as indicated in FIGS. 9a and b.

The hCG inhibiting activity of the GnRH analogs was studied using an in vitro human placental explant system. The newly synthesized GnRH analogs are resistant to enzyme degradation and one potent binders of the placental receptor. The bio-potency was done with a placental explant system, and the release of hCG, progesterone and prostaglandin $E_2$ was assessed. hCG is the luteotropin of pregnancy and know to be important in the maintenance of the corpus luteum during pregnancy. The production of progesterone by the placenta is affected by hCG, and may be independently regulated by GnRH as well. Progesterone is primary to the maintenance of uterine quiescence and thus the maintenance of pregnancy. Of interest was the effect of these GnRH analogs on prostaglandin production. Prostaglandins are required for abortifacient activity.

These studies were done using the D-Arg(6)-chicken II GnRH-aza-Gly(10)-amide analog (SEQ ID NO: 2). Three different placentas have been used for these studies and the data analysis of one of these placental culture sets is attached.

An inhibition of hCG was observed with this analog regardless of the concentration of exogenous GnRH. The lower dose of analog was the most effective in this particular study. Progesterone response to this analog was similar to hCG.

These data demonstrate the complexity of a system having multiple types of GnRH receptors. D-Arg(6)-chicken II GnRH analog-$NH_2$ has bioactivity in the regulation of hCG and progesterone in the human term placenta.

These studies demonstrate specific binding of GnRH analogs to the human GnRH placental receptor, which is unique from the pituitary receptor. The most potent analogs were chicken II GnRH derivatives, particularly the D-Arg (6)-chicken II GnRH-aza-Gly$^{10}$ $NH_2$ (SEQ ID NO: 2). This analog may be used in the regulation of chorionic GnRH activity.

EXAMPLE V

Inhibition of Chorionic Peptidase-1 (C-ase-1) Activity by Analogues of GnRH

The present example demonstrates the isolation of an enzyme from human placentas, and the action of the enzyme as a post-proline peptidase. It actively degrades peptides, such as gonadotropin releasing hormone (GnRH), thyrotrophin releasing hormone (TRH), reduced oxytocin, and Angiotensin II (Ang-II). See FIGS. 10, 11, 12A, and 12B. These peptides contain a proline residue where the chorionic peptidase-1 (C-ase-1) is to cleave its C-terminal peptide bond.

The present example also defines enzyme inhibitors of C-ase-1 action on GnRH, such that it might regulate GnRH concentrations within the intrauterine tissues.

C-ase-1 enzyme activity studies were done by incubating GnRH with C-ase-1 in the presence of varying concentrations of the non-mammalian GnRH analogs. The reaction was stopped by heating at 85° C. for 10 minutes. The remaining GnRH was determined using a specific radioimmunoassay. The formation of product, i.e., the N-terminal nonapeptide of GnRH, was calculated by subtraction and its inverse was plotted versus the inverse of the initial substrate to determine the $K_s$ of the reaction. The inhibitory activity of Antide, $^6$Im-btl-D-His-GnRH-$^{10}$ ethylamide, $^9$OH-Prl-GnRH, chicken II GnRH-$^{10}$ ethylamide, chicken II GnRH, chicken I GnRH, salmon GnRH and lamprey GnRH was studied. The relative potency of each analog was compared.

GnRH was actively degraded by C-ase-1. This activity of C-ase-1 was inhibited by, $^9$OH-Pro-GnRH, lamprey, chicken I-GnRH, Antide, chicken II-GnRH and salmon GnRH with a relative potency of 1.5, 1.5, 0.6, 0.6, 0.2 and 0.2, respectively, compared to that for GnRH.

Chorionic peptidase-1, which is a post-proline peptidase with high specificity for the degradation of GnRH, can also degrade other GnRH species. The synthetic mammalian GnRH analogs such as antide (see FIG. 13) are degraded with reduced activity, while other analogs such as chicken II GnRH-$^{10}$ aza-Gly-amide and $^6$IM-btl-D-His-GnRH$^{10}$ ethylamide are resistant to degradation by this endogenous chorionic enzyme. See FIG. 14. These analogs will be useful in the regulation of chorionic GnRH activity.

EXAMPLE VI

Comparison of GnRH and its Synthetic and Naturally Occurring Analogs for Binding Action in the Human Placental Receptor The human placental GnRH receptor shows different kinetic constants for GnRH compared to that of the pituitary receptor. The relative decreased potency of GnRH at the placental receptor, together with it rapid degradation in chorionic tissue, leads to question if it is indeed the active sequence for the chorionic receptor.

Studies were designed to compare the human placental receptor activity for numerous synthetic and naturally occurring analogs.

Receptor assays were performed by incubating human term placental GnRH receptors with varying concentrations of GnRH or its analogs in the presence of $^{125}$I-Buserelin. The reaction was stopped and the bound hormone precipitated with polyethylene glycol. Following centrifugation the receptor binding activity was calculated and compared for GnRH, $^6$Im-btl-D-His-GnRHR$^{10}$ ethylamide and $^6$D-Trp-GnRH-$^{10}$ ethylamide, chicken II-GnRH and chickenII GnRH-$^{10}$ ethylamide. GnRH was bound by the placental GnRH receptor with a $K_d$ of $10^{-6}$ M. Chicken II GnRH was similar to GnRH. The $K_d$ for $-^6$Im-btl-D-His-GnRH$^{10}$ ethylamide was half the potency of GnRH, while Buserelin and $^6$D-Trp-GnRH-$^{10}$ ethylamide were twice as active as GnRH. The greatest potency was for chicken II GnRH ethylamide, having a $K_d$ of 30 non-mammalian, i.e. 33-fold more activity than GnRH. See FIG. 15.

EXAMPLE VII

GnRH and Stability Thereof in the Presence of C-ase-1

Fifteen GnRH analogs were examined for their stability in the presence of C-ase-1 and placental homogenate. Using the incubation system developed for the C-ase-1 activity, the degradation of each analog was studied. Previously, this method was used to determine the degradation of GnRH by C-ase-1. Each of these analogs was studied for their ability to act as competitive inhibitors of GnRH for C-ase-1 activity (Table 1). The inverse of the product was plotted against the inverse of the original substrate concentrations to determine Ks of the competition. The $K_i$ was determined by plotting the inverse of the product formed verses the inhibitor used. The placental homogenate studied, demonstrated a similar pattern having $K_i$ three-fold greater than that for C-ase-1.

OH-Pro(9)-GnRH and lamprey GnRH were determined to be better competitors for GnRH degradation by C-ase-1. They are as or even more potent than GnRH. Antide and chicken I GnRH are three-fold less potent than GnRH, but two-fold more potent than the salmon or chicken II GnRHs defined here. The addition of the ethylamide to GnRH, with or without the D-Trp(6)-, D-Phe(6) substitution, decreased the competition with GnRH for C-ase-1 degradation, but not as markedly as did the Im-Btl-D-His(6) or chicken II GnRH-ethylamides. Ethylamides of the latter two GnRHs were greater than 200-fold less active in the inhibition of GnRH degradation by C-ase-1. Thus, these ethylamides appear to be very stable in the presence of the C-ase-1 enzyme. The Im-Btl-His(6) analog has reduced receptor potency. The stability of the D-Arg-(6)-chicken II GnRH aza-Gly-amide (SEQ ID NO: 2) was found to be at lease 200-fold that of GnRH.

The stability of these analogs in the present of whole placental homogenates was examined. The ethylamide derivative has a slowed degradation rate as compared to GnRH, but can be degraded. Chicken II and its ethylamide analog are more stable than the mammalian GnRH analogs analyzed to date.

EXAMPLE VIII

Non-Mammalian GnRH and Methods for Maintaining Pregnancy

The present example defines a method by which the present invention may be used to maintain pregnancy in a pregnant mammal. The mammal in some embodiments is a pregnant human. As a proposed dose regimen, it is anticipated that a pregnant female between 100 lbs and 150 lbs would be administered about 10 nanogram to 1.0 gram of chicken II GnRH Analog (SEQ ID NO: 2) or salmon GnRH analog (SEQ ID NO: 4). This would be expected to be effective for promoting the maintenance of pregnancy in the mammal when administered.

In some embodiments, the dosing regimen will comprise a pulsatile administration of the chicken II GnRH over a 24-hour period, wherein the daily dosage is administered in relatively equal $1/24^{th}$ fractions. For example, where the daily dose is about 2.4 micrograms, the patient would be administered about 0.1 micrograms per hour over a 24-hour period. Such a daily pulsatile administration would create a hormonal environment in the patient sufficient to maintain pregnancy. The particular pharmaceutical preparations may be created by one of skill in the pharmaceutical arts. Remington's Pharmaceutical Sciences Remington: The Science and Practice of Pharmacy, $19^{th}$ edition, Vol. 102, A. R. Gennaro, ed., Mack Publishing Co. Easton, Pa. (1995), is specifically incorporated herein by reference for this purpose.

EXAMPLE IX

Non-mammalian GnRH Analogs and Post Coital Contraception, Menses-Inducement

The present example demonstrates the utility of the present invention for use as a post-coital contraceptive preparation.

By way of example, the analogs defined here, and conservative variants thereof, may be formulated into a pharmaceutically acceptable preparation, and then administered to a female mammal having been inseminated during the prior 24 to 72 hours (prior 1 to 3 days). Relatively high doses of about 0.1 gram to about 10 grams of the non-mammalian GnRH analog would be given daily for 2 to 5 days, on the average about 3 days.

To induce menses, it is anticipated that a dose of between 0.1 grams micrograms to 10.0 grams for 3 days would be adequate to commence menses in the female mammal.

For purposes of practicing the present invention as an oligonucleotide in molecular biology applications, the non-mammalian GnRH analogs of chicken II (SEQ ID NO: 1) and salmon decapeptide GnRH analog cDNA sequences (SEQ ID NO: 3) would be employed. The textbook of Sambrook, et al (1989) *Molecular Cloning, A Laboratory Manual*, 2d Ed., Cold Springs Harbor Laboratory, Cold Springs Harbor, N.Y., is specifically incorporated herein by reference for this purpose. By way of example, the cDNA sequence for the non-mammalian GnRH of SEQ ID NO: 1 (chicken II GnRH) or SEQ ID NO:3, (salmon GnRH) may be prepared as part of a suitable vector, such as in an adenovirus or retroviral vector, and administered to the animal. Once the sequence is incorporated into the cell, the peptide product will be translated and peptide supplied. Because this method of treatment would not require that the peptide travel in the blood circulation in order to reach the site of action, there would be no requirement that the analog possess enzyme degradation resistance. This mode of treatment has not thus far been proposed, and hence the use of such a method in the regulation of female fertility is a novel clinical regimen. The non-mammalian analogs are also contemplated to be useful to directly affect the ovary. By way of example, this technique renders the system useful as a contraceptive. As a contraceptive, the non-mammalian GnRH analog would be given daily from the start of ovulation and continue 8 days to two weeks, stopping with onset of menses. In addition, it is contemplated that the activity of the analogs would prove useful in the treatment of ovarian conditions, such as polycystic ovarian disease and ovarian cysts.

EXAMPLE X

Antibodies Specific for Non-Mammalian GnRH

The present example demonstrates the utility for using the present invention non-mammalian GnRH analog decapeptides to prepare antibodies that preferentially bind the GnRH peptide sequences, or that bind the ovarian, placental or any other non-pituitary GnRH peptide or protein, or the receptors therefor. It is anticipated that these non-mammalian GnRH analog antibodies may be used in a variety of screening assays. For example, these antibodies may be used to determine levels of GnRH, or the GnRH receptor, are present, in a sample as an indicator molecule. The levels of such GnRH may be used to monitor and follow a patient's pregnancy, as well as an indicator of the length of gestation. The antibodies to non-mammalian GnRH may be monoclonal or polyclonal antibodies.

Polyclonal antibodies may be created by standard immunization techniques, wherein the immunogen used will be the non-mammalian chicken-II GnRH analog or the salmon GnRH analog decapeptide described herein. These peptides may be used either alone or together in a pharmaceutically acceptable adjuvant. The animal, such as a rabbit, would be administered several doses of the decapeptide preparation, and the levels of the animal's antibody blood levels monitored until an acceptable antibody level (titer) had been reached.

For the preparation of monoclonal antibodies, one would follow standard techniques for the immunization of an animal, again using the decapeptide non-mammalian GnRH peptide. Once sufficiently high acceptable antibodies are reached (titer) in the animal, the spleen of the animal would be harvested, and then fused with an immortalized cell line, such as a cancer cell line, to produce a population of hybridoma cells. This hybridoma population of cells would then be screened for those that produce the highest amount of antibody that specifically bind the non-mammalian GnRH analog decapeptide. Such hybridoma cells would be selected, and then cultured. The antibody to non-mammalian GnRH would then be collected from the media of the cell culture using techniques well know to those of skill in the art.

For purposes of the practice of preparing polyclonal and monoclonal antibody, the textbook Sambrook et al (1989) *Molecular Cloning, A Laboratory Manual*, $2^{nd}$ Ed., Cold Springs Harbor Laboratory, Cold Springs Harbor, N.Y., is specifically incorporated herein by reference. All of the compositions and methods disclosed and claimed herein can be made and executed without undue experimentation in light of the present disclosure.

EXAMPLE XI

HCG Stimulating and Inhibiting Activity of the Non-Mammalian GnRH Analogs

The acute activity of the chicken II GnRH analogs on hCG release was studied using a human placental explant perifusion system. Prior studies have demonstrated the long term effect of these newly synthesized GnRH analogs and their biological action using a static culture system. A dose-related biphasic response was noted over time. In the perifusion studies, the dynamic of the response to continuous exposure of the chorionic GnRH agonist can be better defined. The system better emulates the in vivo situation and provides a better understanding of the effect of the analogs on chorionic hormonogenesis and the applicable dose appropriate for future studies.

Chicken II GnRH analog with D-Arg at position 6 and aza-Gly-amide at position 10 (SEQ ID NO: 2) and commercially available mammalian GnRH agonist, Buserelin, were used in four different placental perfusion studies. Placental tissues that are normally discarded were obtained from unidentified patients following first trimester pregnancy termination (early human placental explants). Tissue fragments, dissected of vessels and membranes, were placed in a perfusion system for study of 20 replicate chambers of the same tissue. This allows for simultaneous dose-response studies to be performed. To achieve this specific aim, explants from a given placenta were placed in 20 replicate chambers and perfused with basal medium for three hours at a rate of 6 ml/hr (dead volume of the system at 6 ml/hr is ten minutes). After three hours of equilibration, the analog was added to the basal perfusing medium. Quaduplicate chambers were made for chicken II GnRH analog (SEQ ID NO: 2) at 0, $10^{-9}$, $10^{-8}$, $10^{-7}$, $10^{-6}$ M and Buserelin at $10^{-7}$ M. The effluent medium of each chamber was collected after a three hour equilibration period. Two basal samples, at half hour intervals were collected, media with test substances was initiated and effluent medium collection continued for four and one half hours at thirty minute intervals. The hCG release was analyzed in each of these experiments. FIGS. 16 and 17 illustrate a typical response. A dose related biphasic response was observed. Maximal response was observed within minutes after initiation of perfusion at $10^{-8}$ M, with possible down regulation beginning after five hours at $10^{-6}$ M as illustrated in FIG. 18. The integrated response over the 4.5 hours of perfusion also demonstrated the biphasic response with maximal stimulated response using $10^{-8}$ M of this analog as seen in FIG. 19.

In additional experiments, early gestation human placentas were perfused for six hours with medium supplemented with estradiol, progesterone, bovine serum albumin, and antibiotics (basal medium). Twenty replicate chambers were perifused with basal medium for two hours, then triplicate chambers were perifused with the medium containing either Buserelin, or $10^{-9}$, $10^{-8}$, $10^{-7}$, $10^{-6}$ M of a chicken II GnRH analog (SEQ ID NO: 2), leaving five control chambers. The eluted medium was collected at thirty minute intervals, starting one hour prior to the addition of GnRH analogs and throughout five hours of treatment. hCG released into the effluent media, as well as the production of GnRH, were measured using sensitive and specific radioimmunoassays. The release of hCG at each time point was normalized to its zero treatment release and the release throughout the treatment period and its average release was compared for various treatment regimens. These studies were repeated using tissues from three different first trimester placentas. The results of this experiment are illustrated in FIG. 20.

hCG release from control chambers decreased over the five hours of treatment to approximately 60% of its initial release. The addition of varying concentrations of chicken II GnRH (SEQ ID NO: 2) analog to the perifusing media resulted in a biphasic stimulation of hCG from these early placental tissues. The greatest response has been observed using $10^{-8}$ M of this chicken II analog (SEQ ID NO: 2). The response decreased with increasing concentrations of the chicken II analog. Incubation with Buserelin, the mammalian GnRH analog, at $10^{-7}$ M resulted in a small stimulation of hCG at early time points. The average stimulation of hCG release throughout the five hours of perifusion was 150% that of the control tissues.

These studies have led to the definition of the action of chicken II GnRH and newly designed analogs on placental, ovarian, endometrial, and pituitary tissues. It has been shown that these analogs are capable of inhibiting hCG and progesterone production in placental tissues after extended exposure. A direct action on ovarian and/or endometrial tissue was demonstrated. A potential direct contraceptive action of these analogs, as well as their placental hCG and steroidogenic suppression activity is indicated. Such analogs could be used as a menses regulator, contraceptive, abortifacient or in any other manner to function in regulating reproductive function and disorder and would be valuable agents in population control.

EXAMPLE XII

Receptor Binding Activity of Non-Mammalian GnRH Analogs at Ovary and Uterus

The receptor binding activity of newly synthesized chorionic GnRH analogs was studied in ovarian, uterine, and pituitary tissues.

There is an ovarian, tubal, and uterine receptor for GnRH which is distinct from that in the pituitary. The currently defined mammalian GnRH analogs have been designed for activity at the pituitary receptor. These analogs do not demonstrate high potency for the ovarian, tubal, or uterine receptor. The analogs of the present invention have high affinity for the ovarian, tubal, uterine, and placental receptor and limited degradation by the chorionic enzyme C-ase-1. A similar receptor and enzyme appears to be acting in the ovary and uterus, but not the pituitary. The present study was designed to define the receptor binding of newly synthesized GnRH analogs in the ovary, uterus, and the pituitary and to compare them to the receptor binding of the mammalian GnRH analogs.

The receptor binding activity of newly synthesized GnRH analogs was studied in ovarian and uterine tissues. Synthesized chicken GnRH analogs with D-Arg at position 6 and aza-Gly at the 10 position (SEQ ID NO: 2) and commercially available mammalian GnRH, chicken II GnRH, and Buserelin were used in the receptor binding studies using three different baboon ovaries. The ovaries of the three baboons were extracted and the cytosolic and membrane fractions were recovered for the tissues. The membrane fraction from one animal was titred for GnRH receptor binding activity using D-Arg(6)-chicken II GnRH-aza-Gly (10)-amide radiolabeled ligand. Receptors were clearly demonstrable even at 4 µg membrane protein/tube. See FIG. 21. These tissues expressed a specific activity of binding for this analog which was about 50–100 fold more potent than the placental membrane preparations studied to date. The GnRH receptor affinity for this analog was found to be $10^{-8}$ M as indicated in FIG. 22. The chicken II GnRH analog (SEQ ID NO: 2) had the highest affinity for any GnRH analog reported to date. Mammalian GnRH was rapidly degraded by baboon ovarian cytosol fractions, yet the chicken II GnRH analog (SEQ ID NO: 2) was resistant to such degradation.

One study using human granulosa cells was performed and receptor binding for the GnRH analog was observed. Due to the limited number of cells it was not possible to precisely define the affinity of this receptor. In another study using baboon endometrium (stroma and epithelium) the chicken II GnRH analog (SEQ ID NO: 2) receptor affinity was found to be approximately 60 nM.

Baboon uterine tissue was also demonstrated to have a GnRH receptor with high binding affinity for the chicken II GnRH analog (SEQ ID NO: 2). These chicken II GnRH analogs (SEQ ID NO: 2) may have particular applicability for regulation of implantation and in uterine tissue conditions, such as endometriosis, abnormal uterine bleeding, and leiomyomas. Thus, high affinity receptors for chicken II GnRH have been defined in baboon ovary and uterus tissues.

EXAMPLE XIII

Stability of GnRH Analogs in Ovarian Homogenates

The stability of newly synthesized chicken II GnRH analogs (SEQ ID NO: 2) in ovarian, endometrial, and pituitary homogenates was determined using enzyme activity assays.

Chorionic peptidase which actively degrades GnRH in the placenta will be called chorionic peptidase 1 (C-ase-1). The enzyme acts as a post-proline peptidase and is present in maternal circulation. In non-pregnant individuals very little post-proline peptidase activity is present in the circulation. Thus, GnRH analogs in the prior art have not been designed to be resistant to this activity. These studies were designed to test the stability of these analogs to the enzymatic activity in ovarian tissue.

The stability of newly synthesized GnRH analogs in baboon ovarian homogenates was determined using an enzyme activity assay. More specifically, chicken II GnRH analogs with D-Arg at position 6 and aza-Gly amide at position 10 (SEQ ID NO: 2) were studied. In these studies the enzyme was in the ovarian extract. It was found that baboon ovary actively degrades mammalian GnRH as illustrated in FIG. 23. The endogenous peptidase specific activity in the degradation of GnRH was tenfold that of placental cytosolic fractions.

To determine the stability of the analog in the baboon ovary, an incubation system was used similar to that developed to study GnRH and its isoforms and analogs in the presence of chorionic tissues except baboon ovarian homogenates were substituted for C-ase-1. In this assay, following incubation of the enzyme and GnRH, with and without the chosen analog, the reaction was stopped by heating and the remaining GnRH substrate was quantified by radioimmunoassay. The product formed is calculated by subtraction, and its inverse plotted against the inverse of the original substrate concentrations to determine the nature of the competition. The Ki was determined by plotting the inverse of the product formed versus the inhibitor used. FIG. 24 illustrates the ability of D-Arg-6-chicken II GnRH-aza-Gly-amide (SEQ ID NO: 2) to act as a competitive inhibitor of GnRH for the baboon ovarian enzymatic activity. Since this analog did not significantly compete with this degradation of mammalian GnRH in the baboon ovary, it is therefore, for all essential purposes, stable in the baboon ovary. Three different ovaries were tested and similar results were obtained as illustrated in FIG. 24. It should be appreciated that the degradation of mammalian GnRH by ovarian tissues has a Ks of ~30 nM. The Ki of the chicken II GnRH analog (SEQ ID NO: 2) is greater than or equal to 1,500 nM. Thus, the stability of this analog is more than 50 times greater than that of mammalian GnRH.

EXAMPLE XIV

Bioactivity of Non-Mammalian GnRH Analogs on Ovarian Estradiol and Progesterone Production, Endometrial Prostallandin E2 ($PGE_2$) and on Pituitary Luteinizing Hormone (LH) Release The bioactivity of the newly synthesized GnRH analogs on ovarian estradiol and progesterone production, endometrial stromal prolactin and endothelial prostaglandin production and pituitary luteinizing hormone release was determined using ovarian, endometrial, and pituitary cell cultures.

It was anticipated that certain analogs tested in the stability and receptor assays would be active in culture. Their biological activity on hormone production, which is the ultimate parameter of function, was studied for each of the specifically designed analogs and compared to that of closely related pituitary analogs, such as mammalian GnRH and Buserelin.

The bioactivity of newly synthesized GnRH analogs and commercially available mammalian GnRH agonist Buserelin on ovarian steroid production, endometrial stromal and epithelial prostaglandin production and pituitary luteinizing hormone release was determined using baboon and human granulosa cells, human endometrial, both epithetial and stromal cell lines and pituitary cell cultures, respectively, from rats and baboons. Using analog concentration of $10^{-7}$ M, baboon LH was not stimulated, but an increase in rat LH was observed for the respective pituitary cell cultures as indicated in FIG. 25. The dose-response action of this analog ($10^{-6}$ to $10^{-9}$ M) on two different baboon pituitaries has now been analyzed and the results recorded in FIG. 26.

Ovarian cell cultures from two different pregnant rats were completed and an inhibition of progesterone production was observed as seen in FIG. 27.

The biopotency of chicken II GnRH analogs (SEQ ID NO: 2) in the regulation of baboon ovarian function was studied. The effect of mammalian and chicken II GnRH analogs (SEQ ID NO: 2) on ovarian progesterone release was studied using granulosa cell cultures. The dose-related action of a stable analog of chicken II GnRH (SEQ ID NO: 2) on progesterone production was defined using baboon granulosa cell cultures. After a two hour basal study period, the medium was supplemented with either Buserilin ($10^{-7}$) or a chicken H GnRH analog (SEQ ID NO: 2) ($10^{-9}$, $10^{-8}$, $10^{-7}$, $10^{-6}$ M) leaving four control wells. The average progesterone releases normalized to each well's basal release after 22 and 46 hours was compared among groups as seen in FIGS. 28 and 29. Incubation of baboon granulosa cells with the chicken II GnRH analog (SEQ ID NO: 2) resulted in a dose-related inhibition of progesterone release attaining maximal inhibition at $10^{-8}$M within 24 hours of exposure, i.e. 31% of untreated controls as seen in FIG. 30. This inhibition was sustained after 48 hours of treatment. Buserelin was without significant effect. In addition, the action of the analog on three different stromal and three different epithelial endometrial primary cell lines (after 3–5 passages) has been studied and $PGE_2$ determined as indicated in FIG. 31.

EXAMPLE XV

Non-Mammalian GnRH Analogs and Methods of Use in Treatment of Conditions of the Ovary, Fallopian Tubes, and Uterus Due to the stability of the non-mammalian GnRH analogs, particularly chicken II GnRH (SEQ ID NO: 2) and Salmon analogs (SEQ ID NO: 4), in the blood and reproductive tissues, the presence of binding receptors in reproductive tissues, and their biological activity in reproductive tissues, such analogs can be used in the treatment of conditions of or regulation of the reproductive system and the tissues therein including, but not limited to the endometrium, ovary, fallopian tubes, and uterus. Such treatment or regulation may be for endometriosis, polycystic ovarian disease, ovarian cysts, tubals, abnormal uterine bleeding, leiomyomas, endometrial polyps, fallopian tube mobility, function or obstruction, ectopic pregnancy, molar pregnancy, trophoblastic disease, abnormal placentation, such as pre-eclampsia, intrauterine growth retardation, preterm labor, preservation of the ovary during chemotherapy, in vitro fertilization, and ovarian atresia.

Conventional methods, known to those of ordinary skill in the art of medicine, can be used to administer the pharmaceutical formulation(s) to the patient. Typically, the pharmaceutical formulation will be administered to the patient by intramuscular injection, subdermal pellet, or nasal spray. The pharmaceutical formulation(s) can also be administered via other conventional routes (e.g., oral, subcutaneous, intrapulmonary, transmucosal, intraperitoneal, intrauterine, vaginal, sublingual, or intrathecal routes) by using standard methods. In addition, the pharmaceutical formulations can be administered to the patient via injection depot routes of administration such as by using 1-, 3-, or 6-month depot injectable or biodegradable materials and methods.

Regardless of the route of administration, the therapeutical agent typically is administered at a daily dosage of 0.001 µg to 30 mg/kg of body weight of the patient. The pharmaceutical formulation can be administered in multiple doses per day, if desired, to achieve the total desired daily dose or as a long acting depot.

The effectiveness of the method of treatment can be assessed by monitoring the patient for known signs or symptoms of the disorder. Common symptoms of endometriosis include onset of increasing painful periods, steady dull to severe lower abdominal pain, pelvic or low back pain that may occur at any time during the menstrual cycle, severe pelvic cramps or abdominal pain that may start 1 to 2 weeks before the menstrual cycle, more frequent or totally irregular periods, premenstrual spotting, pain during or following sexual intercourse, pain with bowel movements, and infertility. A laparoscopy is typically performed to make the determination. For ovarian cysts, the symptoms include abnormal uterine bleeding (lengthened, shortened, absent, or irregular menstrual cycle), constant dull aching pelvic pain, pain with intercourse or pelvic pain during movement, pelvic pain shortly after onset or cessation of menses, nausea/vomiting or breast tenderness similar to that associated with pregnancy. Prolonged symptoms that may be associated with polycystic ovarian disease include abnormally light or lack of menstrual periods, infertility, obesity, swollen abdomen, abdominal mass, and hirsutism. Hormonal level tests are typically ordered including FSH, LH, estrogen, and pregnanediol. A serum hCG test may be done to rule out pregnancy.

The symptoms of abnormal uterine bleeding, uterine fibroids, or leiomyomas, may include menorrhagia, menometrorrhagia, severe pressure or pain, urinary or bowel complaints, recurrent abortions, and infertility. Some patients may however be asymptomatic. Diagnosis is made by pelvic examination and can be confirmed by ultrasonography, CT or MRI. While discussion has been made concerning specifically the female reproductive system, this invention have great applicability in the male reproductive system and conditions of the male reproductive system as the developmental reproductive biology of males and females is known by those skilled in the art to have a common origin. By way of example only, it is anticipated that the present invention in the treatment of conditions of or regulation of male reproductive tissues has particular applicability in testicular descent, testicular function, prostate function and preservation of testis during chemotherapy. In addition, it is believed by the present inventor that the non-mammalian GnRH analogs of the present invention can be used in the regulation of the immune system in pregnant and non-pregnant individuals and in systemic lupus erythematosus.

While the compositions and methods of this invention have been described in terms of preferred embodiments, it will be apparent to those of skill in the are that variations maybe applied to the composition, methods and in the steps or in the sequence of steps of the method described herein without departing from the concept, spirit and scope of the invention. More specifically, it will be apparent that certain agents, who are both chemically and physiologically, related, might be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A chicken II GnRH analog, having the sequence p-Glu-His-Trp-Ser-His-Xaa1-Trp-Tyr-Pro-Xaa2, capable of binding to tubal, endometrial, uterine, prostate or testicular GnRH receptors and active in the presence of a post-proline peptidase or an endopeptidase, said analog comprising a D-amino acid substitution at position 6 and an ethylamide or aza-Gly-amide substitution at position 10.

2. The chicken II GnRH analog of claim 1 wherein the chicken II GnRH analog is further defined as:
   D-Arg(6)-chicken II GnRH-ethylamide; or
   D-Arg(6)-chicken II GnRH-aza-Gly(10)-amide.

3. The chicken II GnRH analog of claim 1 wherein the post-proline peptidase is chorionic peptidase-1.

4. The chicken II GnRH analog of claim 2 wherein the chicken II GnRH analog is further defined as D-Arg(6)-chicken II GnRH-aza-Gly(10)-amide having a sequence as defined in SEQ ID NO: 2 (p-Glu-His-Trp-Ser-His-D-Arg-Trp-Tyr-Pro-aza-Gly-NH$_2$).

5. The chicken II GNRE analog of claim 1 wherein the chicken II GnRH analog is further defined as an aza-Gly (10)-amide Chicken II GnRH analog.

6. The chicken II GnRH analog of claim 1 wherein the chicken II GnRH analog is further defined as comprising a D-Arg, a D-Leu, D-tBu-serine, or a D-Trp substitution at position 6 and an aza-Gly amide or an ethylamide at position 10.

7. A pharmaceutical preparation comprising a compound according to claim 4, in admixture with a pharmaceutically acceptable carrier, diluent or excipient.

8. A purified polypeptide, the amino acid sequence of which comprises SEQ ID NO: 2.

* * * * *

UNITED STATES PATENT AND TRADEMARK OFFICE
CERTIFICATE OF CORRECTION

PATENT NO. : 6,635,739 B2
DATED : October 21, 2003
INVENTOR(S) : Theresa Siler-Khodr It is certified that error appears in the above-identified patent and that said Letters Patent is hereby corrected as shown below:

<u>Drawings,</u>
Figs. 31A through 31F, delete "PGF2" and insert -- PGE2 -- in its place.

Signed and Sealed this

Thirtieth Day of December, 2003

JAMES E. ROGAN
*Director of the United States Patent and Trademark Office*